(12) United States Patent
Dai et al.

(10) Patent No.: US 12,391,677 B2
(45) Date of Patent: Aug. 19, 2025

(54) THYROID HORMONE RECEPTOR AGONISTS

(71) Applicant: INVENTISBIO CO., LTD., Shanghai (CN)

(72) Inventors: Xing Dai, Shanghai (CN); Yaolin Wang, Shanghai (CN); Yueheng Jiang, Shanghai (CN); Yanqin Liu, Shanghai (CN); Zixing Han, Shanghai (CN); Zhenwu Wang, Shanghai (CN); Liangshan Tao, Shanghai (CN); Zhe Shi, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 882 days.

(21) Appl. No.: 17/284,149

(22) PCT Filed: Oct. 11, 2019

(86) PCT No.: PCT/CN2019/110494
§ 371 (c)(1),
(2) Date: Apr. 9, 2021

(87) PCT Pub. No.: WO2020/073974
PCT Pub. Date: Apr. 16, 2020

(65) Prior Publication Data
US 2021/0355110 A1 Nov. 18, 2021

(30) Foreign Application Priority Data

Oct. 12, 2018 (WO) ............... PCT/CN2018/109942
Feb. 20, 2019 (WO) ............... PCT/CN2019/075501

(51) Int. Cl.
| | | |
|---|---|---|
| *C07D 403/12* | (2006.01) | |
| *A61K 31/501* | (2006.01) | |
| *A61K 31/53* | (2006.01) | |
| *A61P 5/16* | (2006.01) | |
| *C07D 401/14* | (2006.01) | |
| *C07D 403/10* | (2006.01) | |
| *C07D 403/14* | (2006.01) | |
| *C07D 405/14* | (2006.01) | |
| *C07D 413/14* | (2006.01) | |
| *C07D 471/04* | (2006.01) | |
| *C07F 9/6509* | (2006.01) | |

(52) U.S. Cl.
CPC .......... *C07D 403/12* (2013.01); *A61K 31/501* (2013.01); *A61K 31/53* (2013.01); *A61P 5/16* (2018.01); *C07D 401/14* (2013.01); *C07D 403/10* (2013.01); *C07D 403/14* (2013.01); *C07D 405/14* (2013.01); *C07D 413/14* (2013.01); *C07D 471/04* (2013.01); *C07F 9/650905* (2013.01)

(58) Field of Classification Search
CPC .. C07D 403/12; C07D 401/14; C07D 403/10; C07D 403/14; C07D 405/14; C07D 413/14; C07D 471/04; C07F 9/650905; A61K 31/501; A61K 31/53; A61P 5/16
See application file for complete search history.

(56) References Cited

U.S. PATENT DOCUMENTS 11,964,964 B2  4/2024  Jin et al.

FOREIGN PATENT DOCUMENTS

| CN | 111801324 | 10/2020 | |
|---|---|---|---|
| EP | 1 471 049 | 10/2004 | |
| WO | 2007/009913 | 1/2007 | |
| WO | WO-2007009913 A1 * | 1/2007 | ........... A61K 31/501 |
| WO | 2009/037172 | 3/2009 | |
| WO | 2014/043706 | 3/2014 | |

OTHER PUBLICATIONS

Fletcher et. al. ((2017, Comprehensive Cognitive Assessments are not Necessary for the Identification and Treatment of Learning Disabilities, Archives of Clinical Neuropsychology, 32, 2-7 (Year: 2017).*
Muller et. al. ((2015), New Treatment options for hearing loss, Nature Reviews Drug Discovery, 14, 346-365 (Year: 2015).*
Martha J. Kelly et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia", American Chemical Society, Journal of Medicinal Chemistry, 2014, 57, 3912-3923.

(Continued)

*Primary Examiner* — Juliet C Switzer
*Assistant Examiner* — Dawanna Shar-Day White
(74) *Attorney, Agent, or Firm* — NIXON & VANDERHYE, PC

(57) ABSTRACT

Provided herein are novel thyroid hormone receptor (TR) agonists e.g., having Formula I, II, or III. Also provided are methods of preparing the novel TR agonists and method of using the novel TR agonists for treating diseases or disorder modulated by TR agonists, such as NAFLD, NASH, diabetes, hyperlipidemia and/or hypercholesterolemia.

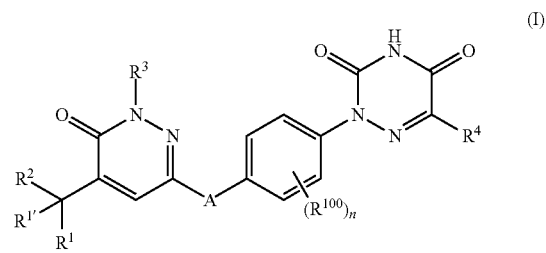

10 Claims, No Drawings

(56) References Cited

OTHER PUBLICATIONS

International Search Report for PCT/CN2019/110494 mailed Jan. 16, 2020, 6 pages.
Written Opinion of the ISA for PCT/CN2019/110494 mailed Jan. 16, 2020, 6 pages.

* cited by examiner

THYROID HORMONE RECEPTOR AGONISTS

CROSS REFERENCE TO RELATED APPLICATIONS

This application is the U.S. national phase of International Application No. PCT/CN2019/110494 filed Oct. 11, 2019 which designated the U.S. and claims priority of International Application No. PCT/CN2018/109942, filed on Oct. 12, 2018 and International Application No. PCT/CN2019/075501, filed on Feb. 20, 2019, the entire contents of each of which are incorporated herein by reference.

BACKGROUND OF THE INVENTION

Field of the Invention

In various embodiments, the present invention relates to novel thyroid hormone receptor agonists, pharmaceutical compositions, methods of preparing and methods of using the same, for example, for treating diseases or disorders such as nonalcoholic fatty liver disease and/or non-alcoholic steatohepatitis.

Background Art

Thyroid hormone (TH) plays a critical role in the human endocrine system and controls the energy metabolism through regulating the protein synthesis, carbohydrate and fat metabolism in liver, skeletal muscle and adipose tissue. In addition, TH affects cardiovascular, bone and renal functions. The activities of TH are mediated through its binding to thyroid hormones receptors (TRs), which include both isoforms of TRα and TRβ. TRα is primarily expressed in the brain and heart and to a lesser extent in kidney, skeletal muscle, lungs, whereas TRβ is predominantly expressed in the liver, kidneys and at lower levels in brain, heart, thyroid, skeletal muscle, lungs, and spleen. Therefore, TRα mainly affects the heart function, whereas TRβ controls carbohydrate and lipid metabolism in the liver.

TH regulates the energy expenditure through both central and peripheral actions. It maintains basal metabolic rate, facilitates adaptive thermogenesis, modulates appetite and food intake, and regulates body weight. Upon binding to thyroid hormones, TRs bind to the thyroid hormone response elements (TREs) of their downstream target genes to activate gene expression and hence the TR signaling pathway. In the absence of hormone, transcriptional regulation is blocked through TRs' association with co-repressors.

Non-alcoholic fatty liver disease (NAFLD) is a global epidemic with an incidence of 30% or more among adults in both developed and developing countries. NAFLD is considered to be a hepatic manifestation of the metabolic syndrome and is closely associated with the development of other metabolic risk factors such as type 2 diabetes mellitus, hyperlipidemia and coronary artery disease. NAFLD represents a spectrum of liver diseases that include excessive accumulation of lipids in the hepatocytes, which is initially benign (hepatosteatosis) but progresses to a more advanced stage with inflammation (non-alcoholic steatohepatitis, NASH) and culminates in fibrosis accompanied by increased inflammation, apoptosis and scarring of liver tissue (cirrhosis). Patients with cirrhosis eventually progress to hepatocellular carcinoma (HCC). Therefore, patients with NAFLD and/or NASH have an increased risk of developing HCC later in life.

BRIEF SUMMARY OF THE INVENTION

In various embodiments, the present invention provides novel TR agonists, pharmaceutical compositions comprising the compounds, methods of preparing the compounds, and methods of using the compounds, for example, for the treatment of a disease or disorder modulated by TR agonists, such as a non-alcoholic fatty liver disease and/or NASH.

In various embodiments, the present disclosure provides novel TR agonists having Formula I, Formula II, or Formula III, or a pharmaceutically acceptable salt thereof:

Formula I

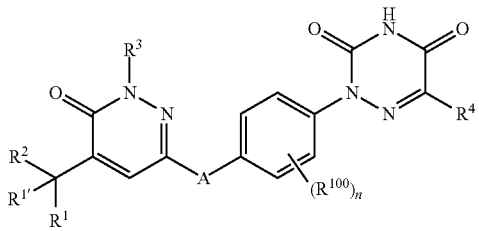

Formula II

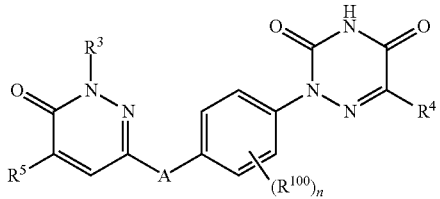

Formula III

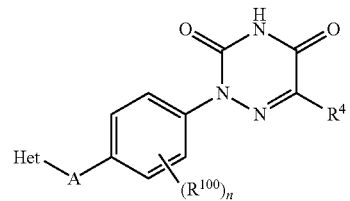

wherein the variables Het, A, $R^1$, $R^{1'}$, $R^2$, $R^3$, $R^4$, $R^5$, $R^{100}$, and n in compounds of Formula I, II, or III, as applicable, are defined herein. In some embodiments, the compound can have a Formula I-1, Formula I-2, Formula I-3, Formula I-4, Formula II-1, Formula III-1, Formula III-2, Formula III-3, Formula III-4, Formula III-1A, Formula III-2A, Formula III-3A, Formula III-4A, Formula I-X, Formula II-X, or Formula III-X, any one of compounds 1-99, as defined herein. In some specific embodiments, the compound can be any one of compounds 1-99.

Certain embodiments of the present disclosure are directed to a pharmaceutical composition comprising a compound of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), Formula I-X, Formula II-X, or Formula III-X, any one of compounds 1-99, as defined herein, or a pharmaceutically acceptable salt thereof. The pharmaceutical composition described herein can be formulated for different routes of administration, such as oral administration, parenteral administration, or inhalation etc.

Certain embodiments of the present disclosure are directed to a method of treating a disease or disorder associated with TR agonist, such as a non-alcoholic fatty liver disease. In some embodiments, the method comprises administering to the subject in need thereof a therapeutically effective amount of a compound of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), Formula I-X, Formula II-X, or Formula III-X, any one of compounds 1-99, as defined herein, or a pharmaceutically acceptable salt thereof, or a pharmaceutical composition comprising the compound or pharmaceutically acceptable salt thereof, as defined herein. In some embodiments, the administering comprises administration via oral administration, parenteral administration or inhalation. Non-limiting diseases or disorders suitable to be treated with the methods described herein include obesity, hyperlipidemia, hypercholesterolemia, diabetes, non-alcoholic steatohepatitis, fatty liver, non-alcoholic fatty liver disease, bone disease, thyroid axis alteration, atherosclerosis, a cardiovascular disorder, tachycardia, hyperkinetic behavior, hyperthyroidism, goiter, attention deficit hyperactivity disorder, learning disabilities, mental retardation, hearing loss, delayed bone age, neurologic or psychiatric disease, thyroid cancer, and combinations thereof.

It is to be understood that both the foregoing summary and the following detailed description are exemplary and explanatory only, and are not restrictive of the invention herein.

DETAILED DESCRIPTION OF THE INVENTION

TR agonists have shown significant promise in the treatment of hypercholesterolemia, hepatic steatosis, and weight loss. However, these non-selective TR agonists have been associated with adverse action on heart, bone and cartilage. Therefore, more selective and specific agents targeting TH signaling pathways, based on improved mechanistic understanding, will be needed to effectively and selectively target metabolic diseases.

Recent studies suggest that thyroid hormone analogues that are specific for TRβ have potential therapeutic benefit for metabolic conditions such as NAFLD and NASH. For example, MGL-3196 was reported to be a liver-targeted thyroid hormone receptor-beta agonist with certain selectivity over TR-alpha. MGL-3196 was also found to be useful for lowering lipid content in clinical trials. See e.g., *Atherosclerosis* 230:373-380 (2013). Structurally, MGL-3196 is a pyridazinone compound with an azauracil ring, which mimics the natural ligand triiodothyronine (T3). Limited structural activity relationship (SAR) was published for pyridazinone compounds similar to MGL-3196. *J. Med. Chem.* 57:3912-3923 (2014). The disclosed SAR indicates that the optimal substituent on the pyridazinone ring is isopropyl, and the optimal substituent for the azauracil unit is CN, which enhances selectivity over TR alpha. The center phenyl ring is typically substituted with two chlorine groups.

In various embodiments, the present inventors unexpected found that the CN group on the azauracil ring can be replaced with a hydrophobic group, such as an alkyl, without diminishing its selectivity over TR alpha. Further, such replacement also provided compounds with minimal cellular shift from the receptor binding assay, which means that the observed $EC_{50}$ for a cell-based assay is similar to that observed for the receptor binding assay (see details in the Examples section). In various embodiments, the present invention is also based in part on the unexpected discovery that the reported optimal isopropyl group can be modified into various optionally substituted alkyl, cycloalkyl, phenyl, or heterocyclyl group, and the resulted compounds can not only maintain efficacy for TR beta, but in some cases, with improved efficacy and/or with much diminished TR alpha activity. Thus, such modifications can reduce side effects associated with undesired TR alpha activity, for example, in organs such as the heart. Further, in various embodiments, the present inventors found that the center phenyl ring substitution, which is typically a 2,6-dichlorophenyl, can be modified to achieve higher TR beta potency and/or better selectivity over TR alpha. Additionally, representative compounds of the present disclosure also show enhanced stability in the microsomal stability study, which suggests better pharmacokinetic profile over MGL-3196. Accordingly, in various embodiments, the present invention provides novel compounds containing any one or more of these modifications.

In some embodiments, the present invention provides a compound of Formula I, or a pharmaceutically acceptable salt thereof:

Formula I

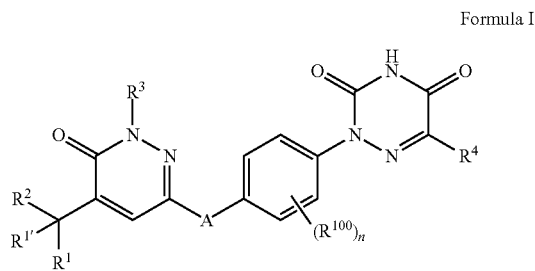

wherein:
$R^1$ and $R^{1'}$ are each independently hydrogen, OH, halogen (e.g., F), or an optionally substituted $C_{1-4}$ alkyl (e.g., $C_{1-4}$ alkyl), or $R^1$ and $R^{1'}$ together form an oxo (=O),
$R^2$ is an optionally substituted alkyl, an optionally substituted carbocyclyl, an optionally substituted heterocyclyl, an optionally substituted aryl, or an optionally substituted heteroaryl; or $R^2$ is —COOH or an ester thereof, —CONH$_2$, —CONH($C_{1-6}$ alkyl), —CON($C_{1-6}$ alkyl)($C_{1-6}$ alkyl), wherein each of the $C_{1-6}$ alkyl is independently selected and optionally substituted,
A is O, CH$_2$, S, SO or SO$_2$,
$R^3$ is hydrogen or an optionally substituted alkyl,
$R^{100}$ at each occurrence is independently F, Cl, Br, I, $C_{1-4}$ alkyl optionally substituted with 1-3 fluorine, cyclopropyl, cyclobutyl, $C_{1-4}$ alkoxy optionally substituted with 1-3 fluorine, cyclopropoxy, or cyclobutoxy,
n is 1, 2, 3, or 4,
$R^4$ is hydrogen, —CN, —COOH, optionally substituted alkyl (e.g., optionally substituted $C_{1-6}$ alkyl), or optionally substituted carbocyclyl (e.g., optionally substituted $C_{3-6}$ carbocyclyl).

In some embodiments, when —CR$^1$R$^{1'}$R$^2$ is isopropyl or —CH(CH$_3$)(CH$_2$—OH), then R$^4$ is not hydrogen, —COOH, or —CN. In any of the embodiments herein according to Formula I, R$^2$ can be an optionally substituted alkyl, an optionally substituted carbocyclyl, an optionally substituted heterocyclyl, an optionally substituted aryl, or an optionally substituted heteroaryl, which is further defined herein.

In some embodiments, the compound of Formula I can be characterized as having a Formula I-1:

Formula I-1

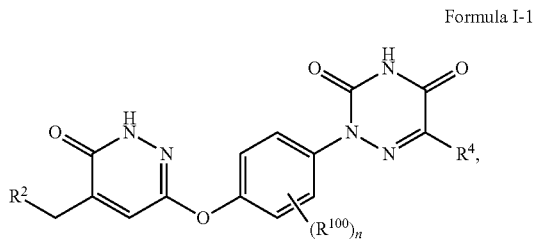

wherein $R^2$, $R^{100}$, n, and $R^4$ are defined herein.

In some embodiments, the compound of Formula I can be characterized as having a Formula I-2:

Formula I-2

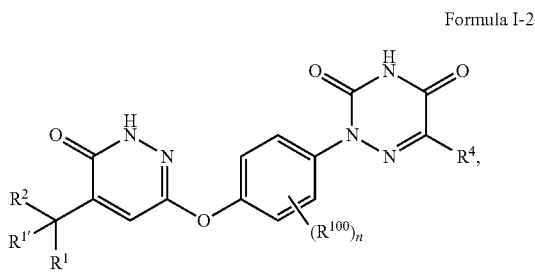

wherein $R^1$, $R^{1'}$, $R^2$, $R^4$, $R^{100}$, and n are defined herein.

In some embodiments, the compound of Formula I can be characterized as having a Formula I-3:

Formula I-3

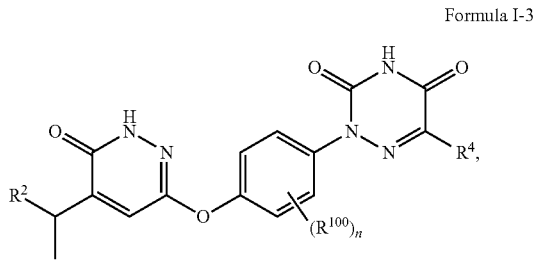

wherein $R^2$, $R^{100}$, n, and $R^4$ are defined herein. When $R^2$ is not methyl, for example, when $R^2$ is cyclohexyl or phenyl, the compound of Formula I-3 has at least one chiral center, which can exist in the form of individual enantiomers, or a mixture of the two enantiomers in any ratio, including racemic mixture, when applicable. In cases where two or more chiral centers are present, the compound of Formula I-3 can exist in the form of individual stereoisomers, or any stereoisomeric mixtures thereof. As exemplified in the Examples section, representative compounds of Formula I-3 having one chiral center (e.g., when $R^2$ is cyclohexyl or phenyl) can be prepared in racemic forms or can be separated into individual enantiomers, e.g., using chiral HPLC. When specified as an individual enantiomer, such as enantiomer A or B, identified as the first or second eluted enantiomer optionally with a retention time from an analytical HPLC trace, it should be understood that the individual enantiomer is enriched, for example, the individual enantiomer can be substantially free of the other enantiomer (e.g., less than 20%, less than 15%, less than 10%, less than 5%, less than 2%, less than 1%, or less than 0.5%, or not detected, as determined by analytical chiral HPLC).

Typically, $R^1$ and $R^{1'}$ in Formula I (e.g., Formula I-2) are independently hydrogen or an optionally substituted $C_{1-4}$ alkyl (e.g., $C_{1-4}$ alkyl). In some embodiments, both $R^1$ and $R^{1'}$ are hydrogen. In some embodiments, one of $R^1$ and $R^{1'}$ is hydrogen and the other of $R^1$ and $R^{1'}$ is a $C_{1-4}$ alkyl (such as a methyl, ethyl, etc.). In some embodiments, one of $R^1$ and $R^{1'}$ is hydrogen and the other of $R^1$ and $R^{1'}$ is a $C_{1-4}$ alkyl (such as a methyl, ethyl, etc.), optionally substituted with one or more substituents, e.g., one substituent such as hydroxyl. In some embodiments, both of $R^1$ and $R^{1'}$ are $C_{1-4}$ alkyl (such as a methyl, ethyl, etc.). In some embodiments, both of $R^1$ and $R^{1'}$ are $C_{1-4}$ alkyl (such as a methyl, ethyl, etc.), optionally substituted with one or more substituents, e.g., one substituent such as hydroxyl.

The present inventors also unexpected found that when $R^1$ and $R^{1'}$ together form an oxo (=O), the resulted compounds can bind to TR beta with a potency similar to MGL-3136 with reasonable selectivity over TR alpha. Thus, some embodiments of the present invention are also directed to compounds having Formula I, wherein $R^1$ and $R^{1'}$ together form an oxo (=O), such as compounds of Formula I-4:

Formula I-4

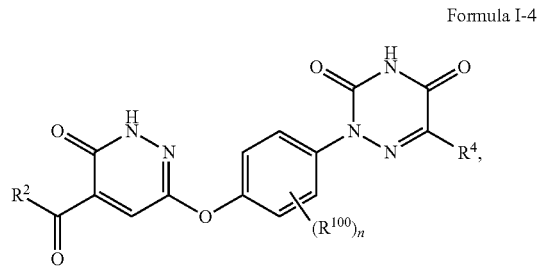

In some embodiments, one of $R^1$ and $R^{1'}$ in Formula I (e.g., Formula I-2) can also be OH and the other of $R^1$ and $R^{1'}$ is defined herein. In some embodiments, one of $R^1$ and $R^{1'}$ in Formula I (e.g., Formula I-2) can also be a halogen (e.g., F) and the other of $R^1$ and $R^{1'}$ is defined herein. In some embodiments, both of $R^1$ and $R^{1'}$ in Formula I (e.g., Formula I-2) can be a halogen (e.g., F).

Typically, A in Formula I is O, $CH_2$, S, SO or $SO_2$. In some embodiments, A is O. In some embodiments, A is $CH_2$. In some embodiments, A can also be S. It should be noted that in any of the embodiments described herein, as applicable, corresponding embodiments with A as CO, $CF_2$, NH, N($C_{1-4}$ alkyl), or a protected NH, are also contemplated and are novel compounds of the present invention.

In some embodiments, $R^3$ is hydrogen. In some embodiments, $R^3$ is an optionally substituted alkyl that can be metabolically converted into a corresponding compound with $R^3$ being hydrogen. In some embodiments, $R^3$ can be an optionally substituted $C_{1-4}$ alkyl. For example, in some embodiments, $R^3$ can be a $C_{1-4}$ alkyl, such as a methyl, optionally substituted with one or more groups (such as one) independently selected from —OH, a protected hydroxyl group, and —OR, wherein R can be any feasible group that can be stably attached to oxygen such as an oxygen atom substituent described herein. For example, in some embodiments, —OR can be an O-linked amino acid, —OP(O)(OH)$_2$, or —OC(O)—$R^{101}$, wherein $R^{101}$ can be an optionally substituted $C_{1-6}$ alkyl, optionally substituted $C_{1-6}$ alkoxy, optionally substituted —$C_{1-6}$ alkylene-COOH, optionally substituted $C_{3-6}$ cycloalkyl, optionally substituted 4-7 membered heterocyclyl, optionally substituted 5-10 membered heteroaryl, or optionally substituted aryl. In some embodiments, $R^3$ can be a $C_{1-4}$ alkyl, such as a methyl, optionally substituted with one or more, such as one, —OH or a protected hydroxyl group. Suitable hydroxyl protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference. As used herein, the term "O-linked amino acid" means any amino acid, naturally occurring or synthetic, linked to a molecule via an oxygen of a carboxyl group of said amino acid, preferably via the carboxyl group of the carboxy terminus of said amino acid. Preferred examples of amino acids are (S)-2-amino-3-methyl-butyric acid, (2S,3S)-2-amino-3-methyl-pentanoic acid and (S)-2-amino-propionic acid.

Various acyclic or cyclic groups are suitable for $R^2$ in Formula I (e.g., Formula I-1, I-2, I-3, or I-4). In some embodiments, $R^2$ can be an optionally substituted carbocyclyl. For example, in some embodiments, $R^2$ can be an optionally substituted $C_{3-6}$ cycloalkyl, e.g., with one or two substituents independently selected from $C_{1-4}$ alkyl optionally substituted with 1-3 fluorine, —OH, —OPg$^1$, $C_{1-4}$ alkoxy optionally substituted with 1-3 fluorine, and halogen, wherein Pg$^1$ is an oxygen protecting group. In some embodiments, $R^2$ can be cyclopropyl, cyclobutyl, cyclopentyl, or cyclohexyl, each of which can be optionally substituted with 1 or 2 substituents independently selected from F, methyl and hydroxyl.

In some embodiments, $R^2$ can be an alkyl such as a $C_{1-4}$ alkyl optionally substituted with one or more substituents independently selected from optionally substituted $C_{3-6}$ cycloalkyl, optionally substituted phenyl, optionally substituted 4-7 membered heterocyclyl (e.g., piperidinyl or tetrahydropyranyl), optionally substituted 5-10 membered heteroaryl, —OH, —OPg$^1$, $C_{1-4}$ alkoxy optionally substituted with 1-3 fluorine, and halogen, wherein Pg$^1$ is an oxygen protecting group. For example, in some embodiments, $R^2$ can be a $C_{1-4}$ alkyl (e.g., methyl) substituted with one substituent selected from optionally substituted $C_{3-6}$ cycloalkyl (e.g., as described herein), optionally substituted phenyl, optionally substituted 4-7 membered heterocyclyl (e.g., as described herein), and optionally substituted 5-10 membered heteroaryl (e.g., as described herein). In some embodiments, $R^2$ can be a $C_{1-4}$ alkyl (e.g., methyl) substituted with one optionally substituted $C_{3-6}$ cycloalkyl, e.g., with one or two substituents independently selected from $C_{1-4}$ alkyl optionally substituted with 1-3 fluorine, —OH, —OPg$^1$, $C_{1-4}$ alkoxy optionally substituted with 1-3 fluorine, and halogen, wherein Pg$^1$ is an oxygen protecting group. In some embodiments, $R^2$ can be a $C_{1-4}$ alkyl (e.g., methyl) substituted with one optionally substituted cyclopropyl, cyclobutyl, cyclopentyl, or cyclohexyl, each of which can be optionally substituted with 1 or 2 substituents independently selected from F, methyl and hydroxyl. In some embodiments, $R^2$ can be a $C_{1-4}$ alkyl (e.g., methyl) substituted with one phenyl group which is optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkoxy (e.g., methoxy, ethoxy, etc.) optionally substituted with 1-3 fluorine, hydroxyl, and CN. In some embodiments, $R^2$ can be a $C_{1-4}$ alkyl (e.g., methyl) substituted with one phenyl group which is optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkyl substituted with one or two hydroxyl groups, $C_{1-4}$ alkoxy (e.g., methoxy, ethoxy, etc.) optionally substituted with 1-3 fluorine, hydroxyl, and CN. In some embodiments, $R^2$ can be a $C_{1-4}$ alkyl (e.g., methyl) substituted with one 5- or 6-membered heteroaryl group (e.g., as described herein, such as pyridinyl, pyrrazolyl, isoxazolyl, etc.), which is optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkyl substituted with one or two hydroxyl groups, $C_{1-4}$ alkoxy (e.g., methoxy, ethoxy, etc.) optionally substituted with 1-3 fluorine, hydroxyl, and CN. In some embodiments, $R^2$ can be a $C_{1-4}$ alkyl (e.g., methyl) substituted with one 5,6- or 6,6-bicyclic heteroaryl group (e.g., as described herein, such as indazolyl, etc.), which is optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkyl substituted with one or two hydroxyl groups, $C_{1-4}$ alkoxy (e.g., methoxy, ethoxy, etc.) optionally substituted with 1-3 fluorine, hydroxyl, and CN. In some embodiments, $R^2$ can be a $C_{1-4}$ alkyl (e.g., methyl) substituted with one optionally substituted 4-7 membered heterocyclyl (e.g., piperidinyl or tetrahydropyranyl), e.g., with one or two substituents independently selected from a nitrogen protecting group, as applicable, $C_{1-4}$ alkyl optionally substituted with 1-3 fluorine, —OH, —OPg$^1$, $C_{1-4}$ alkoxy optionally substituted with 1-3 fluorine, and halogen, wherein Pg$^1$ is an oxygen protecting group.

In some embodiments, $R^2$ can be an optionally substituted heterocyclyl, preferably an optionally substituted 4-7 membered heterocyclyl (e.g., piperidinyl or tetrahydropyranyl), e.g., with one or two substituents independently selected from $C_{1-4}$ alkyl optionally substituted with 1-3 fluorine, —OH, —OPg$^1$, $C_{1-4}$ alkoxy optionally substituted with 1-3 fluorine, and halogen, wherein Pg$^1$ is an oxygen protecting group. When the 4-7 membered heterocyclyl has a NH, it can be optionally substituted with a nitrogen atom substituent as described herein such as a nitrogen protecting group, e.g., benzyl or substituted benzyl, —C(O)—$C_{1-4}$ alkyl or —C(O)—O—$C_{1-4}$ alkyl. For example, in some embodiments, $R^2$ can be an optionally substituted 5 or 6 membered saturated heterocyclyl containing one or two heteroatoms, such as one oxygen, one oxygen and one nitrogen, one nitrogen, two nitrogen atoms, etc. In some embodiments, $R^2$ can be piperidinyl or tetrahydropyranyl, which can be optionally substituted, for example, the piperidinyl can in some embodiments be substituted with one nitrogen atom substituent as described herein such as a nitrogen protecting group, e.g., —C(O)—$C_{1-4}$ alkyl or —C(O)—O—$C_{1-4}$ alkyl.

In some embodiments, $R^2$ can be an optionally substituted aryl such as an optionally substituted phenyl, e.g., with one or more such as 1 or 2 substituents independently selected from $C_{1-4}$ alkyl optionally substituted with 1-3 fluorine, —OH, —OPg$^1$, $C_{1-4}$ alkoxy optionally substituted with 1-3 fluorine, —CN, and halogen, wherein Pg$^1$ is an oxygen protecting group. In some embodiments, $R^2$ can be an optionally substituted phenyl, e.g., with one or two substituents independently selected from $C_{1-4}$ alkyl optionally substituted with 1-3 fluorine, $C_{1-4}$ alkyl substituted with one or two hydroxyl groups, —OH, —OPg$^1$, $C_{1-4}$ alkoxy optionally substituted with 1-3 fluorine, —CN, and halogen, wherein Pg$^1$ is an oxygen protecting group. For example, in some embodiments, $R^2$ can be a phenyl optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkoxy (e.g., methoxy, ethoxy, etc.) optionally substituted with 1-3 fluorine, hydroxyl, and CN.

Heteroaryl groups are also suitable as $R^2$ groups for Formula I (e.g., Formula I-1, I-2, I-3, or I-4). In some embodiments, $R^2$ can be an optionally substituted 5-10 membered heteroaryl, e.g., 5-10 membered heteroaryl containing 1-3 heteroatoms independently selected from O, N, and S, wherein the heteroaryl is optionally substituted, e.g., with 1-5, such as with one or two substituents independently selected from $C_{1-4}$ alkyl optionally substituted with 1-3 fluorine, $C_{1-4}$ alkyl substituted with one or two hydroxyl groups, —OH, —$OPg^1$, $C_{1-4}$ alkoxy optionally substituted with 1-3 fluorine, —CN, and halogen, wherein $Pg^1$ is an oxygen protecting group. In some embodiments, $R^2$ can be an optionally substituted 5 or 6 membered heteroaryl, such as pyridyl, thiophenyl, furanyl, pyrrolyl, imidazolyl, pyrazolyl, oxazolyl, isoxazolyl, isothiazolyl, thiazolyl, triazolyl, oxadiazolyl, tetrazolyl, thiadiazolyl, pyridazinyl, pyrimidinyl, and pyrazinyl, optionally substituted, e.g., with 1-5, such as with one or two substituents independently selected from $C_{1-4}$ alkyl optionally substituted with 1-3 fluorine, $C_{1-4}$ alkyl substituted with one or two hydroxyl groups, —OH, —$OPg^1$, $C_{1-4}$ alkoxy optionally substituted with 1-3 fluorine, —CN, and halogen, wherein $Pg^1$ is an oxygen protecting group. Bicyclic heteroaryls are also suitable. For example, in some embodiments, $R^2$ can be a 5,6-bicyclic or 6,6-bicyclic heteroaryl, such as indolyl, pyrrolopyridinyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, and quinazolinyl, optionally substituted, e.g., with 1-5, such as with one or two substituents independently selected from $C_{1-4}$ alkyl optionally substituted with 1-3 fluorine, $C_{1-4}$ alkyl substituted with one or two hydroxyl groups, —OH, —$OPg^1$, $C_{1-4}$ alkoxy optionally substituted with 1-3 fluorine, —CN, and halogen, wherein $Pg^1$ is an oxygen protecting group. In some embodiments, $R^2$ can be a pyridyl (e.g., 2-, 3-, or 4-pyridyl), indazolyl, isoxazolyl, or pyrazolyl, which can be optionally substituted as described herein.

In some embodiments, $R^2$ can be selected from the following:

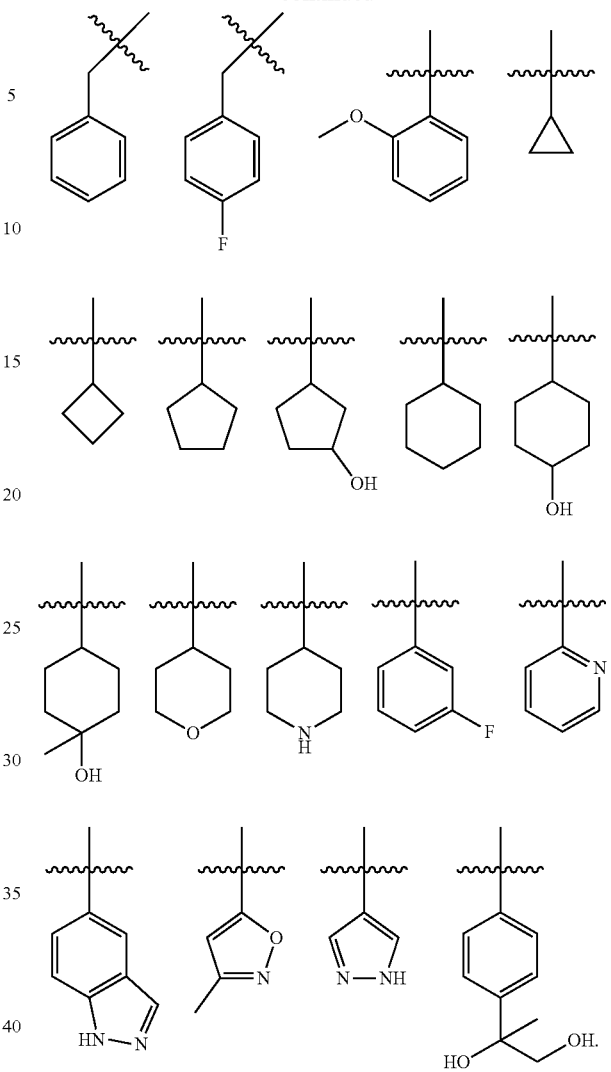

In some embodiments, $R^2$ can be selected from the following:

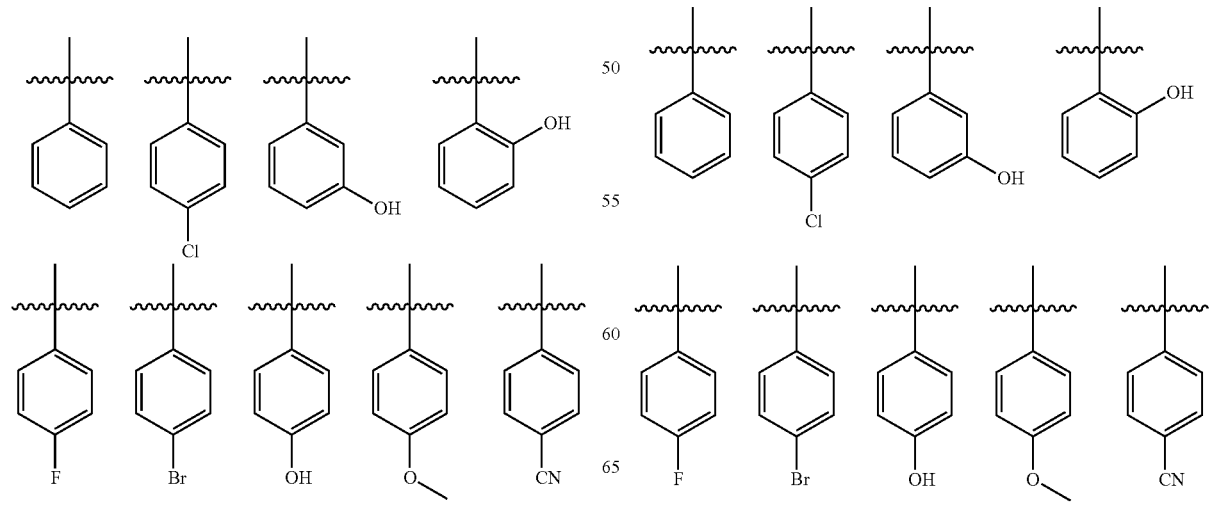

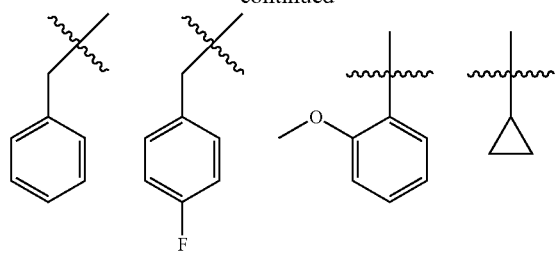

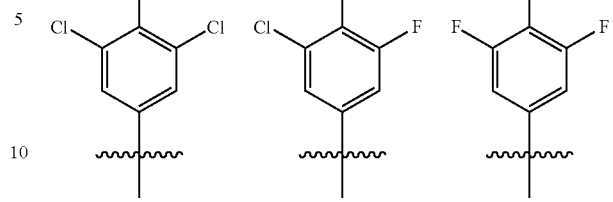

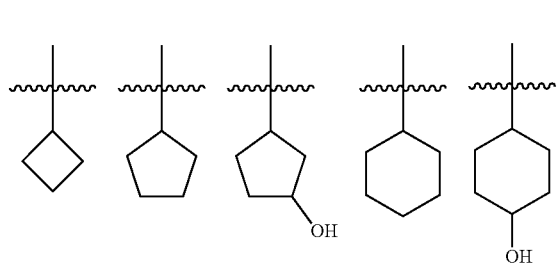

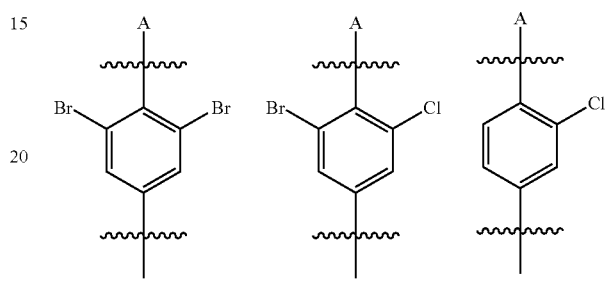

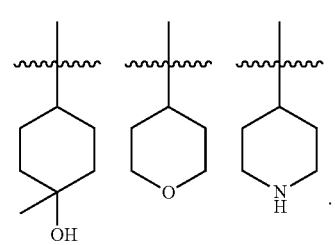

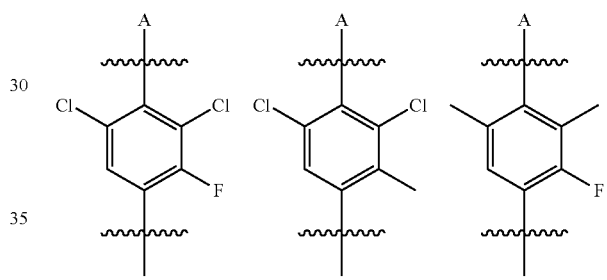

The phenyl ring in Formula I (e.g., Formula I-1, I-2, I-3, or I-4) is typically substituted with 2 or 3 independently selected $R^{100}$ groups, i.e., n is 2 or 3. In some embodiments, $R^{100}$ at each occurrence is independently F, Cl, Br, $CF_3$, or methyl. In some embodiments, one instance of $R^{100}$ is $CF_3$. Various substitution patterns for the phenyl ring in Formula I (e.g., Formula I-1, I-2, I-3, or I-4) are suitable. Typically, when 2 or 3 independently selected $R^{100}$ groups are present, two of the $R^{100}$ groups are attached to the ortho-positions of the linker A in Formula I, for example, as follows:

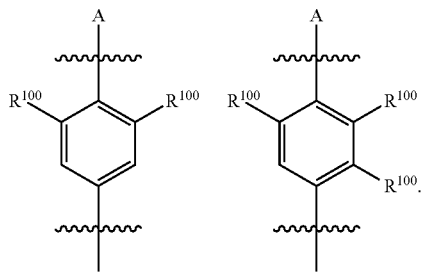

In some embodiments, the $R^{100}$ together with the phenyl ring they are attached to form one of the following:

In some embodiments, the $R^{100}$ together with the phenyl ring they are attached to form

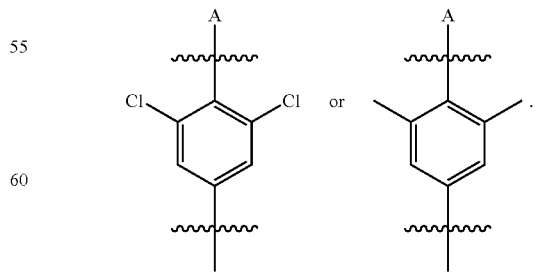

In some embodiments, the $R^{100}$ together with the phenyl ring they are attached to form

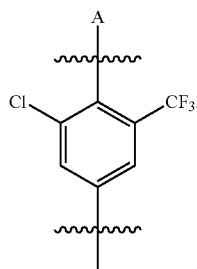

The substituent $R^4$ at the azauracil ring in Formula I (e.g., Formula I-1, I-2, I-3, or I-4) can vary. For example, in some embodiments, $R^4$ can be $C_{1-6}$ alkyl or $C_{3-6}$ cycloalkyl, each optionally substituted with 1-3 fluorine. In some embodiments, $R^4$ can be hydrogen, —CN, —COOH, methyl, ethyl, cyclopropyl, isopropyl, or propyl. In some preferred embodiments, $R^4$ in Formula I-1 can be hydrogen, —CN or methyl. In some preferred embodiments, $R^4$ in Formula I-1 can be methyl, ethyl, cyclopropyl, isopropyl, or propyl. In some preferred embodiments, $R^4$ in Formula I-2 can be hydrogen, —CN or methyl. In some preferred embodiments, $R^4$ in Formula I-2 can be methyl, ethyl, cyclopropyl, isopropyl, or propyl. In some preferred embodiments, $R^4$ in Formula I-3 can be hydrogen, —CN or methyl. In some preferred embodiments, $R^4$ in Formula I-3 can be methyl, ethyl, cyclopropyl, isopropyl, or propyl. In some preferred embodiments, $R^4$ in Formula I-4 can be hydrogen, —CN or methyl. In some preferred embodiments, $R^4$ in Formula I-4 can be methyl, ethyl, cyclopropyl, isopropyl, or propyl.

In some embodiments, the present invention provides a compound of Formula II, or a pharmaceutically acceptable salt thereof:

Formula II

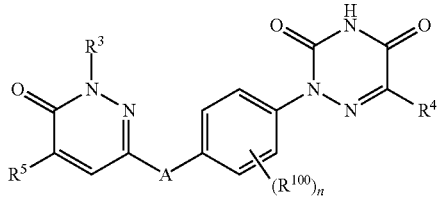

wherein:
$R^5$ is an optionally substituted aryl, an optionally substituted heteroaryl, an optionally substituted carbocyclyl or optionally substituted heterocyclyl; or $R^5$ is —COOH or an ester thereof, —CONH$_2$, —CONH($C_{1-6}$ alkyl), —CON($C_{1-6}$ alkyl)($C_{1-6}$ alkyl), wherein each of the $C_{1-6}$ alkyl is independently selected and optionally substituted;
A is O, CH$_2$, S, SO or SO$_2$,
$R^3$ is hydrogen or an optionally substituted alkyl,
$R^{100}$ at each occurrence is independently F, Cl, Br, I, $C_{1-4}$ alkyl optionally substituted with 1-3 fluorine, cyclopropyl, cyclobutyl, $C_{1-4}$alkoxy optionally substituted with 1-3 fluorine, cyclopropoxy, or cyclobutoxy,
n is 1, 2, 3, or 4,
$R^4$ is hydrogen, —CN, —COOH, optionally substituted alkyl (e.g., optionally substituted $C_{1-6}$ alkyl), or optionally substituted carbocyclyl (e.g., optionally substituted $C_{3-6}$ carbocyclyl).

In any of the embodiments herein according to Formula II, $R^5$ can be an optionally substituted aryl, an optionally substituted heteroaryl, an optionally substituted carbocyclyl or optionally substituted heterocyclyl, which is further defined herein.

In some embodiments, the compound of Formula II can be characterized as having a Formula II-1:

Formula II-1

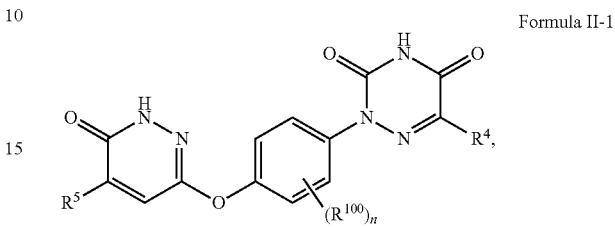

wherein $R^5$, $R^{100}$, n, and $R^4$ are defined herein.

Various cyclic groups are suitable for use as $R^5$ in Formula II (e.g., Formula II-1). In some embodiments, $R^5$ can be an optionally substituted $C_{3-6}$ cycloalkyl, e.g., with one or two substituents independently selected from $C_{1-4}$ alkyl optionally substituted with 1-3 fluorine, —OH, —OPg$^1$, $C_{1-4}$ alkoxy optionally substituted with 1-3 fluorine, and halogen, wherein Pg$^1$ is an oxygen protecting group. In some embodiments, $R^5$ can be cyclopropyl, cyclobutyl, cyclopentyl, or cyclohexyl, each of which can be optionally substituted with 1 or 2 substituents independently selected from F, methyl and hydroxyl.

In some embodiments, $R^5$ can be an optionally substituted 4-7 membered heterocyclyl (e.g., piperidinyl or tetrahydropyranyl), e.g., with one or two substituents independently selected from $C_{1-4}$ alkyl optionally substituted with 1-3 fluorine, —OH, —OPg$^1$, $C_{1-4}$ alkoxy optionally substituted with 1-3 fluorine, —C(O)—$C_{1-4}$ alkyl, —C(O)—O—$C_{1-4}$ alkyl, and halogen, wherein Pg$^1$ is an oxygen protecting group. For example, in some embodiments, $R^5$ can be an optionally substituted 5 or 6 membered saturated heterocyclyl containing one or two heteroatoms, such as one oxygen, one oxygen and one nitrogen, one nitrogen, two nitrogen atoms, etc. In some embodiments, $R^5$ can be piperidinyl or tetrahydropyranyl, which can be optionally substituted, for example, the piperidinyl can in some embodiments be substituted with one nitrogen atom substituent as described herein such as a nitrogen protecting group (e.g., benzyl or substituted benzyl, —C(O)—$C_{1-4}$ alkyl or —C(O)—O—$C_{1-4}$ alkyl, such as acetyl).

In some embodiments, $R^5$ is an optionally substituted phenyl, e.g., with one or more such as 1 or 2 substituents independently selected from $C_{1-4}$ alkyl optionally substituted with 1-3 fluorine, —OH, —OPg$^1$, $C_{1-4}$ alkoxy optionally substituted with 1-3 fluorine, —CN, and halogen, wherein Pg$^1$ is an oxygen protecting group. For example, in some embodiments, $R^5$ can be a phenyl optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkoxy (e.g., methoxy, ethoxy, etc.) optionally substituted with 1-3 fluorine, hydroxyl, and CN.

In some embodiments, $R^5$ can be an optionally substituted 5-10 membered heteroaryl (e.g., as described herein). For example, in some embodiments, $R^5$ can be a 5-10 membered heteroaryl containing 1-3 heteroatoms independently selected from O, N, and S, wherein the heteroaryl is optionally substituted, e.g., with 1-5, such as with one or two substituents independently selected from $C_{1-4}$ alkyl optionally substituted with 1-3 fluorine, $C_{1-4}$ alkyl substituted with one or two hydroxyl groups, —OH, —OPg$^1$, $C_{1-4}$ alkoxy optionally substituted with 1-3 fluorine, —CN, and halogen, wherein Pg$^1$ is an oxygen protecting group. In some embodiments, R$^5$ can be an optionally substituted 5 or 6-membered heteroaryl, e.g., as described herein, such as pyridinyl, pyrazolyl, or isoxazolyl, etc. In some embodiments, R$^5$ can be an optionally substituted 5,6- or 6,6-bicyclic heteroaryl, e.g., as described herein, such as indazolyl, etc.

In some embodiments, R$^5$ can be selected from the following:

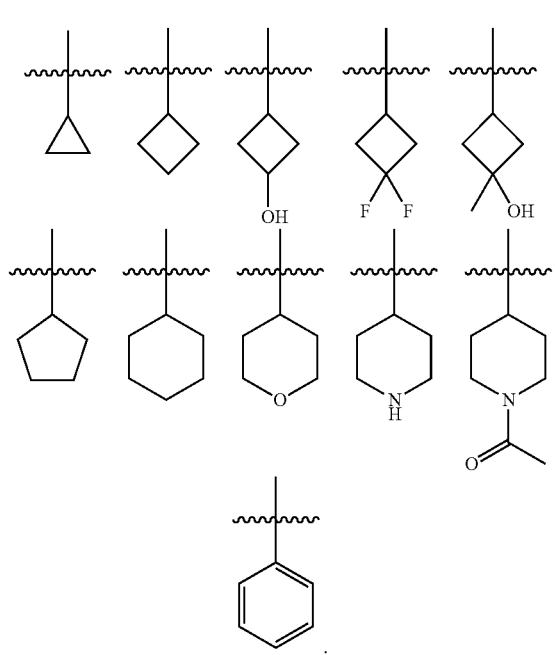

The definitions of A, R$^3$, R$^{100}$, n and R$^4$ suitable for Formula II (e.g., Formula II-1) include any of those described herein in the context of Formula I.

For example, typically, A in Formula II is O or CH$_2$, more preferably, O. In some embodiments, A in Formula II is S. In some embodiments, R$^3$ in Formula II can be hydrogen or an optionally substituted alkyl that can be metabolically converted into a corresponding compound with R$^3$ being hydrogen. For example, in some embodiments, R$^3$ can be a $C_{1-4}$ alkyl, such as a methyl, optionally substituted with one or more groups (such as one) independently selected from —OH, O-linked amino acid, —OP(O)(OH)$_2$, and —OC(O)—R$^{101}$, wherein R$^{101}$ can be an optionally substituted $C_{1-6}$ alkyl, optionally substituted $C_{1-6}$ alkoxy, optionally substituted-$C_{1-6}$ alkylene-COOH, optionally substituted $C_{3-6}$ cycloalkyl, optionally substituted 4-7 membered heterocyclyl, optionally substituted 5-10 membered heteroaryl, or optionally substituted aryl. The phenyl ring in Formula II (e.g., Formula II-1) is also typically substituted with 2 or 3 independently selected R$^{100}$ groups, i.e., n is 2 or 3. In some embodiments, R$^{100}$ at each occurrence is independently F, Cl, Br, CF$_3$, or methyl. In some embodiments, one instance of R$^{100}$ is CF$_3$. In some embodiments, the R$^{100}$ together with the phenyl ring they are attached to form one of the following:

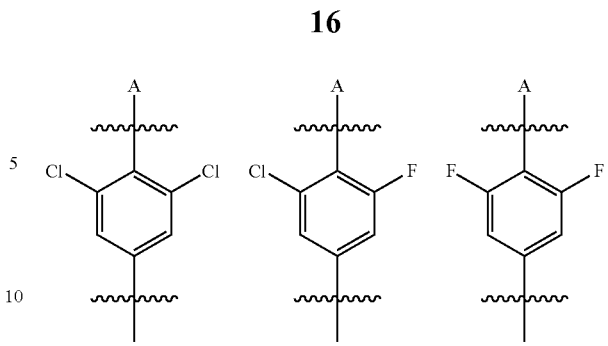

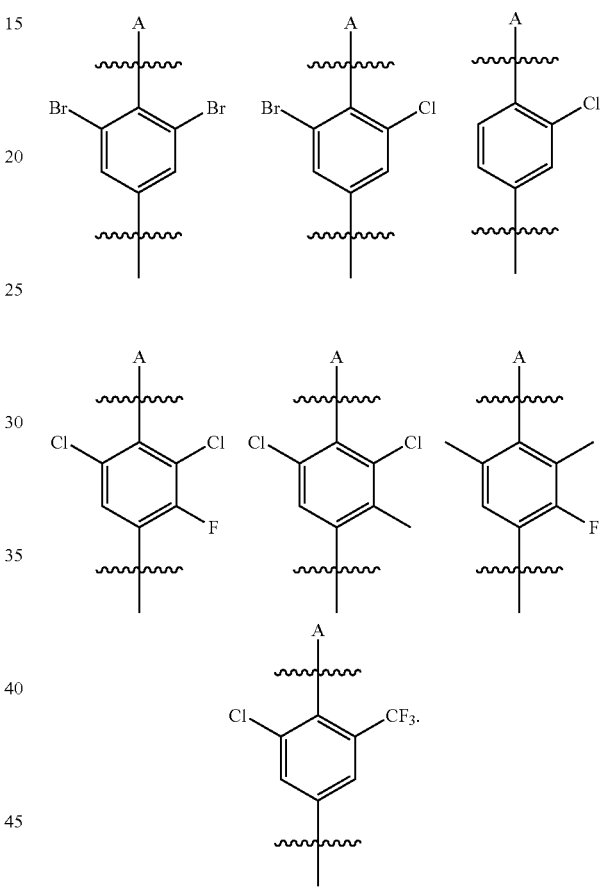

In some embodiments, the R$^{100}$ together with the phenyl ring they are attached to form

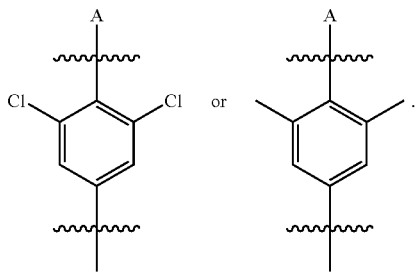

In some embodiments, the R$^{100}$ together with the phenyl ring they are attached to form

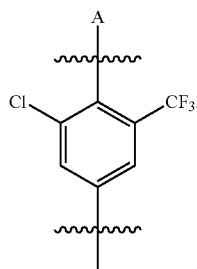

In some embodiments, the substituent $R^4$ at the azauracil ring in Formula II (e.g., Formula II-1) can be $C_{1-6}$ alkyl or $C_{3-6}$ cycloalkyl, each optionally substituted with 1-3 fluorine. In some embodiments, $R^4$ can be hydrogen, —CN, —COOH, methyl, ethyl, cyclopropyl, isopropyl, or propyl. In some preferred embodiments, $R^4$ in Formula II (e.g., Formula II-1) can be hydrogen, —CN or methyl. In some preferred embodiments, $R^4$ in Formula II (e.g., Formula II-1) can be methyl, ethyl, cyclopropyl, isopropyl, or propyl.

Other suitable A, $R^3$, $R^{100}$, n and $R^4$ include any of those described herein.

In some embodiments, the present invention are also directed to TR beta agonists without a pyridazinone structural unit. The inventors have unexpectedly found that various heterocyclic structures can be used to replace the pyridazinone structural unit and achieve similar or better potency. In some embodiments, the present invention provides a compound of Formula III, or a pharmaceutically acceptable salt thereof:

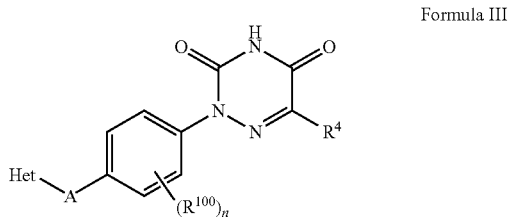

Formula III wherein:

Het is a bicyclic heteroaryl, e.g., 5,6-bicyclic or 6,6-bicyclic heteroaryl, which is substituted with 1-2 substituents independently selected from a nitrogen protecting group, —OH, —OPg$^1$, an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted; wherein Pg$^1$ is an oxygen protecting group, wherein the bicyclic heteroaryl, e.g., 5,6-bicyclic or 6,6-bicyclic heteroaryl is optionally further substituted as valence permits;

A is null, O, CH$_2$, S, SO or SO$_2$, $R^{100}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy, n is 1, 2, 3, or 4, wherein $R^4$ is hydrogen, —CN, —COOH, optionally substituted C$_{1-6}$ alkyl, or optionally substituted C$_{3-6}$ carbocyclyl.

Any of the 5,6-bicyclic or 6,6-bicyclic heteroaryl described herein can be used as Het in Formula III. In some preferred embodiments, the 5,6-bicyclic or 6,6-bicyclic heteroaryl can be selected from indolyl, pyrrolopyridine, and indazolyl. A in Formula III is typically S, O, or CH$_2$. In some embodiments, A is O. In some embodiments, A is S. In some embodiments, A is CH$_2$. However, in cases where a nitrogen atom of the 5,6-bicyclic or 6,6-bicyclic heteroaryl is directly linked to the phenyl group in Formula III, then A is understood as null.

In some embodiments, the Het in Formula III is indolyl. For example, in some embodiments, the present invention provides a compound of Formula III-1, or a pharmaceutically acceptable salt thereof:

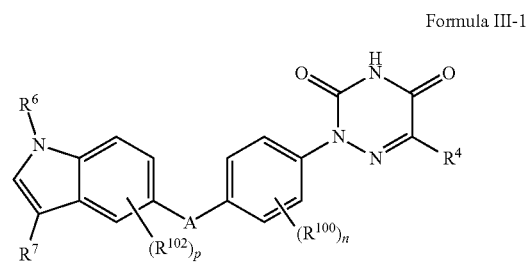

Formula III-1 wherein:

$R^6$ is hydrogen or a nitrogen protecting group, $R^7$ is an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted;

A is O, CH$_2$, S, SO or SO$_2$, each of $R^{100}$ and $R^{m2}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy, n is 1, 2, 3, or 4, p is 0, 1, 2, 3, or 4, $R^4$ is hydrogen, —CN, —COOH, optionally substituted C$_{1-6}$ alkyl, or optionally substituted C$_{3-6}$ carbocyclyl.

In some embodiments, the compound of Formula III-1 can be characterized as having a Formula III-1A:

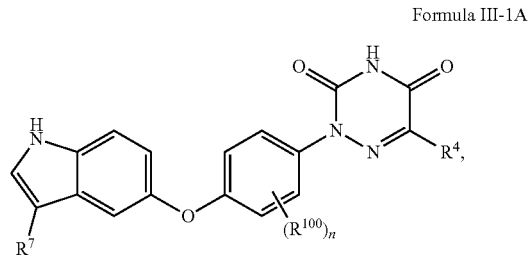

Formula III-1A wherein $R^7$, $R^{100}$, n, and $R^4$ are defined herein.

In some embodiments, the Het in Formula III is a pyrrolopyridine. For example, in some embodiments, the present invention provides a compound of Formula III-2, or a pharmaceutically acceptable salt thereof:

Formula III-2

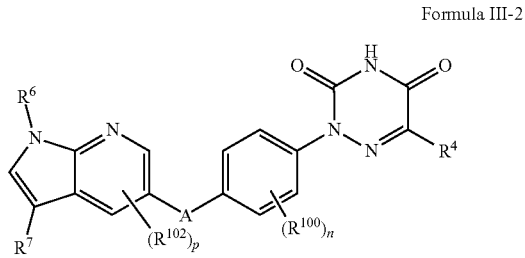

wherein:
R$^6$ is hydrogen or a nitrogen protecting group,
R$^7$ is an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted;
A is O, CH$_2$, S, SO or SO$_2$,
each of R$^{100}$ and R$^{102}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy,
n is 1, 2, 3, or 4,
p is 0, 1, 2, or 3,
R$^4$ is hydrogen, —CN, —COOH, optionally substituted C$_{1-6}$ alkyl, or optionally substituted C$_{3-6}$ carbocyclyl.

In some embodiments, the compound of Formula III-2 can be characterized as having a Formula III-2A:

Formula III-2A

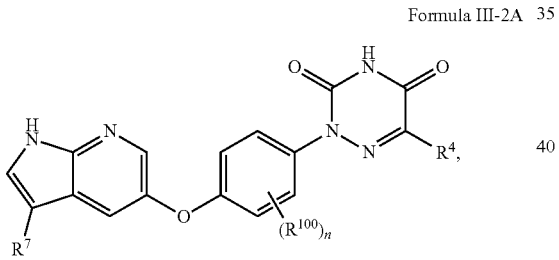

wherein R$^7$, R$^{100}$, n, and R$^4$ are defined herein.

In some embodiments, the Het in Formula III is indazolyl. For example, in some embodiments, the present invention provides a compound of Formula III-3, or a pharmaceutically acceptable salt thereof:

Formula III-3

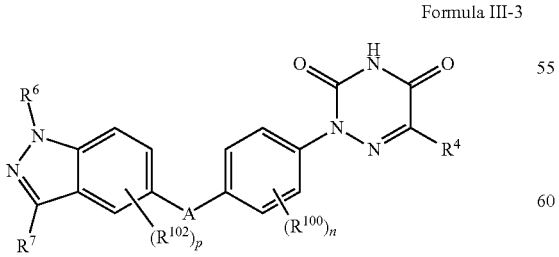

wherein:
R$^6$ is hydrogen or a nitrogen protecting group,
R$^7$ is an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted;
A is O, CH$_2$, S, SO or SO$_2$,
each of R$^{100}$ and R$^{102}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy,
n is 1, 2, 3, or 4,
p is 0, 1, 2, or 3,
R$^4$ is hydrogen, —CN, —COOH, optionally substituted C$_{1-6}$ alkyl, or optionally substituted C$_{3-6}$ carbocyclyl.

In some embodiments, the compound of Formula III-3 can be characterized as having a Formula III-3A:

Formula III-3A

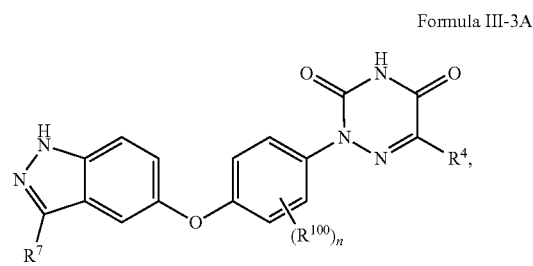

wherein R$^7$, R$^{100}$, n, and R$^4$ are defined herein.

In some embodiments, the Het in Formula III is indazolyl which is connected to the phenyl group directly, i.e., A is null. For example, in some embodiments, the present invention provides a compound of Formula III-4, or a pharmaceutically acceptable salt thereof:

Formula III-4

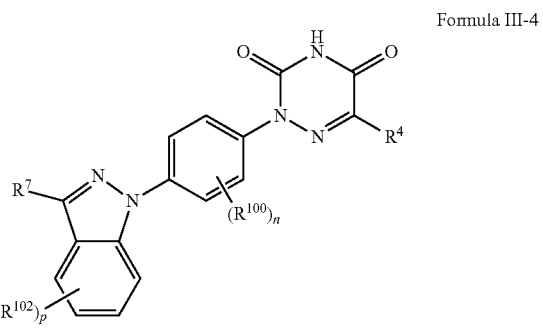

wherein:
R$^7$ is an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted;
R$^{102}$ at each occurrence is independently —OH, —OPg$^1$, F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy, wherein Pg$^1$ is an oxygen protecting group, $R^{100}$ at each occurrence is independently F, Cl, Br, I, $C_{1-4}$ alkyl optionally substituted with 1-3 fluorine, cyclopropyl, cyclobutyl, $C_{1-4}$ alkoxy optionally substituted with 1-3 fluorine, cyclopropoxy, or cyclobutoxy, n is 1, 2, 3, or 4, p is 0, 1, 2, 3, or 4, $R^4$ is hydrogen, —CN, —COOH, optionally substituted $C_{1-6}$ alkyl, or optionally substituted $C_{3-6}$ carbocyclyl.

In some embodiments, the compound of Formula III-4 can be characterized as having a Formula III-4A:

Formula III-4A

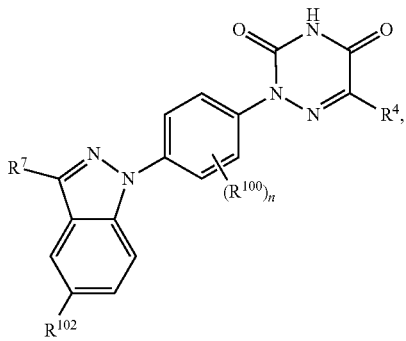

wherein $R^{102}$ is OH or O—$Pg^1$, and $R^7$, $R^{100}$, n, and $R^4$ are defined herein.

A in Formula III-1 to III-3 is typically S, O or $CH_2$. For example, in some embodiments, A is S. In some embodiments, A is O. In some embodiments, A is $CH_2$.

In some embodiments, the indole ring in Formula III-1 is not further substituted, i.e., p is 0. However, in some embodiments, the indole ring can also be further substituted with up to 4 substituents. The $(R^{102})_p$ in Formula III-1 should be understood as encompassing substitution at any of the available positions in the indole ring, including the 2-position, not just the benzene portion of the indole ring. In some embodiments, each substituent of $R^{102}$ can be independently selected, for example, from F, Cl, methyl, $CF_3$, cyclopropyl, cyclobutyl, methoxy, cyclopropoxy, and cyclobutoxy.

In some embodiments, the pyrrolopyridine ring in Formula III-2 is not further substituted, i.e., p is 0. However, in some embodiments, the pyrrolopyridine ring can also be further substituted with up to 3 substituents. The $(R^{102})_p$ in Formula III-2 should be understood as encompassing substitution at any of the available positions in the pyrrolopyridine ring, not limiting to the pyridine ring. In some embodiments, each substituent of $R^{102}$ can be independently selected, for example, from F, Cl, methyl, $CF_3$, cyclopropyl, cyclobutyl, methoxy, cyclopropoxy, and cyclobutoxy.

In some embodiments, the indazole ring in Formula III-3 is not further substituted, i.e., p is 0. However, in some embodiments, the indazole ring can also be further substituted with up to 3 substituents. In some embodiments, each substituent of $R^{102}$ can be independently selected, for example, from F, Cl, methyl, $CF_3$, cyclopropyl, cyclobutyl, methoxy, cyclopropoxy, and cyclobutoxy.

The indazole ring in Formula III-4 is typically further substituted, for example, with p being 1. In some embodiments, at least one instance of $R^{102}$ in Formula III-4 is hydroxyl or a protected hydroxyl group (i.e., O-$Pg^1$). In some embodiments, the indazole ring can be further substituted with up to 3 substituents, which can be independently selected, for example, from F, Cl, methyl, $CF_3$, cyclopropyl, cyclobutyl, methoxy, cyclopropoxy, and cyclobutoxy.

$R^6$ in Formula III-1 to III-3 is typically hydrogen. However, in some embodiments, $R^6$ can be a nitrogen protecting group that can be deprotected either in vitro or in vivo (metabolically cleaved) to provide a corresponding compound with $R^6$ being hydrogen. For example, in some embodiments, $R^6$ can be a —C(O)—$C_{1-4}$ alkyl or —C(O)—O—$C_{1-4}$ alkyl. Suitable nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Various acyclic and cyclic groups are suitable for $R^7$ in Formula III-1 to III-4 (including subformula as applicable). In some embodiments, $R^7$ can be isopropyl or an optionally substituted $C_{3-6}$ cycloalkyl, e.g., with one or two substituents independently selected from $C_{1-4}$ alkyl optionally substituted with 1-3 fluorine, —OH, —O$Pg^1$, $C_{1-4}$ alkoxy optionally substituted with 1-3 fluorine, and halogen, wherein $Pg^1$ is an oxygen protecting group. In some embodiments, $R^7$ is —$CONH_2$, —CONH($C_{1-4}$ alkyl), or —CON($C_{1-4}$ alkyl)($C_{1-4}$ alkyl), wherein each of the $C_{1-4}$ alkyl is independently selected and optionally substituted, e.g., with one or two substituents independently selected from $C_{1-4}$ alkyl optionally substituted with 1-3 fluorine, —OH, —O$Pg^1$, $C_{1-4}$ alkoxy optionally substituted with 1-3 fluorine, and halogen, wherein $Pg^1$ is an oxygen protecting group. In some embodiments, $R^7$ can be an optionally substituted 4-7 membered heterocyclyl (e.g., piperidinyl or tetrahydropyranyl), e.g., with one or two substituents independently selected from $C_{1-4}$ alkyl optionally substituted with 1-3 fluorine, —OH, —O$Pg^1$, $C_{1-4}$ alkoxy optionally substituted with 1-3 fluorine, and halogen, wherein $Pg^1$ is an oxygen protecting group. In some embodiments, $R^7$ in Formula III-1 to III-4 (including subformula as applicable) can be a moiety —$CR^1R^1'R^2$ as defined for Formula I or $R^5$ as defined for Formula II, including applicable subformula, see e.g., hereinabove.

Non-limiting exemplary useful groups for $R^7$ in Formula III-1 to III-4 (including subformula as applicable) include (1) $C_{1-6}$ alkyls such as isopropyl; (2) $C_{3-6}$ cycloalkyls such as cyclopropyl, cyclobutyl, cyclopentyl, or cyclohexyl, each of which can be optionally substituted with 1 or 2 substituents independently selected from F, methyl and hydroxyl; (3) phenyl, or 5 or 6 membered heteroaryl (e.g., as described herein, such as pyridyl, pyrrazolyl, isoxazolyl, etc.), each optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkoxy (e.g., methoxy, ethoxy, etc.) optionally substituted with 1-3 fluorine, hydroxyl, and CN; (4) $C_{1-4}$ alkyl (e.g., methyl) substituted with one $C_{3-6}$ cycloalkyl group, 4-7 membered heterocyclic group, 5 or 6 membered heteroaryl group (e.g., as described herein, such as pyridyl, pyrrazolyl, isoxazolyl, etc.), or phenyl group, each of the cycloalkyl, heterocyclic, heteroaryl, or phenyl is optionally substituted with 1-5 (e.g., 1, 2, or 3) substituents independently selected from F, Cl, Br, $C_{1-4}$ alkyl (e.g., methyl, ethyl, propyl, isopropyl, etc.) optionally substituted with 1-3 fluorine, $C_{1-4}$ alkoxy (e.g., methoxy, ethoxy, etc.) optionally substituted with 1-3 fluorine, hydroxyl, and CN; and (5) 4-7 membered heterocyclyl (e.g., piperidinyl or tetrahydropyranyl), which can be optionally substituted, for example, the piperidinyl can be in some embodiments be substituted with one nitrogen atom substituent as described herein such as a nitrogen protecting group.

The definitions of $R^{100}$, n and $R^4$ suitable for Formula III (e.g., Formula III-1 to III-4, including any applicable subformula) include any of those described herein in the context of Formula I or II.

For example, typically, the phenyl ring (not the indole ring) in Formula III (e.g., Formula III-1 to III-4) is also typically substituted with 2 or 3 independently selected $R^{100}$ groups, i.e., n is 2 or 3. In some embodiments, $R^{100}$ at each occurrence is independently F, Cl, Br, $CF_3$, or methyl. In some embodiments, one instance of $R^{100}$ is $CF_3$. In some embodiments, the $R^{100}$ together with the phenyl ring they are attached to form one of the following:

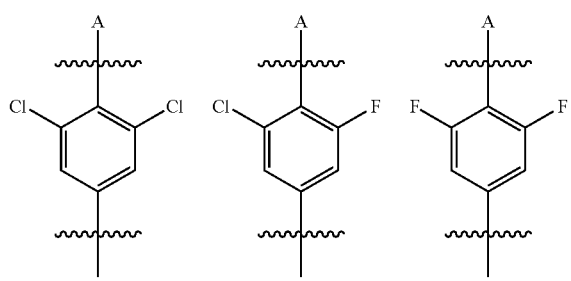

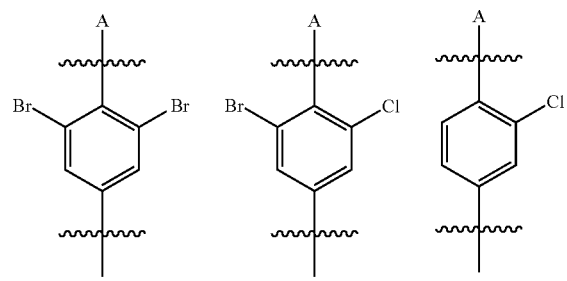

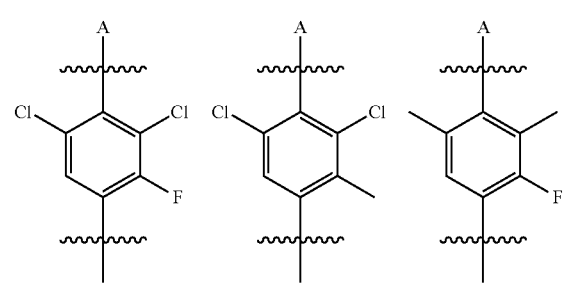

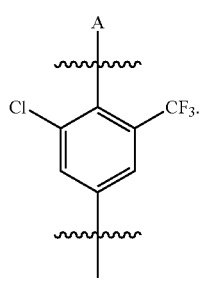

In some embodiments, the $R^{100}$ together with the phenyl ring they are attached to form

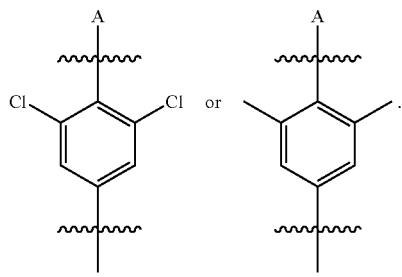

In some embodiments, the $R^{100}$ together with the phenyl ring they are attached to form

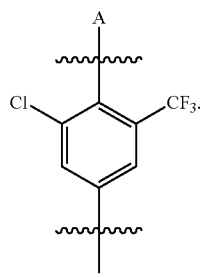

In some embodiments, the substituent $R^4$ at the azauracil ring in Formula III (e.g., Formula III-1 to Formula III-4) can be $C_{1-6}$ alkyl or $C_{3-6}$ cycloalkyl, each optionally substituted with 1-3 fluorine. In some embodiments, $R^4$ can be hydrogen, —CN, —COOH, methyl, ethyl, cyclopropyl, isopropyl, or propyl. In some preferred embodiments, $R^4$ in Formula III (e.g., Formula III-1 to III-4) can be hydrogen, —CN or methyl. In some preferred embodiments, $R^4$ in Formula III (e.g., Formula III-1 to III-4) can be methyl, ethyl, cyclopropyl, isopropyl, or propyl.

Other suitable A, $R^{100}$, n and $R^4$ include any of those described herein.

In some embodiments, the present invention also provides a compound that does not contain an azauracil unit, but instead has a phosphoric acid or ester thereof. For example, in some embodiments, the present invention provides a compound of Formula I-X or II-X, or a pharmaceutically acceptable salt or ester thereof:

Formula I-X

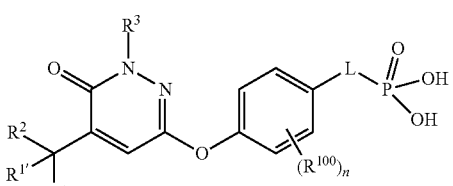

Formula II-X

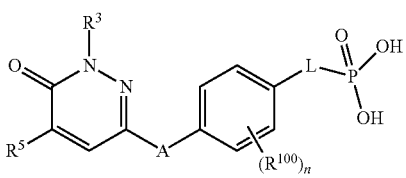

wherein:
R$^1$ and R$^{1'}$ are each independently hydrogen, OH, halogen (e.g., F), or an optionally substituted C$_{1-4}$ alkyl (e.g., C$_{1-4}$ alkyl), or R$^1$ and R$^{1'}$ together form an oxo (=O),
R$^2$ is an optionally substituted alkyl, an optionally substituted carbocyclyl, an optionally substituted heterocyclyl, an optionally substituted aryl, or an optionally substituted heteroaryl, or R$^2$ is —COOH or an ester thereof, —CONH$_2$, —CONH(C$_{1-6}$ alkyl), —CON(C$_{1-6}$ alkyl)(C$_{1-6}$ alkyl), wherein each of the C$_{1-6}$ alkyl is independently selected and optionally substituted,
A is O, CH$_2$, S, SO or SO$_2$,
R$^3$ is hydrogen or an optionally substituted alkyl,
R$^5$ is an optionally substituted aryl, an optionally substituted heteroaryl, an optionally substituted carbocyclyl or optionally substituted heterocyclyl, or R$^5$ is —COOH or an ester thereof, —CONH$_2$, —CONH (C$_{1-6}$ alkyl), —CON(C$_{1-6}$ alkyl)(C$_{1-6}$ alkyl), wherein each of the C$_{1-6}$ alkyl is independently selected and optionally substituted,
R$^{100}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy,
n is 1, 2, 3, or 4,
L is J$^1$-J$^2$-J$^3$, wherein each of J$^1$, J$^2$, and J$^3$ is independently null, O, NH, or an optionally substituted C$_{1-6}$ alkylene, provided that at least one of J$^1$, J$^2$, and J$^3$ is an optionally substituted C$_{1-6}$ alkylene, and L does not contain an O—O or O—N bond.

In some embodiments, L is C$_{1-4}$ alkylene or —O—C$_{1-4}$ alkylene, for example, L is ethylene or —O—CH$_2$—, wherein the CH$_2$ is linked to the phosphine atom.

In some embodiments, an ester, including monoester or diester, of the compound having Formula I-X or II-X is provided, such as a pharmaceutically acceptable ester. For example, in some embodiments, the present invention provides an ethyl ester (such as diethyl ester) of the compound having Formula I-X or II-X. In some embodiments, the ester can be a cyclic ester, which can be derived from a diol such as a 1,2-diol or 1,3-diol.

Further definitions of R$^1$, R$^{1'}$, R$^2$, R$^3$, R$^5$, A, R$^{100}$, and n suitable for Formula I-X or II-X include any of those described and/or preferred herein in the context of Formula I or II, as applicable.

In some embodiments, the present invention provides a compound of Formula III-X, or a pharmaceutically acceptable salt or ester thereof:

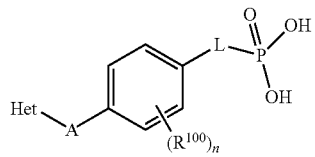

Formula III-X wherein:
Het is a bicyclic heteroaryl, e.g., 5,6-bicyclic or 6,6-bicyclic heteroaryl, which is substituted with 1-2 substituents independently selected from a nitrogen protecting group, —OH, —OPg$^1$, an optionally substituted alkyl, —COOH or an ester thereof, —CONH$_2$, —CONH(C$_{1-6}$ alkyl), —CON(C$_{1-6}$alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted; wherein Pg$^1$ is an oxygen protecting group, wherein the bicyclic heteroaryl, e.g., 5,6-bicyclic or 6,6-bicyclic heteroaryl is optionally further substituted as valence permits;
A is null, O, CH$_2$, S, SO or SO$_2$,
R$^{100}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy,
n is 1, 2, 3, or 4,
wherein L is J$^1$-J$^2$-J$^3$, wherein each of J$^1$, J$^2$, and J$^3$ is independently null, O, NH, or an optionally substituted C$_{1-6}$ alkylene, provided that at least one of J$^1$, J$^2$, and J$^3$ is an optionally substituted C$_{1-6}$ alkylene, and L does not contain an O—O or O—N bond.

In some embodiments, L is C$_{1-4}$ alkylene or —O—C$_{1-4}$ alkylene, for example, L is ethylene or —O—CH$_2$—, wherein the CH$_2$ is linked to the phosphine atom.

In some embodiments, an ester, including monoester or diester, of the compound having Formula III-X is provided, such as a pharmaceutically acceptable ester. For example, in some embodiments, the present invention provides an ethyl ester (such as diethyl ester) of the compound having Formula III-X. In some embodiments, the ester can be a cyclic ester, which can be derived from a diol such as a 1,2-diol or 1,3-diol.

Further definitions of Het, A, R$^{100}$, and n suitable for Formula III-X include any of those described and/or preferred herein in the context of Formula III-1, III-2, III-3, or III-4, as applicable.

In some specific embodiments, the present invention provides a compound selected from Compound Nos. 1-99, or a pharmaceutically acceptable salt thereof:

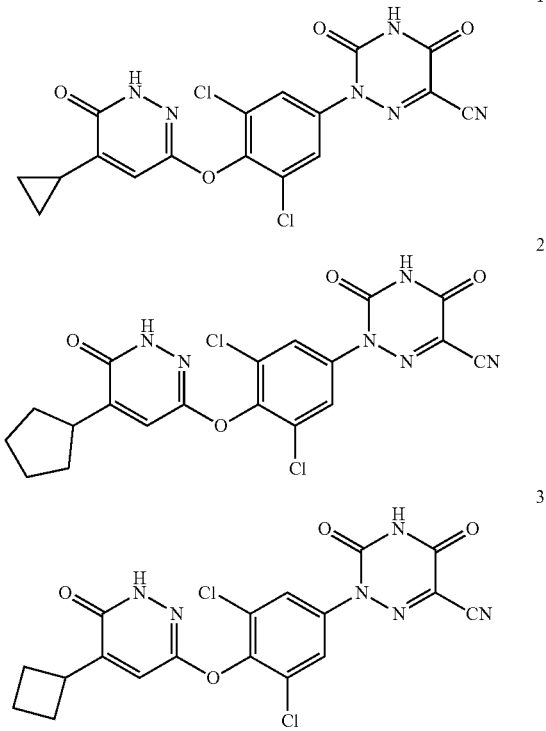

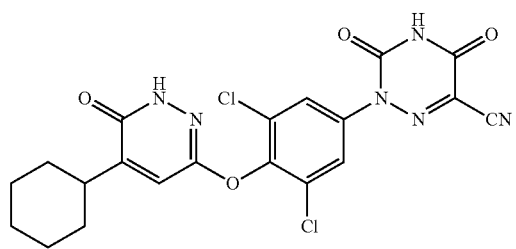
4
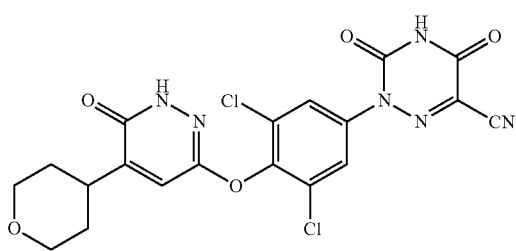
5
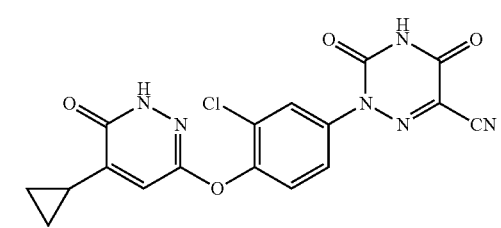
6
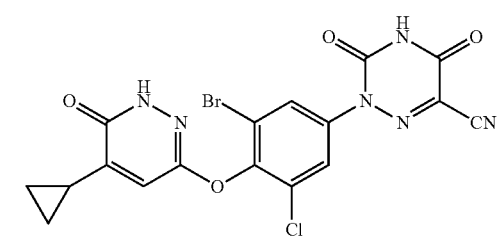
7
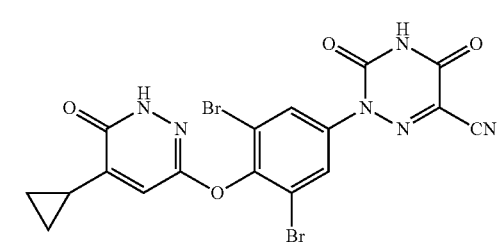
8
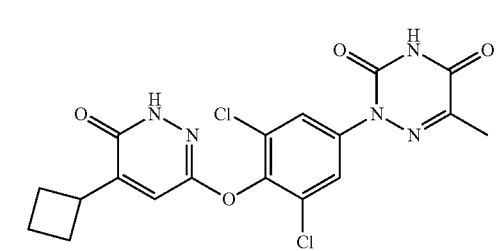
9
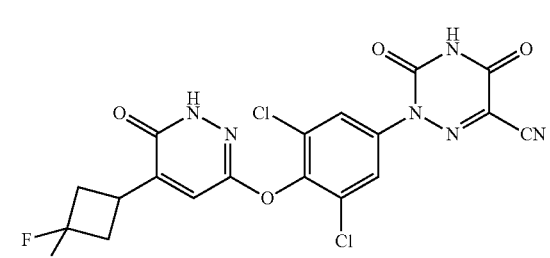
10
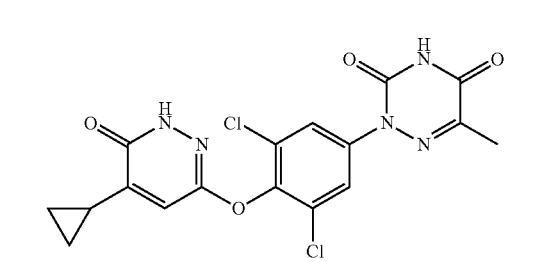
11
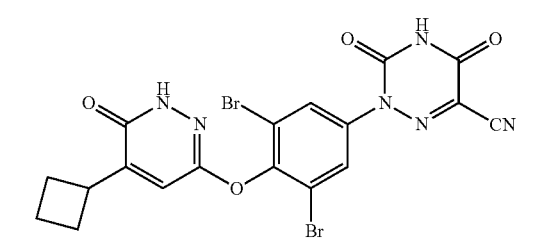
12
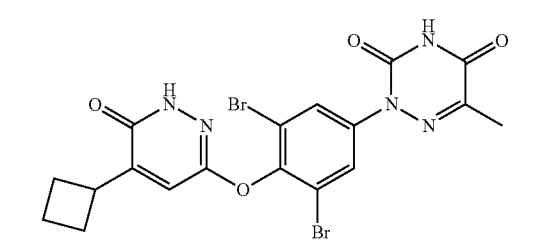
13
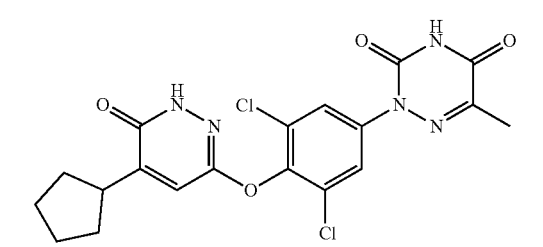
14
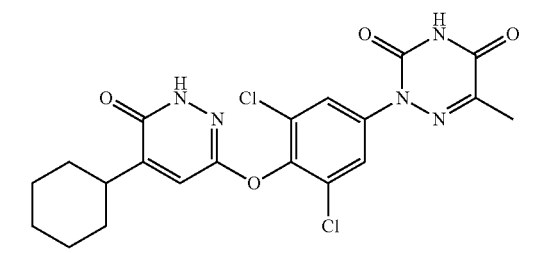
15

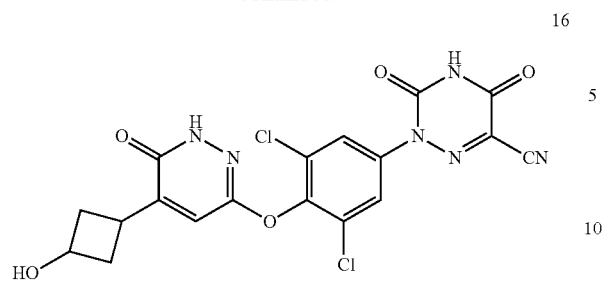
16
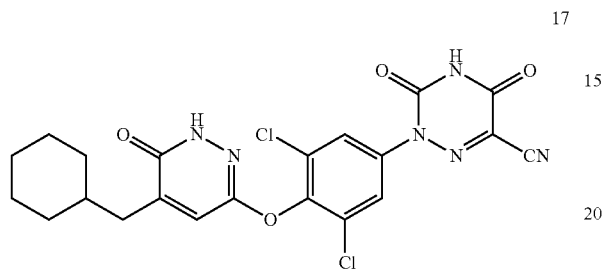
17
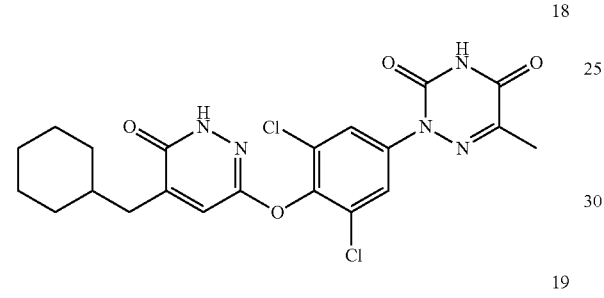
18
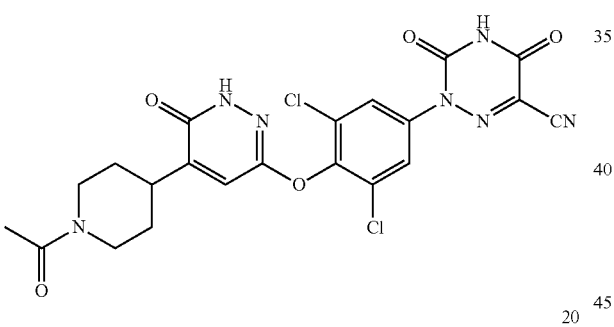
19
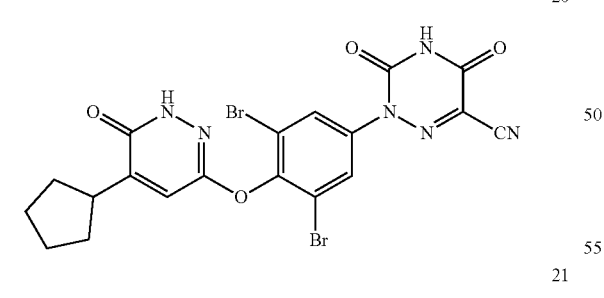
20
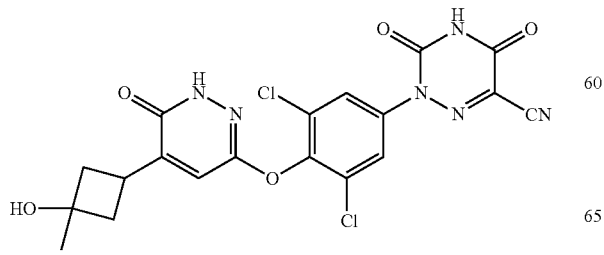
21
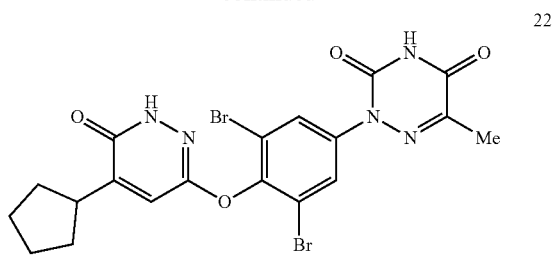
22
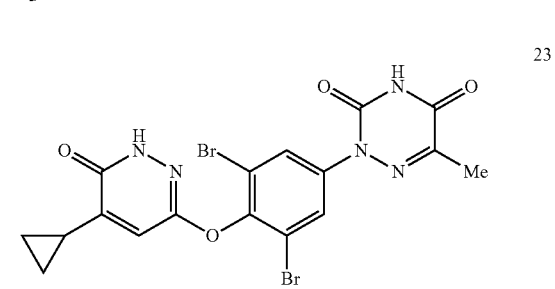
23
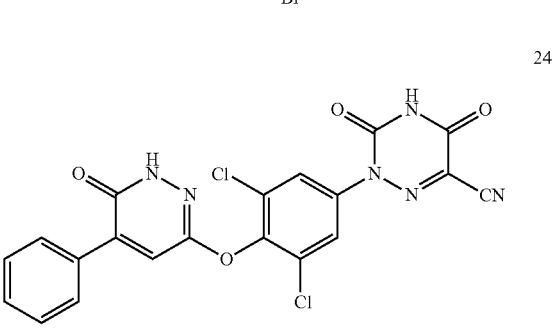
24
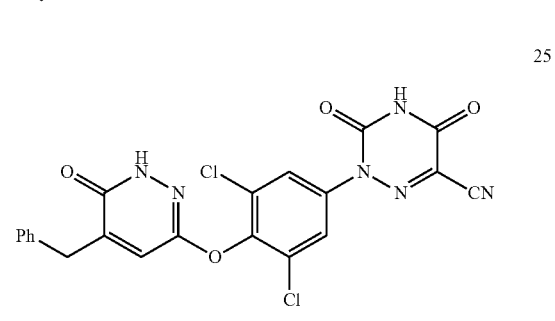
25
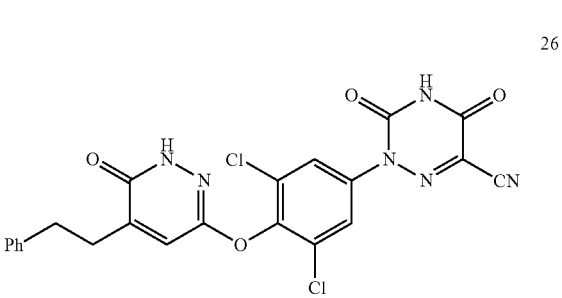
26
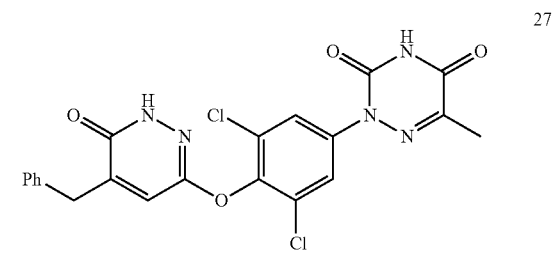
27

-continued
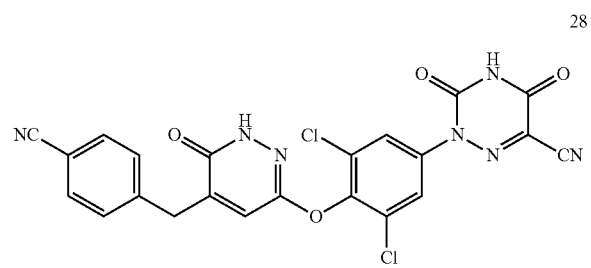
28
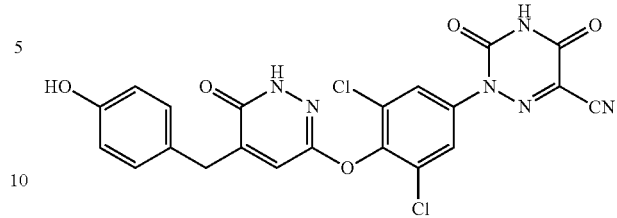
33
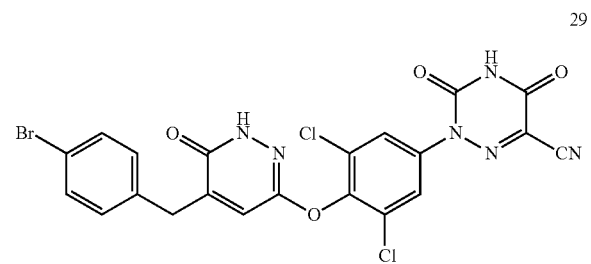
29
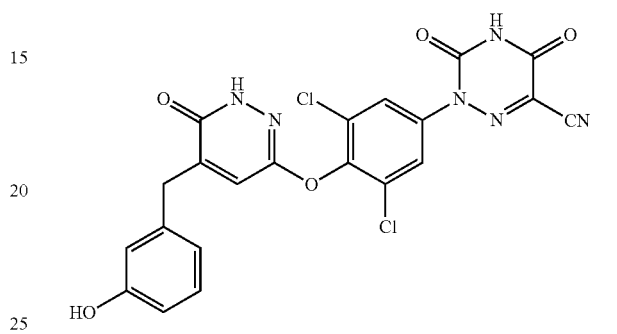
34
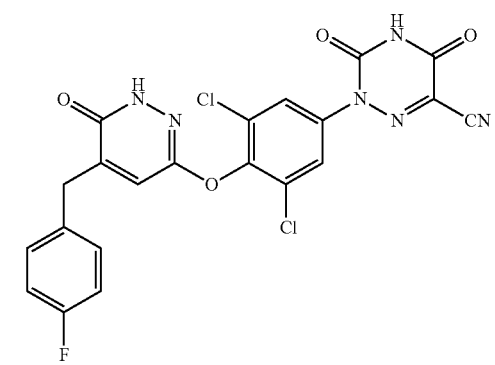
30
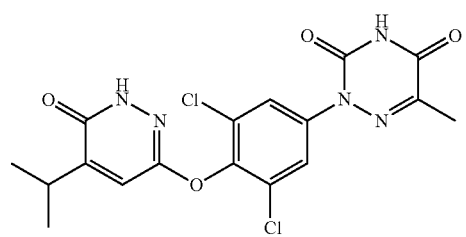
35
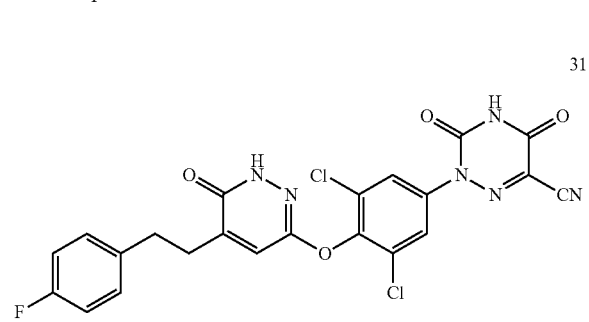
31
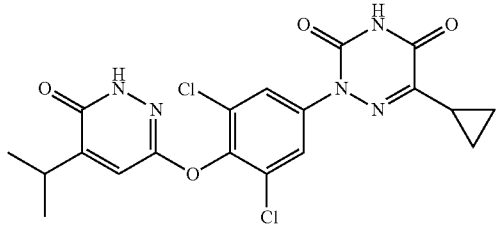
36
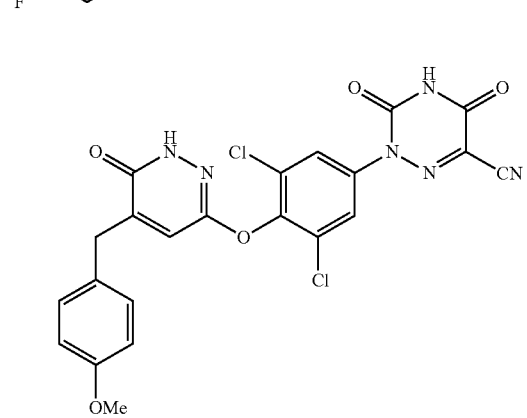
32
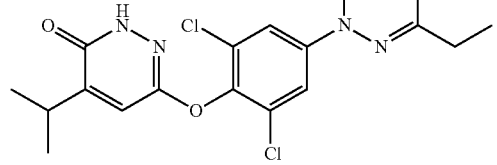
37
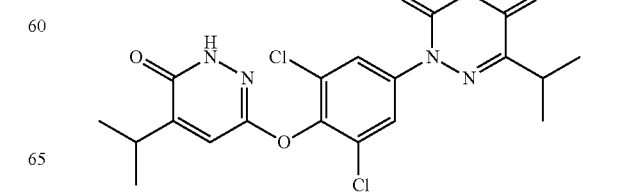
38

39
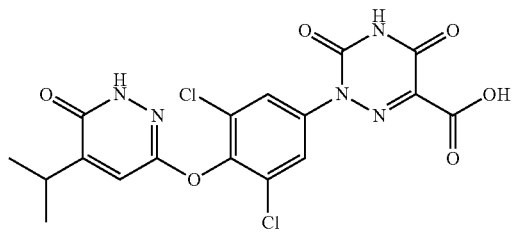
40
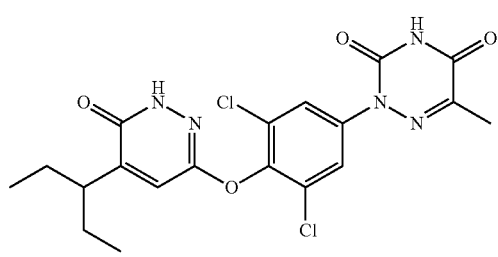
41
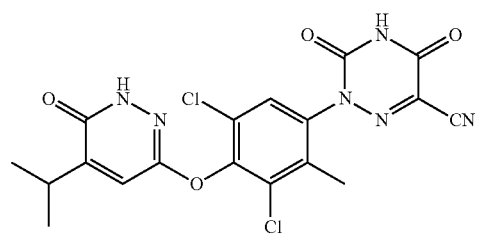
42
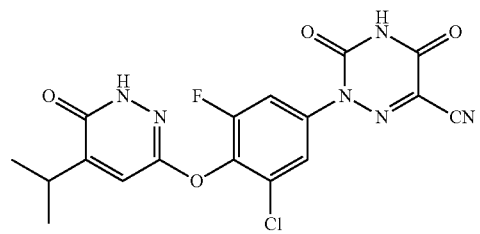
43
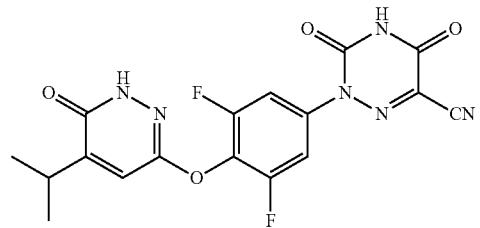
44
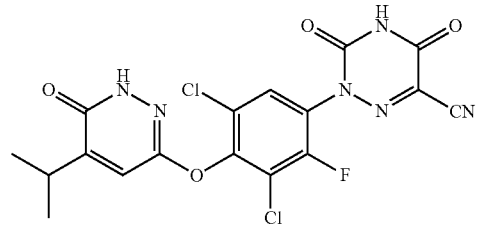
45
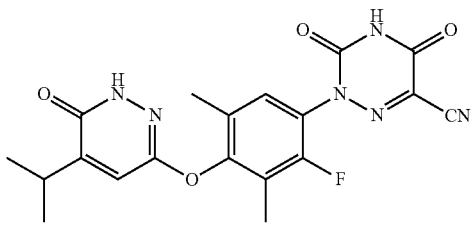
46
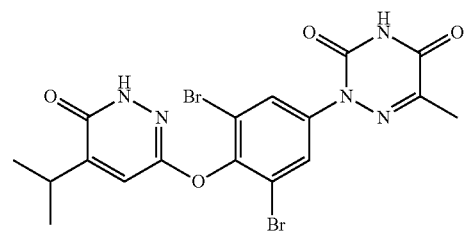
47
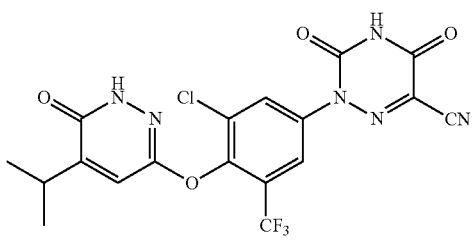
48
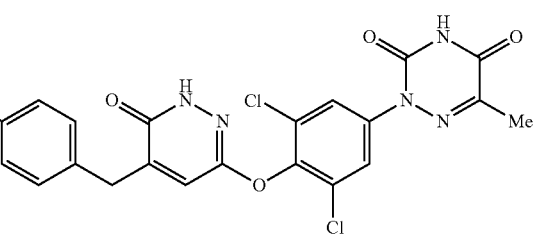
49
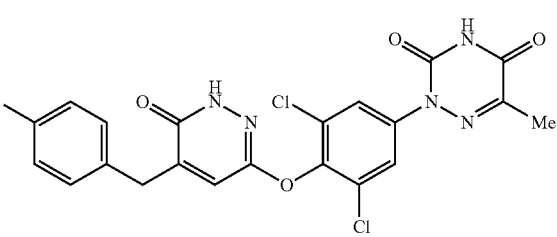
50
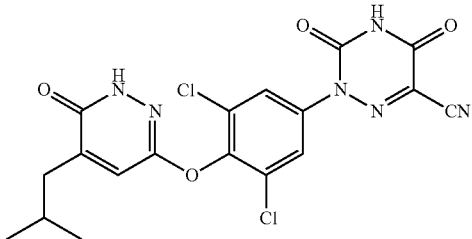

51
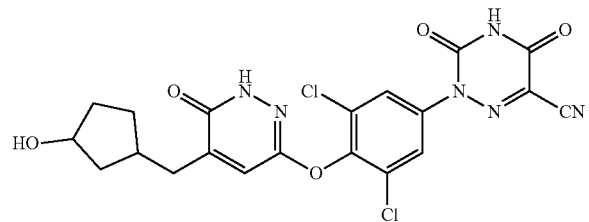
56
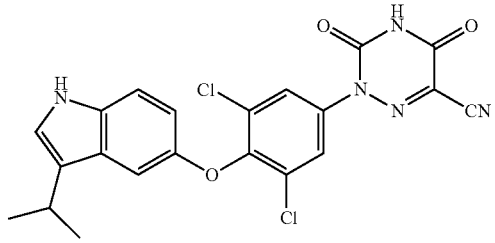
52
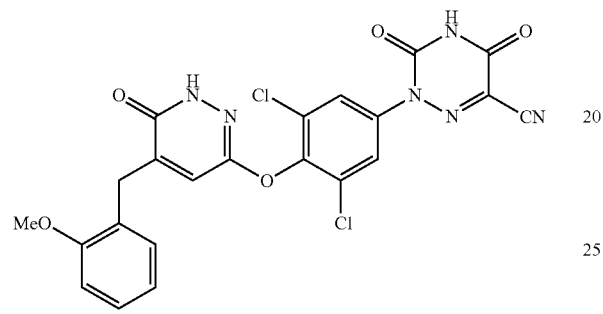
57
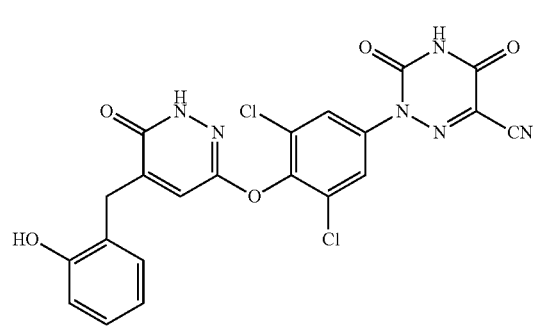
53
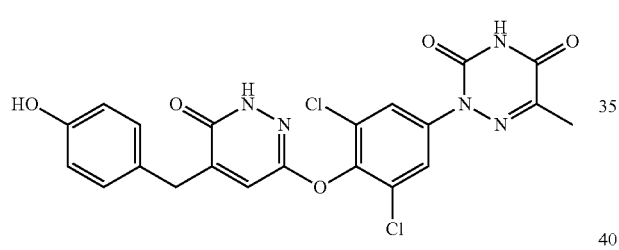
58
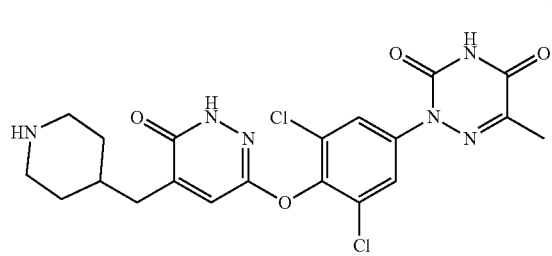
54
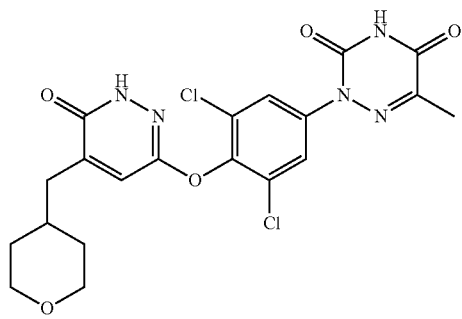
59
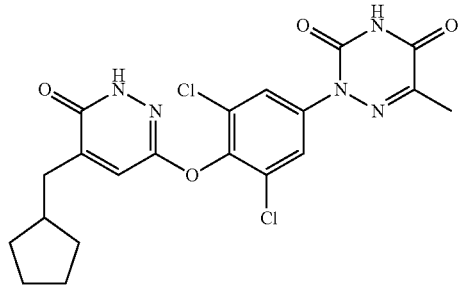
55
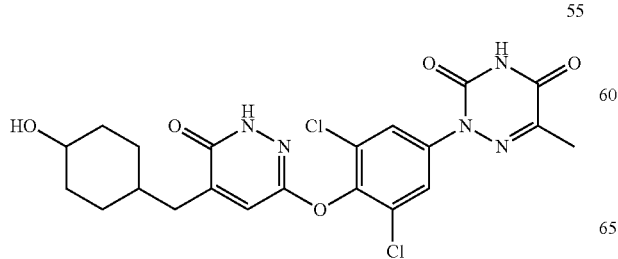
60
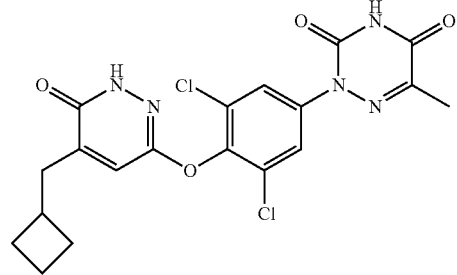

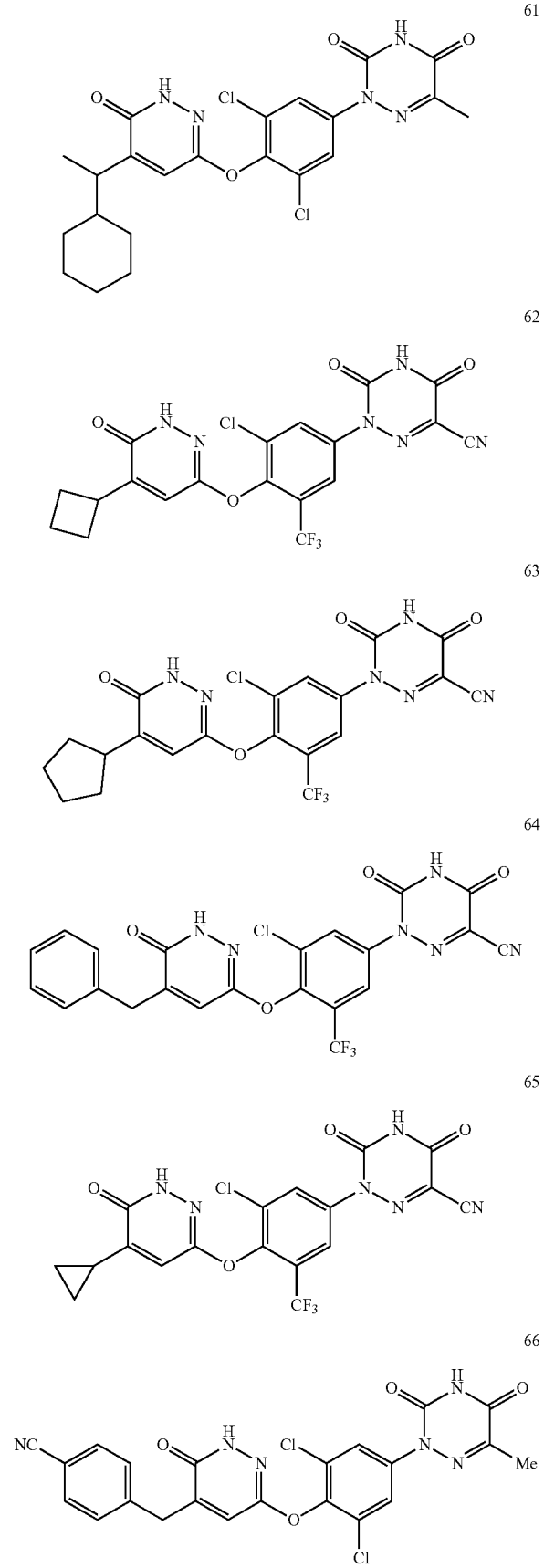
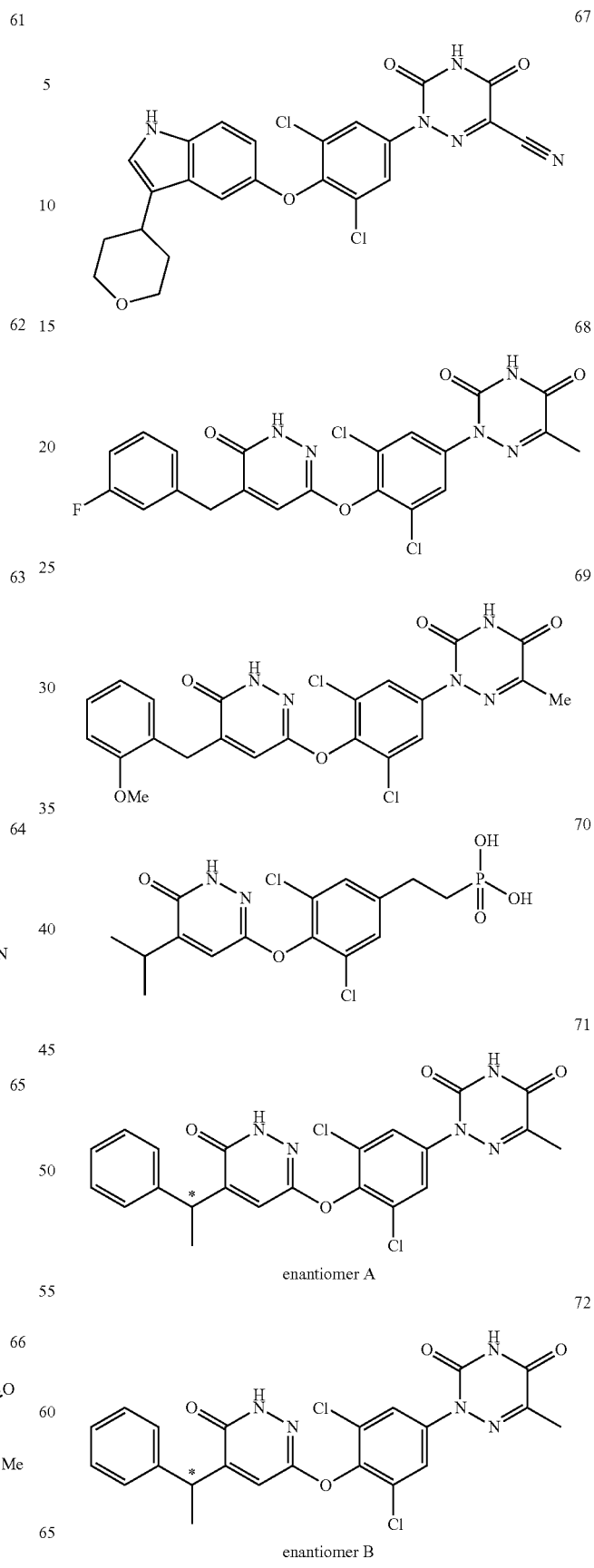

73
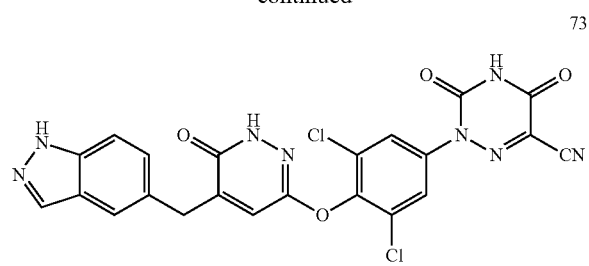
74
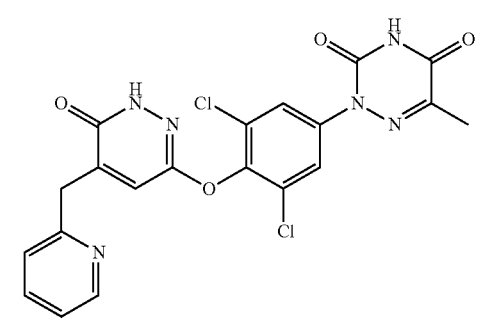
75
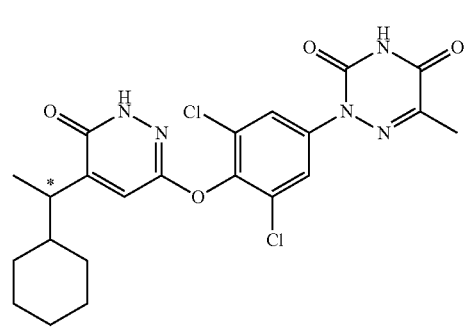
enantiomer A
76
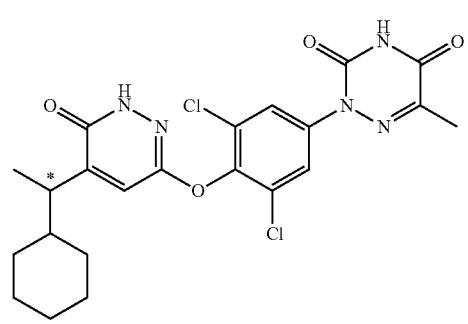
enantiomer B
77
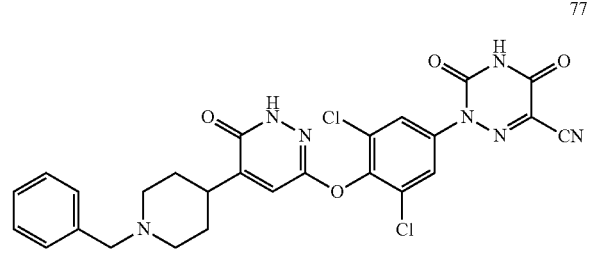
78
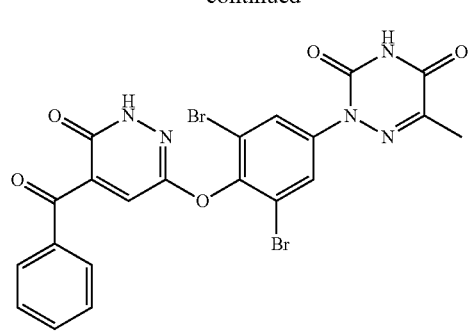
79
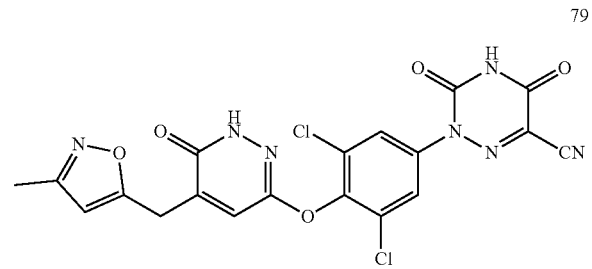
80
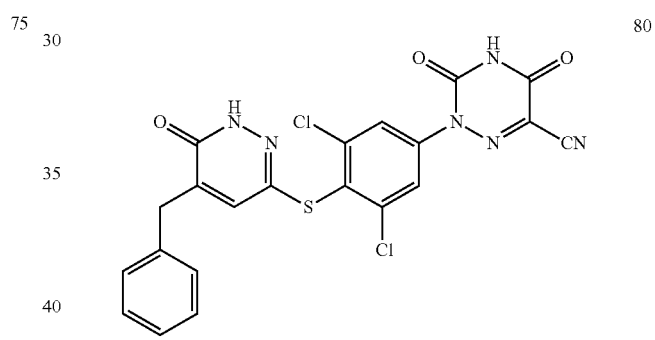
81
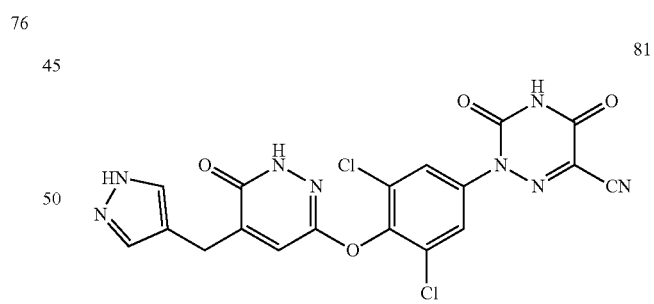
82
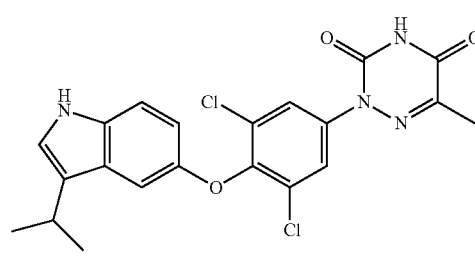

83
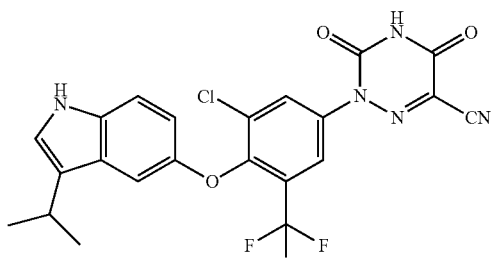
84
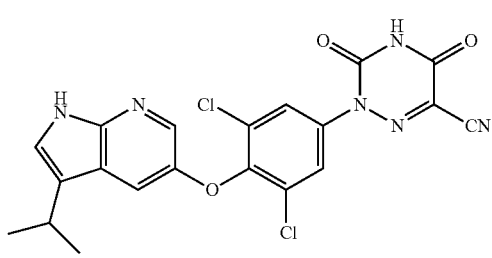
85
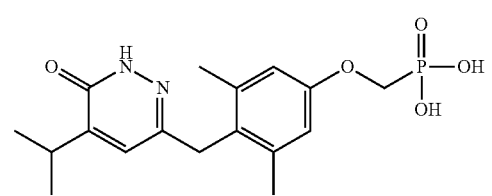
86
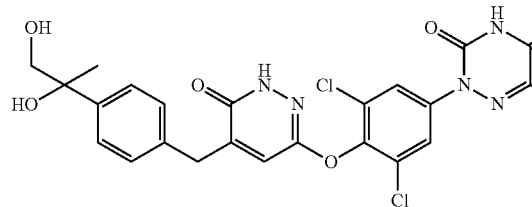
87
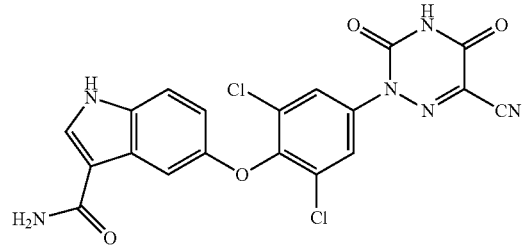
88
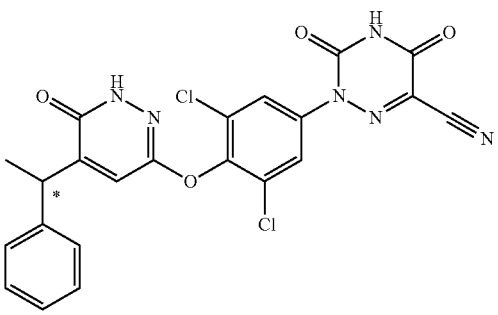
enantiomer A
89
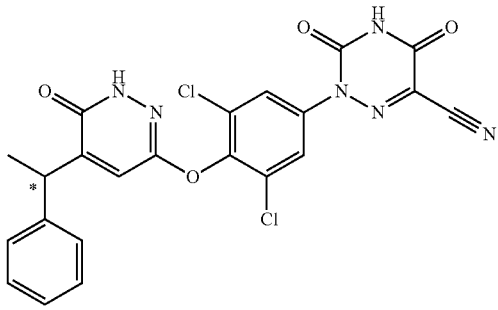
enantiomer B
90
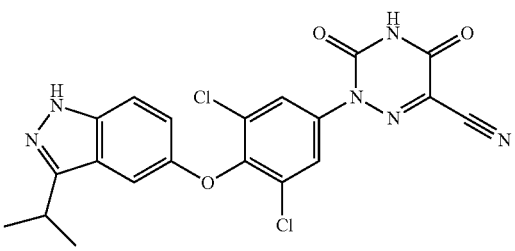
91
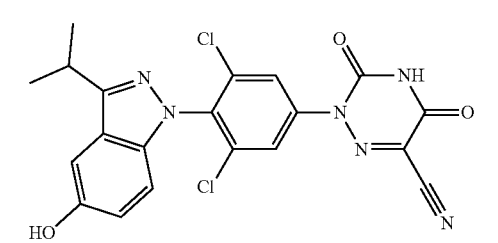
92
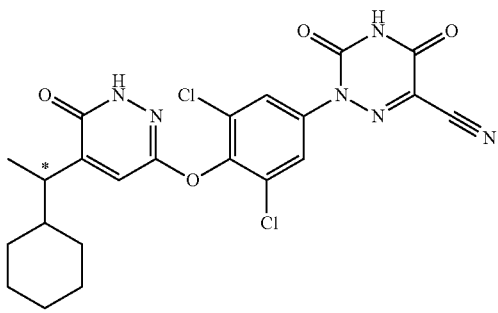
enantiomer A
93
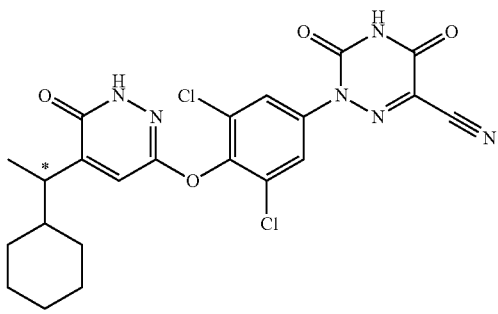
enantiomer B

94

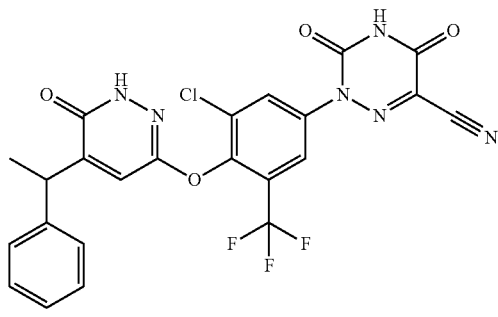

racemate

95

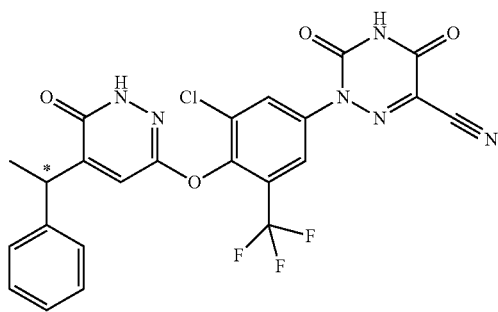

enantiomer A

96

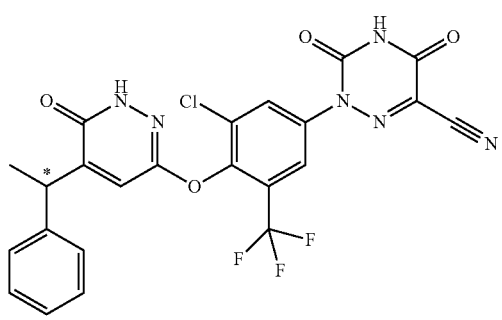

enantiomer B

97

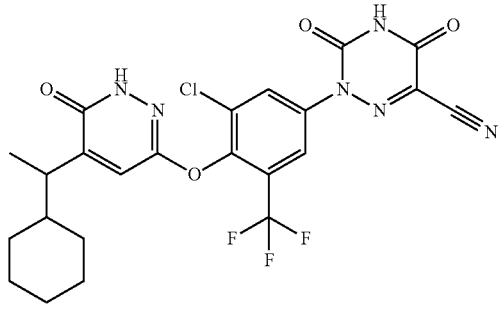

racemate

98

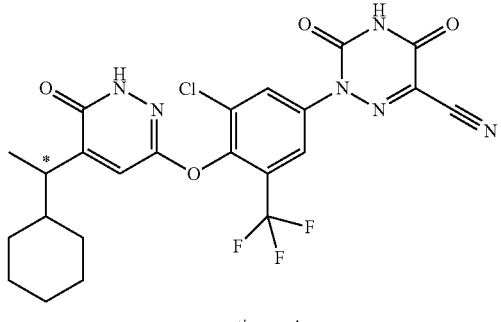

enantiomer A

99

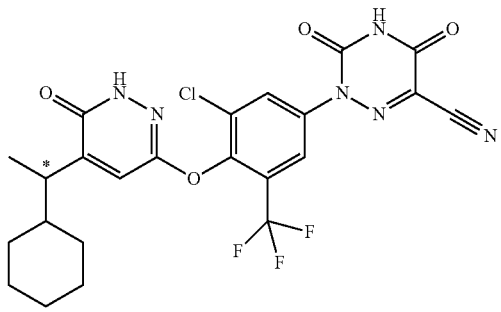

enantiomer B

Method of Synthesis

The compounds of the present disclosure can be readily synthesized by those skilled in the art in view of the present disclosure. Exemplified synthesis are also shown in the Examples section.

The following synthetic processes for Formula I-2 are illustrative, which can be applied similarly by those skilled in the art for the synthesis of other compounds of Formula I, II, and III. For example, compounds with S as the linker A can be prepared following similar schemes, except that the phenolic starting material used for the synthesis of Formula I-2 is replaced by a corresponding —SH analog. An example is shown herein in Example 27. Compounds with $CH_2$ as the linker A can also be prepared following similar schemes. In such cases, a proper starting material with a "$CH_2$ nucleophile" can be used. For example, in some cases, such $CH_2$ liner can be prepared from a cyanomethylene starting material, which can be deprotonated to generate a carbanion to react with a chloropyridazine derivative, which can then be hydrolyzed and decarboxylated to generate a $CH_2$ linker. See e.g., *J. Med. Chem.* 57:3912-3923 (2014). Compounds with SO or $SO_2$ as linker A can be prepared from oxidation of the corresponding analog with S as the linker A.

As shown in Scheme 1, a typical synthesis of a compound of Formula I-2 can start with reacting an aminophenol S-1 with a pyridazine S-2 to form an aryl ether S-3. Conditions for effecting this transformation are known in the art and also exemplified in the Examples section. The leaving group $Lg^1$ in S-2 is typically Cl, although other leaving groups such as F can also be used and sometimes maybe advantageous. Hydrolysis of the chloropyridazine S-3 can then yield the pyridazinone compound S-4. The aniline function in S-4 can then be converted into an azauracil ring following known procedure or those described herein to provide the compound of Formula I-2. The variables $R^1$, $R^{1'}$, $R^2$, $R^4$, $R^{100}$, and n in Scheme 1 are defined herein.

Scheme 1

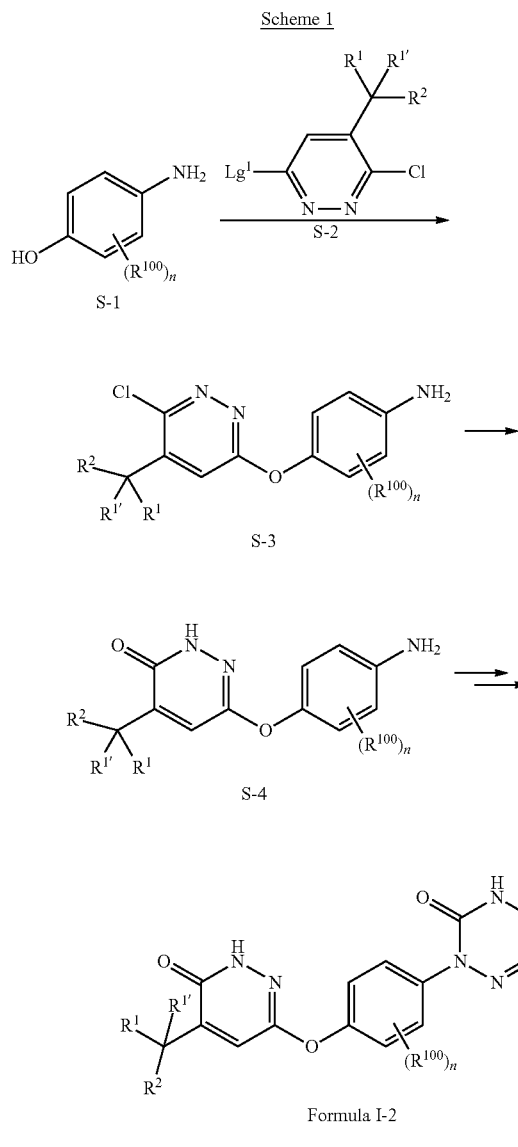

In some embodiments, $R^4$ is —CN, and the conversion of S-4 into cyanoazauracil can be achieved through diazotization of S-4, followed by reacting with a cyanoacetamide derivative S-5 to form an intermediate IM-1, which can then be cyclized to provide a compound of Formula I-2, Formula I-2-A. See Scheme 2 below. The variables $R^1$, $R^{1'}$, $R^2$, $R^{100}$, and n in Scheme 2 are defined herein.

Scheme 2

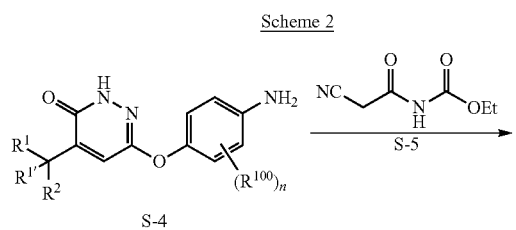

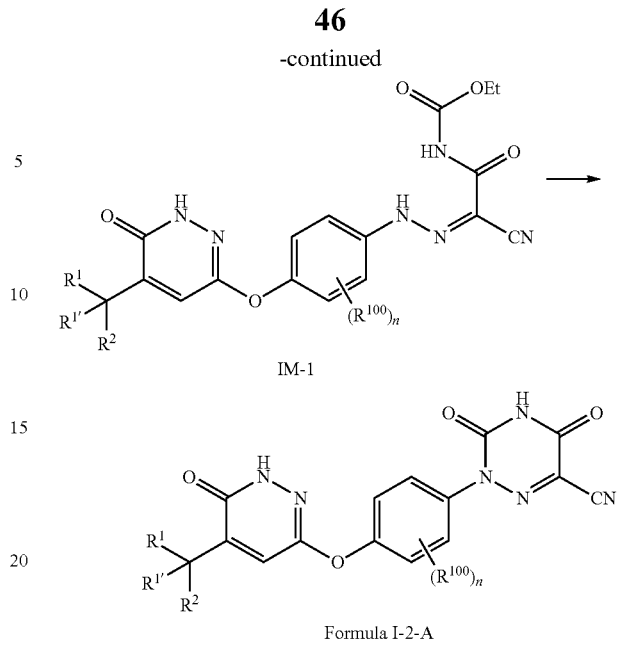

For embodiments where $R^4$ is an optionally substituted alkyl or cycloalkyl, such as methyl, ethyl, isopropyl, cyclopropyl, etc., the conversion of S-4 into an azauracil ring can be achieved through first converting the aniline into a hydrazine S-6, which is then reacted with an acid S-7 to form an intermediate IM-2, this intermediate can then be converted into intermediate IM-3 through reacting with carbamate S-8. The intermediate IM-3 can then by cyclized into an azauracil following similar conditions as described for Scheme 2. Conditions for the transformations in Scheme 3 are known in the art and also exemplified herein. The variables $R^1$, $R^{1'}$, $R^2$, $R^4$, $R^{100}$, and n in Scheme 3 are defined herein.

Scheme 3

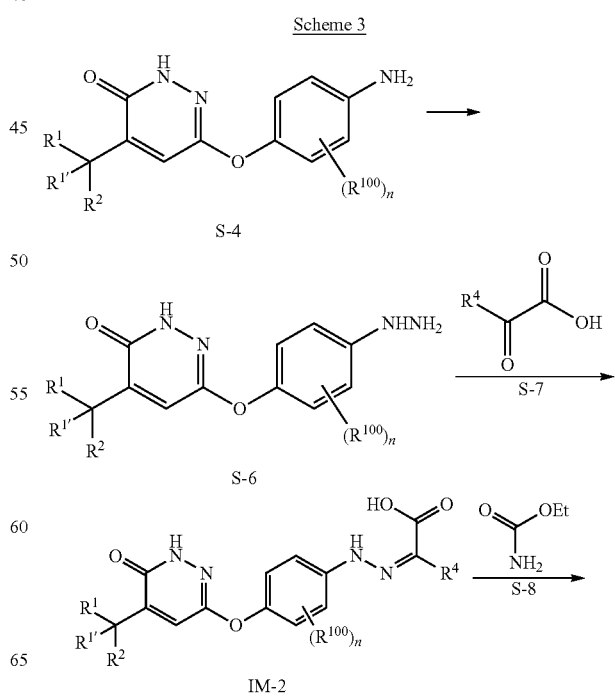

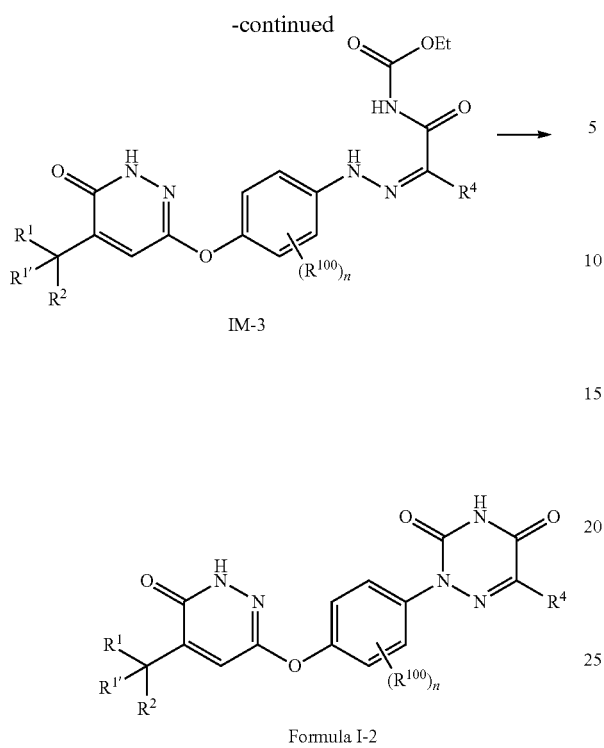

The various starting materials of S-2 can be prepared by following known procedures. For example, in some cases where Lg$^1$ is Cl, S-2 can be prepared by reacting dichloropyridazine with a carboxylic acid under a decarboxylative coupling condition in the presence of an oxidant. Example 6 shows a typical procedure for such a coupling reaction. Alternatively, S-2 can be prepared by first coupling 4-bromo-1,2,3,6-tetrahydropyridazine-3,6-dione with an appropriate reagent such as an organoboron reagent or other suitable reagent to form a pyridazine-dione derivative, which can be converted into S-2 following known procedures. An example of this method is shown in Example 19. Example 24 shows another method for preparing S-2, where an appropriate precursor (in Example 24, a benzyl substituted dichloropyridazine) can be deprotonated and then reacted with R$^1$-Lg (in Example 24, Me-I). Other compounds can be prepared similarly.

Alternatively, compound S-4 can be prepared by first reacting compound S-1 with dichloropyridazine as shown in Scheme 4. Thus, compound S-1 is first converted into compound S-9, which is then followed by hydrolysis of the chloropyridazine and protecting the aniline NH$_2$ to form the compound S-10. This is followed by introducing appropriate C(R$^1$)(R$^{1'}$)(R$^2$) group, for example, by reacting compound S-10 with an appropriate Grignard reagent followed by oxidation. After deprotection, compound S-4 can be obtained. An example of this method is shown in Example 7. The variables R$^1$, R$^{1'}$, R$^2$, R$^4$, R$^{100}$, and n in Scheme 4 are defined herein. Pg$^2$ can be any suitable amine protecting group, such as benzoyl.

The present disclosure also provides a method of preparing compounds of Formula I-1 as shown in Scheme 1A. For example, the pyridazinone IM-4 can be reduced to provide IM-5, which can react with an appropriate aldehyde (or other suitable reactants) under suitable condition to provide IM-6, which upon oxidation can provide a compound of Formula I-1. Example 25 provides a representative procedure. Alternatively, an appropriate S-10 can be reduced, which is then reacted with an appropriate aldehyde to form a compound of S-4, where R$^1$ and R$^{1'}$ are both hydrogen, which can also be converted into a compound of Formula I-1. A representative procedure is shown in Example 26.

Scheme 1A

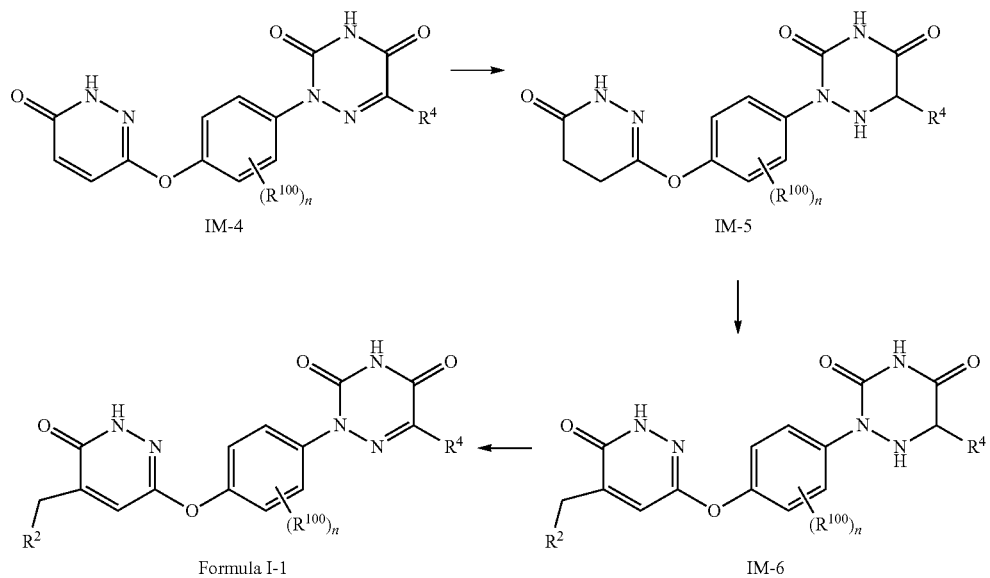

Indole derivatives of Formula III-1A can be synthesized following the general strategy herein. An example of synthesis is also described in detail in the Examples section. Briefly, as shown in Scheme 5 below, a 5-hydroxyindole derivative S-13 can react with a para-F nitrophenyl compound S-14 (or a similar nitrobenzene derivative with a leaving group at the para-position to the nitro group), to obtain an aryl ether S-15. The nitro group can then be reduced to an $NH_2$ group, which can be converted into an azauracil ring follow the general strategies described herein to obtain a compound of Formula III-1A. As will be understood by those skilled in the art, the indole S-13 can be readily synthesized by various indole synthesis such as Fisher indole synthesis. Reduction of nitro to $NH_2$ is also well known. The variables $R^1$, $R^{1'}$, $R^2$, $R^4$, $R^{100}$, n and p in Scheme 5 are defined herein. Compounds of Formula III-2A, and III-3A can be prepared similarly, except a corresponding pyrrolopyridine or indazole starting material is used. It should be noted that corresponding intermediates (i.e., replacing the indole unit with corresponding pyrrolopyridine or indazole in intermediate S-15 or S-16) that can lead to Compounds of Formula III-2A, and III-3A are also novel compounds of the present invention. Compounds of Formula III-4 can be prepared using similar methods, except that the indazole nitrogen is allowed to react with the corresponding S-14, for example. Representative procedures are shown in the Examples section.

Scheme 5

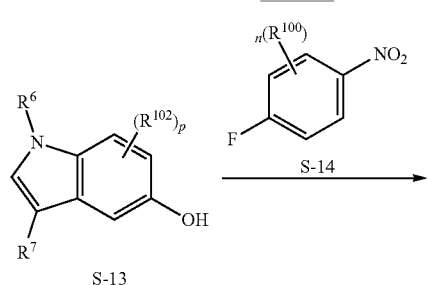

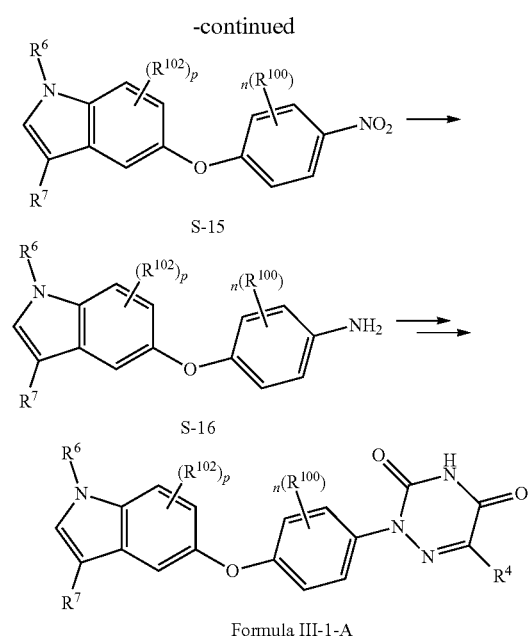

Compounds with a phosphoric acid unit replacing azauracil, see compounds of Formula I-X for example, can be prepared following a similar procedure as outlined in Example 23 and 28.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4th ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7$^{th}$ Edition), and Larock's Comprehensive Organic Transformations (Wiley-VCH, 1999), and any of available updates as of this filing.

Pharmaceutical Compositions

Certain embodiments are directed to a pharmaceutical composition comprising one or more of the compounds of the present disclosure.

The pharmaceutical composition can optionally contain a pharmaceutically acceptable excipient. In some embodiments, the pharmaceutical composition comprises a compound of the present disclosure (e.g., a compound of Formula I (e.g., Formula I-1, Formula I-2, Formula I-3, Formula I-4), a compound of Formula II (e.g., Formula II-1), a compound of Formula III (e.g., Formula III-1, Formula III-2, Formula III-3, Formula III-4, any subformula thereof), a compound of Formula I-X, Formula II-X, or Formula III-X, any one of compounds 1-99, or a pharmaceutically acceptable salt thereof) and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound of any of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), a compound of Formula I-X, Formula II-X, or Formula III-X, any one of compounds 1-99, or a pharmaceutically acceptable salt thereof, e.g., in a therapeutically effective amount. In any of the embodiments described herein, the pharmaceutical composition can comprise a therapeutically effective amount of a compound selected from compounds 1-99, or a pharmaceutically acceptable salt thereof.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure. In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Method of Treatment

Compounds of the present disclosure are useful as therapeutic active substances for the treatment and/or prophylaxis of diseases or disorders that are modulated by thyroid hormone receptor agonists.

In some embodiments, the present disclosure provides a method of treating a disease or disorder in a subject in need thereof. In some embodiments, the method comprises administering a therapeutically effective amount of a compound of the present disclosure (e.g., a compound of any of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), a compound of Formula I-X, Formula II-X, or Formula III-X, any one of compounds 1-99, or a pharmaceutically acceptable salt thereof) or a therapeutically effective amount of a pharmaceutical composition described herein.

The administering herein is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the administering is orally.

Various diseases or disorders can be treated by the methods herein. Non-limiting examples include obesity, hyperlipidemia, hypercholesterolemia, diabetes (e.g., type 2 diabetes), non-alcoholic steatohepatitis (NASH), fatty liver, non-alcoholic fatty liver disease (NAFLD), bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease, thyroid cancer, and combinations thereof. In some embodiments, the disease or disorder can be a metabolic disease such as type 2 diabetes or hyperlipidemia. In some embodiments, the cardiovascular disease is a coronary artery disease.

In some embodiments, the method is for treating obesity, hyperlipidemia, hypercholesterolemia, diabetes (e.g., type 2 diabetes), non-alcoholic fatty liver disease (NAFLD), non-alcoholic steatohepatitis (NASH), liver steatosis, atherosclerosis, cardiovascular diseases, hypothyroidism or thyroid cancer, which method comprises administering to a subject in need thereof a therapeutically effective amount of a compound of the present disclosure (e.g., a compound of any of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), a compound of Formula I-X, Formula II-X, or Formula III-X, any one of compounds 1-99, or a pharmaceutically acceptable salt thereof) or a pharmaceutical composition described herein.

In some embodiments, the present disclosure provides a method of treating a liver disease or disorder such as a non-alcoholic fatty liver disease (NAFLD) in a subject in need thereof. In some embodiments, the method comprises administering to the subject a therapeutically effective amount of a compound of the present disclosure (e.g., a compound of any of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), a compound of Formula I-X, Formula II-X, or Formula III-X, any one of compounds 1-99, or a pharmaceutically acceptable salt thereof) or a pharmaceutical composition described herein. In some preferred embodiments, the liver disease or disorder is liver fibrosis, hepatocellular carcinoma, or liver steatosis. In some preferred embodiments, the liver disease or disorder is non-alcoholic fatty liver disease (NAFLD), or non-alcoholic steatohepatitis (NASH).

In some embodiments, the present disclosure provides a method of treating a lipid disease or disorder in a subject in need thereof. In some embodiments, the method comprises administering to the subject a therapeutically effective amount of a compound of the present disclosure (e.g., a compound of any of Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), a compound of Formula I-X, Formula II-X, or Formula III-X, any one of compounds 1-99, or a pharmaceutically acceptable salt thereof) or a pharmaceutical composition described herein. In some preferred embodiments, the lipid disease or disorder is hyperlipidemia and/or hypercholesterolemia.

Dosing regimen including doses can vary and be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

NON-LIMITING EXEMPLARY EMBODIMENTS

The following provides some exemplary embodiments of the present disclosure.

1. A compound of Formula III, or a pharmaceutically acceptable salt thereof:

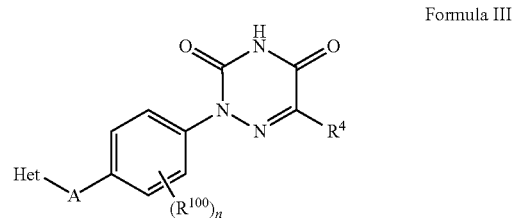

Formula III wherein:

Het is a 5,6-bicyclic or 6,6-bicyclic heteroaryl, which is substituted with 1-2 substituents independently selected from a nitrogen protecting group, —OH, —OPg$^1$, an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted; wherein Pg$^1$ is an oxygen protecting group, wherein the 5,6-bicyclic or 6,6-bicyclic heteroaryl is optionally further substituted as valence permits;

A is null, O, CH$_2$, S, SO or SO$_2$, each of R$^{100}$ at each occurrence is independently F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy, n is 1, 2, 3, or 4, wherein R$^4$ is hydrogen, —CN, —COOH, optionally substituted C$_{1-6}$ alkyl, or optionally substituted C$_{3-6}$ carbocyclyl.

2. The compound of embodiment 1, or a pharmaceutically acceptable salt or ester thereof, wherein the 5,6-bicyclic or 6,6-bicyclic heteroaryl is selected from indolyl, pyrrolopyridine, and indazolyl.

3. The compound of embodiment 1, or a pharmaceutically acceptable salt thereof, which is characterized by Formula III-4:

Formula III-4

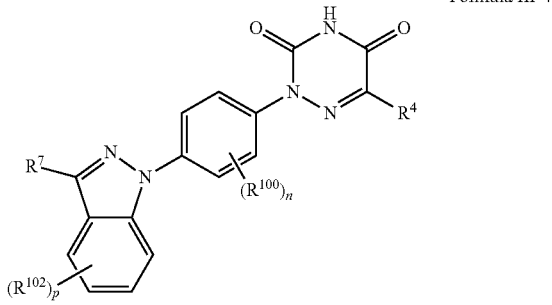

wherein:
R[7] is an optionally substituted alkyl, —COOH or an ester thereof, —CONH$_2$, —CONH(C$_{1-6}$ alkyl), —CON(C$_{1-6}$ alkyl)(C$_{1-6}$ alkyl), an optionally substituted aryl, an optionally substituted heteroaryl, an optionally substituted carbocyclyl or optionally substituted heterocyclyl, wherein each of the C$_{1-6}$ alkyl is independently selected and optionally substituted;
R$^{102}$ at each occurrence is independently —OH, —OPg$^1$, F, Cl, Br, I, C$_{1-4}$ alkyl optionally substituted with 1-3 fluorine, cyclopropyl, cyclobutyl, C$_{1-4}$ alkoxy optionally substituted with 1-3 fluorine, cyclopropoxy, or cyclobutoxy, wherein Pg$^1$ is an oxygen protecting group,
wherein p is 0, 1, 2, 3, or 4, as valence permits.

4. The compound of embodiment 3, or a pharmaceutically acceptable salt thereof, wherein R$^7$ is isopropyl or an optionally substituted C$_{3-6}$ cycloalkyl, e.g., with one or two substituents independently selected from C$_{1-4}$ alkyl optionally substituted with 1-3 fluorine, —OH, —OPg$^1$, C$_{1-4}$ alkoxy optionally substituted with 1-3 fluorine, and halogen, wherein Pg$^1$ is an oxygen protecting group.

5. The compound of embodiment 3, or a pharmaceutically acceptable salt thereof, wherein R$^7$ is —CONH$_2$, —CONH(C$_{1-4}$ alkyl), or —CON(C$_{1-4}$ alkyl)(C$_{1-4}$ alkyl), wherein each of the C$_{1-4}$ alkyl is independently selected and optionally substituted, e.g., with one or two substituents independently selected from C$_{1-4}$ alkyl optionally substituted with 1-3 fluorine, —OH, —OPg$^1$, C$_{1-4}$ alkoxy optionally substituted with 1-3 fluorine, and halogen, wherein Pg$^1$ is an oxygen protecting group.

6. The compound of embodiment 3, or a pharmaceutically acceptable salt thereof, wherein R$^7$ is an optionally substituted 4-7 membered heterocyclyl (e.g., piperidinyl or tetrahydropyranyl), e.g., with one or two substituents independently selected from C$_{1-4}$ alkyl optionally substituted with 1-3 fluorine, —OH, —OPg$^1$, C$_{1-4}$ alkoxy optionally substituted with 1-3 fluorine, and halogen, wherein Pg$^1$ is an oxygen protecting group.

7. The compound of any one of embodiments 1-2, or a pharmaceutically acceptable salt thereof, wherein A is null, S, O or CH$_2$.

8. The compound of any one of embodiments 3-7, or a pharmaceutically acceptable salt thereof, wherein p is 1.

9. The compound of embodiment 8, or a pharmaceutically acceptable salt thereof, wherein R$^{102}$ is OH or —OPg$^1$.

10. The compound of any one of embodiments 1-9, or a pharmaceutically acceptable salt thereof, wherein n is 2 or 3.

11. The compound of any one of embodiments 1-10, or a pharmaceutically acceptable salt thereof, wherein R$^{100}$ at each occurrence is independently F, Cl, Br, CF$_3$, or methyl.

12. The compound of any one of embodiments 1-11, or a pharmaceutically acceptable salt thereof, wherein the R$^{100}$ together with the phenyl ring they are attached to form one of the following:

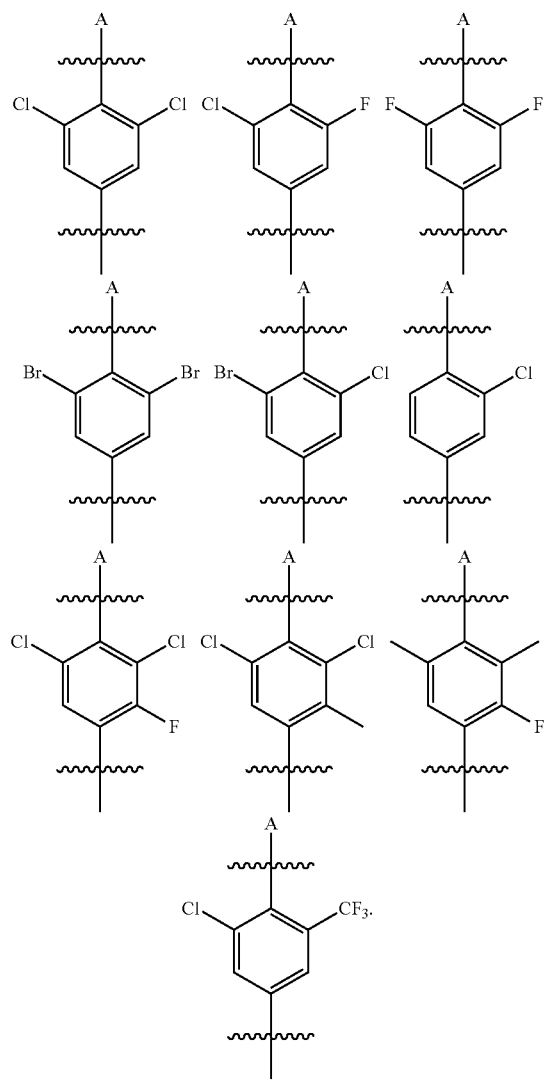

13. The compound of any one of embodiments 1-12, or a pharmaceutically acceptable salt thereof, wherein R$^4$ is C$_{1-6}$ alkyl or C$_{3-6}$ cycloalkyl, each optionally substituted with 1-3 fluorines, or R$^4$ is hydrogen, —CN, —COOH, methyl, ethyl, cyclopropyl, isopropyl, or propyl.

14. A pharmaceutical composition comprising the compound of any one of embodiments 1-13 or a pharmaceutical salt thereof, and optionally a pharmaceutically acceptable carrier.

15. A method of treating a disease or disorder in a subject in need thereof, comprising administering to the subject a therapeutically effective amount of the compound of any one of embodiments 1-13 or a pharmaceutical salt thereof, or the pharmaceutical composition of embodiment 14, wherein the disease or disorder is obesity, hyperlipidemia, hypercholesterolemia, diabetes, non-alcoholic steatohepatitis, fatty liver, non-alcoholic fatty liver disease, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease, thyroid cancer, or a combination thereof.

16. A method of treating a liver disease or disorder in a subject in need thereof, comprising administering to the subject a therapeutically effective amount of the compound of any one of embodiments 1-13 or a pharmaceutical salt thereof, or the pharmaceutical composition of embodiment 14.

17. The method of embodiment 16, wherein the liver disease or disorder is non-alcoholic steatohepatitis.

18. The method of embodiment 16, wherein the liver disease or disorder is non-alcoholic fatty liver disease.

19. A method of treating a lipid disease or disorder in a subject in need thereof, comprising administering to the subject a therapeutically effective amount of the compound of any one of embodiments 1-13 or a pharmaceutical salt thereof, or the pharmaceutical composition of embodiment 14.

20. The method of embodiment 19, wherein the lipid disease or disorder is hyperlipidemia and/or hypercholesterolemia.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable groups for Het, A, $R^1$, $R^{1'}$, $R^2$, $R^3$, $R^4$, $R^5$, $R^6$, $R^7$, $R^{100}$, $R^{102}$, n and p in compounds of Formula I, II, or III, or subformula thereof, as applicable, are independently selected. The described embodiments of the present invention can be combined. Such combination is contemplated and within the scope of the present invention. For example, it is contemplated that embodiments for any of Het, A, $R^{1'}$, $R^2$, $R^3$, $R^4$, $R^5$, $R^6$, $R^7$, $R^{100}$, $R^{102}$, n and p can be combined with embodiments defined for any other of Het, A, $R^{1'}$, $R^2$, $R^3$, $R^4$, $R^5$, $R^6$, $R^7$, $R^{100}$, $R^{102}$, n and p, as applicable.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers including racemic mixtures.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" or "compound(s) of the present invention" refers to any of the compounds described herein according to Formula I (e.g., Formula I-1, Formula I-2, Formula I-3, Formula I-4), Formula II (e.g., Formula II-1), Formula III (e.g., Formula III-1, Formula III-2, Formula III-3, Formula III-4, any subformula thereof), Formula I-X, Formula II-X, or Formula III-X, or any of Compounds 1-99, isotopically labeled compound(s) thereof (such as a deuterated analog wherein one of the hydrogen atoms is substituted with a deuterium atom with an abundance above its natural abundance), possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt or base addition salt such as Na salt). Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic hydrocarbon. In some embodiments, the alkyl which can include one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. For example, a $C_{1-4}$ alkyl group as used herein refers to a group selected from methyl, ethyl, propyl (n-propyl), isopropyl, butyl (n-butyl), sec-butyl, tert-butyl, and isobutyl. An optionally substituted $C_{1-4}$ alkyl group refers to the $C_{1-4}$ alkyl group as defined, optionally substituted with one or more permissible substituents as described herein. As used herein, the term "alkylene" as used by itself or as part of another group refers to a divalent radical derived from an alkyl group. For example, non-limiting straight chain alkylene groups include —$CH_2$—$CH_2$—$CH_2$—$CH_2$—, —$CH_2$—$CH_2$—$CH_2$—, —$CH_2$—$CH_2$—, and the like.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "cycloalkoxy" as used by itself or as part of another group refers to a radical of the formula $OR^{a1}$, wherein $R^{a1}$ is a cycloalkyl.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

"Carbocyclyl" or "carbocyclic" as used by itself or as part of another group refers to a radical of a non-aromatic cyclic hydrocarbon group having from 3 to 10 ring carbon atoms ("$C_{3-10}$ carbocyclyl") and zero heteroatoms in the non-aromatic ring system. The carbocyclyl group can be either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Non-limiting exemplary carbocyclyl groups include cyclopropyl, cyclobutyl, cyclopentyl, cyclohexyl, cycloheptyl, cyclooctyl, norbornyl, decalin, adamantyl, cyclopentenyl, and cyclohexenyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl").

"Heterocyclyl" or "heterocyclic" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Aralkyl" as used by itself or as part of another group refers to an alkyl substituted with one or more aryl groups, preferably, substituted with one aryl group. Examples of aralkyl include benzyl, phenethyl, etc. When an aralkyl is said to be optionally substituted, either the alkyl portion or the aryl portion of the aralkyl can be optionally substituted.

"Heteroaryl" as used by itself or as part of another group refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" as used by itself or as part of another group refers to an alkyl substituted with one or more heteroaryl groups, preferably, substituted with one heteroaryl group. When a heteroaralkyl is said to be optionally substituted, either the alkyl portion or the heteroaryl portion of the heteroaralkyl can be optionally substituted.

As commonly understood by those skilled in the art, alkylene, alkenylene, alkynylene, carbocyclylene, heterocyclylene, arylene, and heteroarylene refer to the corresponding divalent radicals of alkyl, alkenyl, alkynyl, carbocyclyl, heterocyclyl, aryl, and heteroaryl groups, respectively.

An "optionally substituted" group, such as an optionally substituted alkyl, optionally substituted alkenyl, optionally substituted alkynyl, optionally substituted carbocyclyl, optionally substituted heterocyclyl, optionally substituted aryl, and optionally substituted heteroaryl groups, refers to the respective group that is unsubstituted or substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O) OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0,1,2,3,4, or 5 R$^{dd}$ groups; wherein X$^-$ is a counterion; or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$ or =NO$R^{cc}$; each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0,1,2,3,4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$$X^-$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON($C_{1-6}$ alkyl)$_2$, —N($C_{1-6}$ alkyl)$_2$, —N($C_{1-6}$ alkyl)$_3$$^+$$X^-$, —NH($C_{1-6}$ alkyl)$_2$$^+$$X^-$, —NH$_2$($C_{1-6}$ alkyl)$^+$$X^-$, —NH$_3$$^+$$X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2C_{1-6}$ alkyl, —SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{CC}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N (R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, ar-C$_{1-10}$ alkyl, heteroar-C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated by reference herein.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O) (OR$^{cc}$)$_2$, and —P(=O)(N(R$^{bb}$)$_2$)$_2$, wherein X$^-$, R$^{aa}$, R$^{bb}$ and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, alkyl ethers or substituted alkyl ethers such as methyl, allyl, benzyl, substituted benzyls such as 4-methoxybenzyl, methoxylmethyl (MOM), benzyloxymethyl (BOM), 2-methoxyethoxymethyl (MEM), etc., silyl ethers such as trymethylsilyl (TMS), triethylsilyl (TES), triisopropylsilyl (TIPS), t-butyldimethylsilyl (TBDMS), etc., acetals or ketals, such as tetrahydropyranyl (THP), esters such as formate, acetate, chloroacetate, dichloroacetate, trichloroacetate, trifluoroacetate, methoxyacetate, etc., carbonates, sulfonates such as methanesulfonate (mesylate), benzylsulfonate, and tosylate (Ts), etc.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1. Synthesis of Compound 42

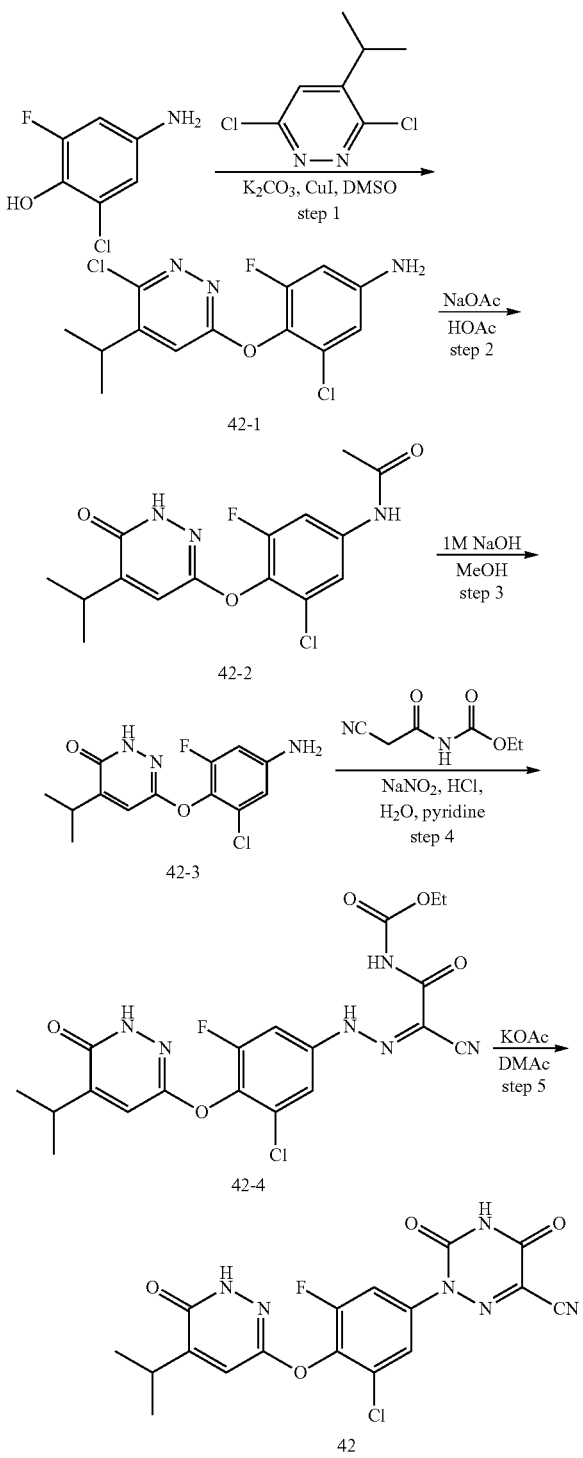

Step 1. To a 250 mL flask was charged with 4-amino-2-chloro-6-fluorophenol (2.50 g, 15.5 mmol), DMSO (40 mL), K$_2$CO$_3$ (6.40 g, 46.3 mmol), 3,6-dichloro-4-(propan-2-yl) pyridazine (3.00 g, 15.7 mmol) and CuI (1.75 g, 9.2 mmol). The resulting solution was heated at 85° C. overnight. The solution was diluted with water (200 mL) and adjusted to pH=8 with HCl (1 M). The mixture was extracted with 2×300 mL of ethyl acetate. The combined organic layer was washed with brine (2×300 mL), dried over anhydrous sodium sulfate, filtered and concentrated. The residue was purified by a reversed phase column chromatography with 0.05% aqueous NH$_4$HCO$_3$/acetonitrile (50% to 60% gradient in 10 min.) to afford 42-1.

Step 2. To a 250 mL flask was charged with 42-1 (1.0 g, 3.16 mmol) and sodium acetate (0.78 g, 9.49 mmol) in AcOH (30 mL). The mixture was heated at 100° C. overnight, cooled to room temperature, diluted with water (200 mL) and adjusted to pH =9 with NaOH (1 M). The resulting solution was extracted with ethyl acetate, and the combined organic layer was dried over anhydrous sodium sulfate, filtered and concentrated to give a crude product of 42-2 which was used in next step without further purification.

Step 3. To a 100 mL flask was charged with 42-2 (1.2 g, 2.83 mmol), MeOH (15 mL) and NaOH (1 M, 15 mL). The resulting solution was heated at 95° C. overnight. The mixture was cooled to room temperature, adjusted to pH=6 with HCl (1 M), diluted with water and extracted with ethyl acetate. The combined organic layer was dried over anhydrous sodium sulfate, filtered and concentrated. The residue was purified by silica gel column chromatography (ethyl acetate/petroleum ether=1:1) to afford 42-3.

Step 4. To a solution of 42-3 (140 mg, 0.47 mmol) in concentrated HCl (2.8 mL) and H$_2$O (8 mL) was added a solution of NaNO$_2$ (37 mg, 0.53 mmol) in water (0.3 mL) slowly at 0° C. The resulting solution was stirred at 0° C. for 1 hour. To a second flask was charged with ethyl N-(2-cyanoacetyl) carbamate (81 mg, 0.52 mmol) in pyridine (2.8 mL) and H$_2$O (9.4 mL), and the resulting solution was stirred at 0° C. for 30 min. Then the first reaction mixture was filtered and transferred to the second one, and the resulting suspension was stirred at 0° C. for 0.5 hour. The mixture was filtered and the filter cake was washed with water and petroleum ether, and dried to afford 42-4.

Step 5. To a 50 mL flask was charged with 42-4 (100 mg, 0.22 mmol), potassium acetate (24 mg, 0.25 mmol) and DMA (3 mL). The resulting solution was heated at 120° C. for 3 hours. The reaction mixture was cooled to room temperature, and then purified by a prep-HPLC (aqueous NH$_4$HCO$_3$ (10 mmol/L)/acetonitrile (21%-38%)) to afford compound 42 (42 mg). LCMS (ES, m/z): [M+H]$^+$=419.1; HNMR (300 MHz, DMSO-d$_6$, ppm): δ 12.23 (s, 1H), 7.66-7.62 (m, 2H), 7.43 (s, 1H), 3.12-3.00 (m, 1H), 1.19 (d, J=6.9 Hz, 6H).

Example 2. Synthesis of Compound 43

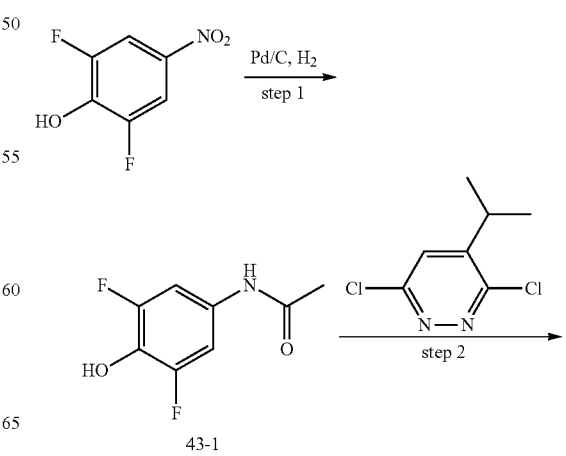

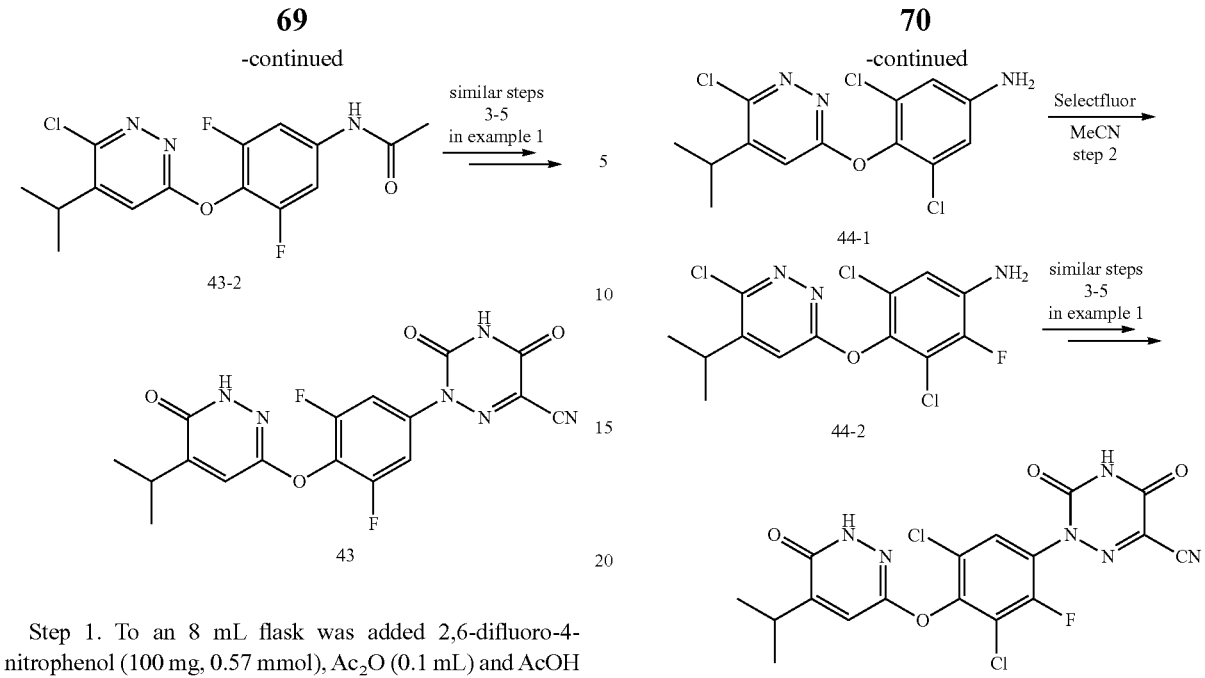

Step 1. To an 8 mL flask was added 2,6-difluoro-4-nitrophenol (100 mg, 0.57 mmol), Ac₂O (0.1 mL) and AcOH (2.0 mL) at room temperature. The suspension was degassed three times with nitrogen stream, and 10% Pd/C (30.0 mg, 0.085 mmol) was added under nitrogen atmosphere. The resulting mixture was stirred under H₂ atmosphere at room temperature for 3 hours, filtered, and the filter cake was washed with ethyl acetate. The filtrate was concentrated, and the residue was purified by silica gel column chromatography (petroleum ether/ethyl acetate=1:1) to afford 43-1.

Step 2. To a stirred solution of 43-1 (2.02 g, 10.7 mmol) in DMSO (20 mL) in a 100 mL 3-necked round-bottom flask was added N-(3,5-difluoro-4-hydroxyphenyl)acetamide (2.0 g, 10.7 mmol), CuI (3.46 g, 18.2 mmol) and K₂CO₃ (4.43 g, 32.1 mmol) at room temperature under nitrogen. The resulting mixture was stirred at 85° C. for 16 hours. The mixture was cooled to room temperature and filtered. The filtrate was diluted with water and extracted with ethyl acetate. The combined organic layer was washed with brine, dried over anhydrous sodium sulfate, filtered and concentrated. The residue was purified by silica gel column chromatography (petroleum ether/ethyl acetate=2:1) to afford 43-2.

Followed the similar steps in example 1 to synthesize 43. LCMS (ES, m/z): [M+H]⁺=403.0; HNMR (300 MHz, DMSO-d₆, ppm): δ 12.26 (s, 1H), 7.49-7.56 (m, 2H), 7.42 (s, 1H), 3.09-3.00 (m, 1H), 1.19 (d, J=6.9 Hz, 6H).

Example 3. Synthesis of Compound 44

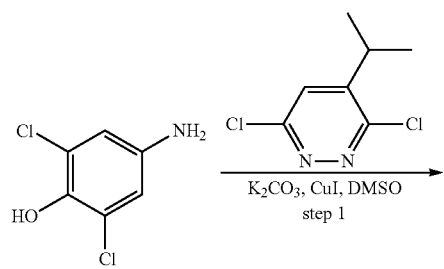

Step 1. To a 100 mL flask was charged with 4-amino-2,6-dichlorophenol (2 g, 11.24 mmol), DMSO (20 mL), K₂CO₃ (6.21 g, 44.94 mmol), 3,6-dichloro-4-(propan-2-yl)pyridazine (2.15 g, 11.25 mmol) and CuI (1.28 g, 6.72 mmol). The resulting mixture was heated at 90° C. for 16 hours, cooled to room temperature, neutralized to pH =8 with HCl (1 M) and filtered. The filtrate was diluted with water and extracted with ethyl acetate. The combined organic layer was washed with brine, dried over anhydrous sodium sulfate, filtered and concentrated. The residue was purified by silica gel column chromatography (ethyl acetate/petroleum ether=1:2) to afford 44-1.

Step 2. To a stirred solution of 44-1 in acetonitrile (100 mL) was added Selectfluor (2.24 g, 6.33 mmol) in portions at 0° C. under nitrogen atmosphere. The mixture was stirred at 0° C. for 10 min and then at 40° C. for 40 min. The mixture was cooled to room temperature, quenched with a saturated aqueous NaHCO₃ solution, and extracted with ethyl acetate. The combined organic layer was washed with brine, dried over anhydrous sodium sulfate, filtered and concentrated. The residue was purified by silica gel column chromatography to afford 44-2.

Followed the similar steps in example 1 to synthesize 44. LCMS (ES, m/z): [M+H]⁺=453.0; HNMR (300 MHz, DMSO-d₆, ppm): δ 12.27 (s, 1H), 7.92 (d, J=5.4 Hz, 1H), 7.48 (s, 1H), 3.18-3.03 (m, 1H), 1.26 (d, J=7.2 Hz, 6H).

Example 4. Synthesis of Compound 41

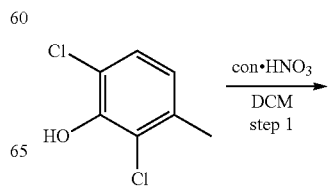

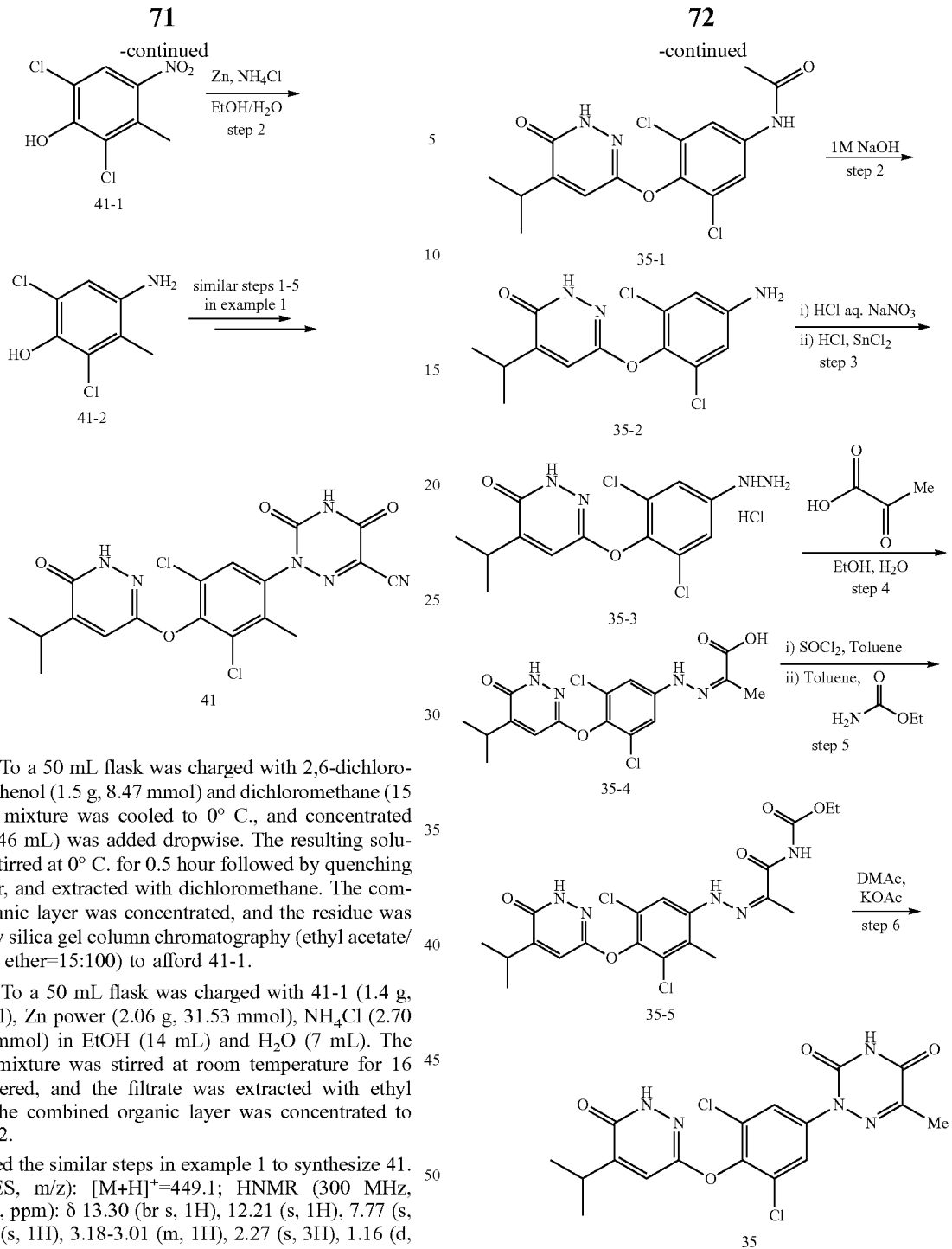

Step 1. To a 50 mL flask was charged with 2,6-dichloro-3-methylphenol (1.5 g, 8.47 mmol) and dichloromethane (15 mL). The mixture was cooled to 0° C., and concentrated $HNO_3$ (0.46 mL) was added dropwise. The resulting solution was stirred at 0° C. for 0.5 hour followed by quenching with water, and extracted with dichloromethane. The combined organic layer was concentrated, and the residue was purified by silica gel column chromatography (ethyl acetate/petroleum ether=15:100) to afford 41-1.

Step 2. To a 50 mL flask was charged with 41-1 (1.4 g, 6.31 mmol), Zn power (2.06 g, 31.53 mmol), $NH_4Cl$ (2.70 g, 50.45 mmol) in EtOH (14 mL) and $H_2O$ (7 mL). The resulting mixture was stirred at room temperature for 16 hours, filtered, and the filtrate was extracted with ethyl acetate. The combined organic layer was concentrated to afford 41-2.

Followed the similar steps in example 1 to synthesize 41. LCMS (ES, m/z): $[M+H]^+$=449.1; HNMR (300 MHz, DMSO-$d_6$, ppm): δ 13.30 (br s, 1H), 12.21 (s, 1H), 7.77 (s, 1H), 7.45 (s, 1H), 3.18-3.01 (m, 1H), 2.27 (s, 3H), 1.16 (d, J=6.9 Hz, 6H).

Example 5. Synthesis of Compound 35

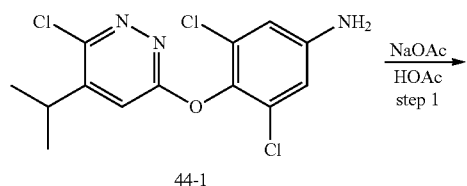

Step 1. To a 100 mL flask was charged with 3,5-dichloro-4-[[6-chloro-5-(propan-2-yl)pyridazin-3-yl]oxy]aniline (1.5 g, 4.51 mmol), sodium acetate (1.29 g, 15.72 mmol) and AcOH (15 mL). The mixture was heated at 100° C. for 16 hours, cooled to room temperature, and adjusted to pH=8 with an aqueous NaOH (1 M) solution. The resulting solution was extracted with ethyl acetate, and the combined organic layer was dried over anhydrous sodium sulfate, filtered and concentrated to afford 35-1.

Step 2. To a 100 mL flask was charged with 35-1 (1 g, 2.81 mmol), MeOH (10 mL) and NaOH (1 M, 10 mL). The resulting mixture was heated at 100° C. for 16 hours, cooled to room temperature, and adjusted to pH=5 with an aqueous HCl (1 M) solution. The solution was extracted with ethyl acetate, and the combined organic layer was dried over anhydrous sodium sulfate, filtered and concentrated. The residue was purified by silica gel column chromatography (ethyl acetate/petroleum ether=1:1) to afford 35-2.

Step 3. To a solution of 35-2 (407 mg, 1.3 mmol) in water (8 mL) and concentrated hydrochloride acid (4 mL) was added sodium nitrite (90 mg, 1.3 mmol) at 0° C., and the mixture was stirred for 0.5 hour. To above mixture was added a solution of stannous chloride (983 mg, 5.2 mmol) in concentrated hydrochloride acid (2 mL). The reaction mixture was then stirred for 0.5 hour and filtered. The filter cake was collected to afford 35-3 which was used for next step without further purification.

Step 4. To a solution of 35-3 (700 mg, 1.3 mmol) in ethanol (5 mL) and water (15 mL) was added pyruvic acid (229 mg, 2.6 mmol) at room temperature. The mixture was stirred for 0.5 hour and filtered. The filter cake was washed with water, collected, and slurried with dichloromethane (15 mL). The slurry was filtered, and the filter cake was collected and dried to afford 35-4.

Step 5. To a solution of 35-4 (360 mg, 0.9 mmol) in toluene (60 mL) was added thionyl chloride (212 mg, 1.8 mmol) at room temperature. The mixture was stirred at 110° C. for 2 hours, concentrated and dissolved in toluene (60 mL) again. To above mixture was added urethane (160 mg, 1.8 mmol) at room temperature. The mixture was then stirred at 110° C. for 2 hours, cooled to room temperature, and concentrated. The residue was purified by column chromatography on silica gel (dichloromethane to dichloromethane/methanol=10:1) to afford 35-5.

Step 6. To a solution of 35-5 (55 mg, 0.12 mmol) in dimethylacetamide (3 mL) was added potassium acetate (59 mg, 0.6 mmol) at room temperature. The mixture was stirred at 60° C. for 16 hours, cooled, and purified by a prep-HPLC (acetonitrile with 0.05%TFA in water: 25% to 95%) to afford 35. LCMS: (ESI, m/z): [M+H]$^+$=424.3; HNMR (400 MHz, DMSO-$d_6$, ppm): δ 12.38 (br s, 1H), 12.18 (s, 1H), 7.76 (s, 2H), 7.40 (s, 1H), 3.05-2.97 (m, 1H), 2.13 (s, 3H), 1.16 (d, J=6.8 Hz, 6H).

Example 6. Synthesis of Compound 1

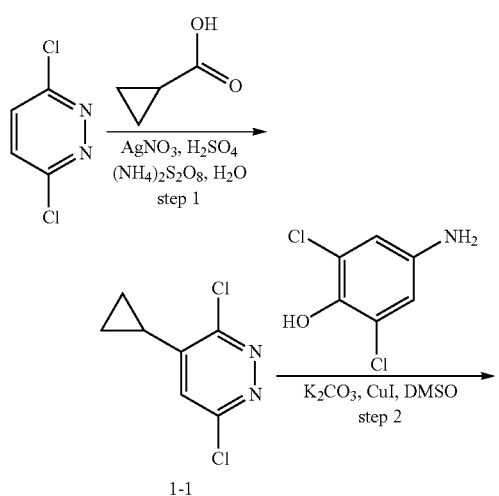

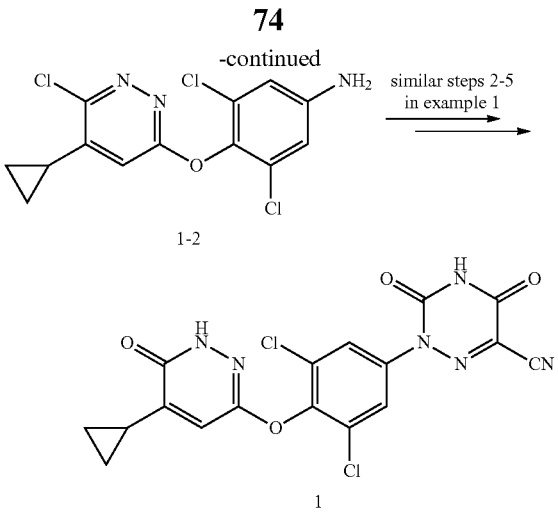

Step 1. To a suspension of 3,6-dichloropyridazine (10.43 g, 70.0 mmol) in water (210 mL) was added concentrated sulfuric acid (5.74 mL, 105.0 mmol), silver nitrate (1.19 g, 7.0 mmol) and cyclopropanecarboxylic acid (7.24 mL, 91.0 mmol) at room temperature. The mixture was heated to 65° C., and a solution of ammonium persulfate (23.94 g, 105.0 mmol) in water (70 mL) was added dropwise over 20 mins. (T<72° C.). Then the mixture was stirred at 70° C. for 0.5 hour, cooled to room temperature, and poured into ice-water (50 mL). The mixture was adjusted to pH=9 with ammonium hydroxide and extracted with dichloromethane. The combined organic layer was washed with an aqueous sodium hydroxide (1 M) solution, water and brine, dried over sodium sulfate, filtered and concentrated. The residue was purified by flash column chromatography on silica gel (petroleum ether to petroleum ether/ethyl acetate=1:1) to afford 1-1.

Step 2. To a 100 mL flask purged with nitrogen was charged with 4-amino-2,6-dichlorophenol (1.5 g, 8.43 mmol), 1-1 (1.67 g, 8.85 mmol), $K_2CO_3$ (3.49 g, 25.3 mmol), CuI (0.80 g, 4.21 mmol) and DMSO (30 mL). The resulting solution was stirred at 90° C. for 18 h, cooled to room temperature, diluted with water, and adjusted to pH=8 with a HCl (1 M) solution, and extracted with ethyl acetate. The combined organic layer was washed with brine, dried over anhydrous sodium sulfate, filtered and concentrated. The residue was purified by flash column chromatography on silica gel (ethyl acetate/petroleum ether=1:3 to 1:1) to give a product as a mixture of isomers, which was purified by re-crystallization from diethyl ether and hexane to afford 1-2.

Followed the similar steps in example 1 to synthesize 1. LCMS: (ESI, m/z): [M+H]$^+$=433.2; HNMR (300 MHz, DMSO-$d_6$, ppm): δ 13.30 (br s, 1H), 12.21 (s, 1H), 7.77 (s, 2H), 7.18 (s, 1H), 2.27-2.13 (m, 1H), 1.24-1.07 (m, 4H).

Example 7. Synthesis of Compound 25

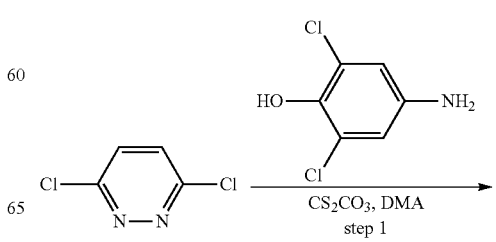

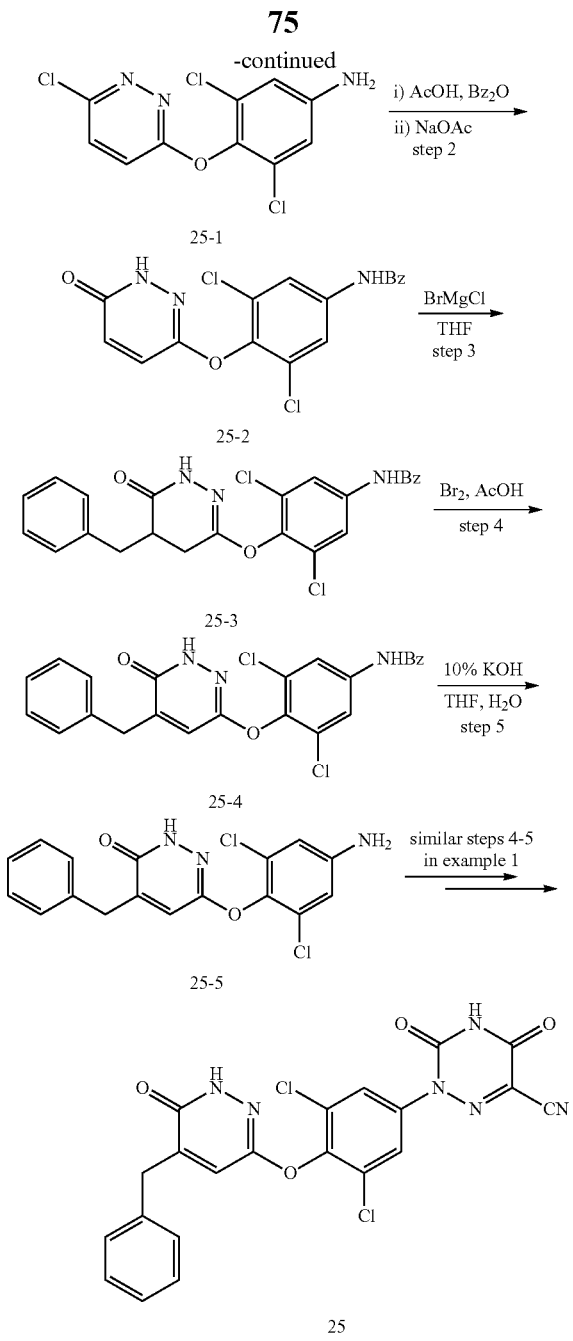

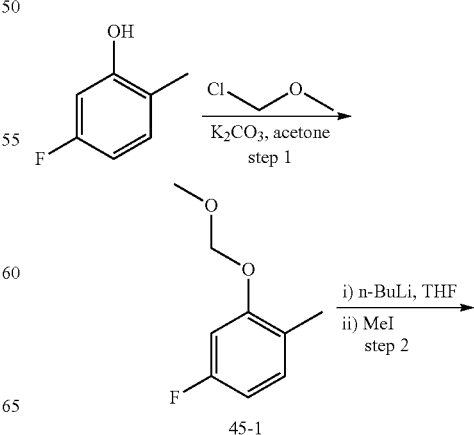

was stirred at 110° C. for 16 hours. Water (120 mL) was added dropwise after the mixture was cooled to 70° C., and the mixture was then cooled to room temperature and filtered. The filter cake was washed with water, and recrystallized with AcOH (220 mL) and water (200 mL) to afford 25-2.

Step 3. To a stirred solution of 25-2 (2.2 g, 5.8 mmol) in tetrahydrofuran (45 mL) was added benzylmagnesium chloride (1 M in tetrahydrofuran, 35 mL, 35 mmol) dropwise at 35° C. under nitrogen. The mixture was stirred at 35° C. for 1 hour, cooled to 10° C., adjusted to pH=4 with 1 M of hydrochloric acid, and extracted with ethyl acetate. The combined organic layer was washed with water and brine, dried over anhydrous sodium sulfate, filtered and concentrated. The residue was purified by column chromatography on silica gel (petroleum ether to petroleum ether/ethyl acetate=2:1) to afford 25-3.

Step 4. To a solution of 25-3 (1.2 g, 2.5 mmol) in acetic acid (120 mL) was added bromine (1.6 g, 10 mmol) at room temperature. The mixture was stirred at 90° C. for 3 hours and then cooled to room temperature. Water (220 mL) was added and the mixture was extracted with ethyl acetate. The combined organic layer was washed with an aqueous sodium bicarbonate solution and brine, dried over anhydrous sodium sulfate, filtered and concentrated. The residue was purified by column chromatography on silica gel (petroleum ether to petroleum ether/ethyl acetate=2:1) to afford 25-4.

Step 5. To a solution of 25-4 (0.35 g, 0.75 mmol) in tetrahydrofuran (5 mL) was added an aqueous potassium hydroxide (10 wt %, 5 mL) solution at room temperature. The mixture was stirred at 80° C. for 72 hours, cooled, concentrated to remove tetrahydrofuran, and adjusted to pH=8 with 1 M of hydrochloric acid. The mixture was filtered, and the filter cake was washed with water, dried, and purified by a preparative TLC (petroleum ether/ethyl acetate=3:2) to afford 25-5.

Followed the similar steps in example 1 to synthesize 25. LCMS (ESI, m/z): [M+H]$^+$=483.3; HNMR (400 MHz, DMSO-$d_6$, ppm): δ 12.30 (s, 1H), 7.73 (s, 2H), 7.32-7.30 (m, 5H), 7.25-7.22 (m, 1H), 3.83 (s, 2H).

Example 8. Synthesis of Compound 45

Step 1. A mixture of 4-amino-2,6-dichlorophenol (18.2 g, 102 mmol), 3,6-dichloropyridazine (15 g, 100 mmol) and cesium carbonate (37 g, 115 mmol) in N,N-dimethylacetamide (100 mL) was stirred at 110° C. for 3 hours and then at 70° C. for 16 hours under nitrogen. After cooled to room temperature, the mixture was filtered with Celite, and the filtrate was poured into water (600 mL) and extracted with ethyl acetate. The combined organic layer was washed with brine, dried over anhydrous sodium sulfate, filtered and concentrated to afford 25-1 which was used in the next step directly.

Step 2. To a solution of 25-1 (14 g, 38.6 mmol) in acetic acid (120 mL) was added benzoic anhydride (9.6 g, 42.5 mmol), and the mixture was stirred at 100° C. for 1 hour. After the reaction mixture was cooled to room temperature, sodium acetate (6.3 g, 77 mmol) was added and the mixture

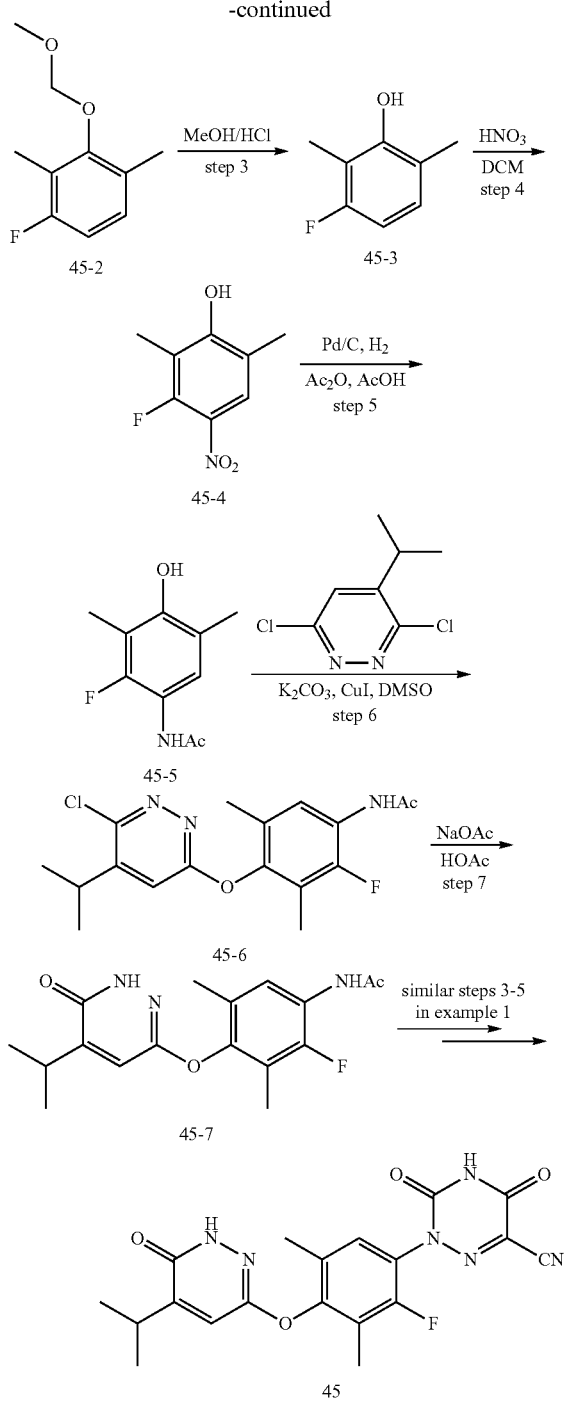

MeI (17.4 g, 122.2 mmol) was added dropwise at −78° C., and the mixture was allowed to warm to room temperature and stirred for 16 hours. The mixture was quenched with a saturated aqueous NH$_4$Cl solution and extracted with ethyl acetate. The combined organic phase was washed by brine, dried over anhydrous sodium sulfate, filtered and concentrated. The residue was purified by flash column chromatography on silica gel (petroleum ether/ethyl acetate=8:1) to afford 45-2.

Step 3. To a stirred solution of 45-2 (21 g, 114.0 mmol) in MeOH (200 mL) was added concentrated HCl (4.50 mL) dropwise. The mixture was stirred at 50° C. for 3 hours and concentrated. The residue was purified by flash column chromatography on silica gel (petroleum ether) to afford 45-3.

Step 4. To a stirred solution of 45-3 (15 g, 107.0 mmol) in dichloromethane (150 mL) was added concentrated HNO$_3$ (8.09 g, 128.43 mmol) dropwise at 0° C., and the mixture was stirred for 1 hour followed by quenching with ice-water at 0° C. The mixture was separated and the aqueous layer was extracted with CH$_2$Cl$_2$. The combined organic phase was dried over anhydrous sodium sulfate, filtered and concentrated. The residue was purified by flash column chromatography on silica gel (petroleum ether/ethyl acetate=5:1) to afford 45-4.

Step 5. To a stirred solution of 45-4 (2.5 g, 13.5 mmol) and Ac$_2$O (2.5 mL) in AcOH (50 mL) was added 10% Pd/C (250 mg) in portions under nitrogen. The mixture was exchanged to hydrogen and stirred at room temperature for 3 hours followed by filtration. The filtrate was concentrated and the residue was purified by flash column chromatography on silica gel (petroleum ether/ethyl acetate=5:1) to afford 45-5.

Step 6. To a stirred solution of 45-5 (1.45 g, 7.6 mmol) and N-(2-fluoro-4-hydroxy-3,5-dimethyl-phenyl)acetamide (1.5 g, 7.61 mmol) in DMSO (10 mL) was added K$_2$CO$_3$ (3.18 g, 22.8 mmol) and CuI (450 mg, 4.6 mmol) in portions at 90° C. The mixture was stirred at 90° C. for 14 hours and then cooled to room temperature. After filtration, the filter cake was washed with ethyl acetate, and the residue was purified by flash column chromatography on silica gel (petroleum ether/ethyl acetate=5:1) to afford 45-6.

Step 7. To a stirred solution of 45-6 (1.2 g, 3.4 mmol) in AcOH (10 mL) was added NaOAc (880 mg, 10.73 mmol) in portions. The mixture was stirred at 100° C. for 14 hours, cooled to room temperature, and adjusted to pH=8 with NaOH (1 M). The resulting solution was extracted with ethyl acetate, and the combined organic layer was dried over anhydrous sodium sulfate, filtered and concentrated. The residue was purified by flash column chromatography on silica gel (petroleum ether/ethyl acetate=5:1) to afford 45-7.

Followed the similar steps in example 1 to synthesize 45. LCMS (ESI, m/z): [M+H]$^+$=413.2; HNMR (300 MHz, DMSO-d$_6$, ppm): δ 12.08 (s, 1H), 7.35-7.32 (m, 2H), 3.11-3.02 (m, 1H), 2.12 (s, 3H), 2.08 (s, 3H), 1.20 (d, J=6.9 Hz, 6H).

Step 1. A solution of 5-fluoro-2-methylphenol (15 g, 118.9 mmol) in acetone (150 mL) in a 500 mL flask was cooled to 0° C., and K$_2$CO$_3$ (41.1 g, 297.3 mmol) was added. After stirred for 2 hours, chloro(methoxy)methane (10.5 g, 130.8 mmol) was added, and the mixture was stirred at room temperature for 16 hours and then concentrated. The residue was purified by flash column chromatography on silica gel (petroleum ether/ethyl acetate=8:1) to afford 45-1.

Step 2. To a stirred solution of 45-1 (16 g, 94.0 mmol) in tetrahydrofuran (160 mL) was added n-BuLi (1.6 M in hexane, 70 mL, 112.9 mmol) dropwise at −78° C. under nitrogen, and the mixture was stirred at −78° C. for 2 hours.

Example 9. Synthesis of Compound 39

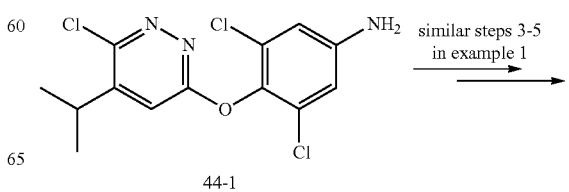

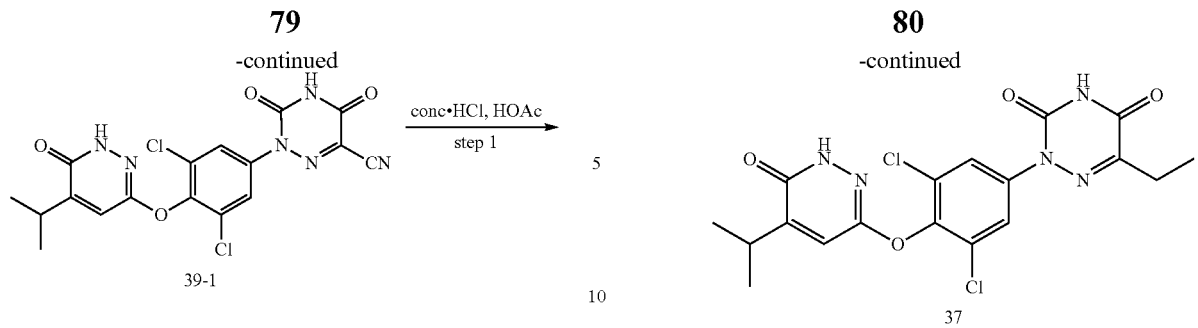

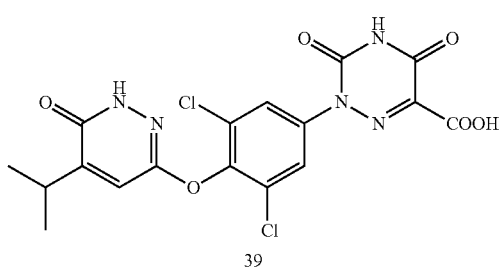

Followed the similar steps in example 1 to synthesize 39-1.

Step 1. To a 100 mL flask was charged with 39-1 (200 mg, 0.46 mmol), AcOH (6 mL) and concentrated HCl (0.6 mL, 19.75 mmol), and the mixture was heated at 120° C. for 24 hours. The resulting mixture was cooled to room temperature, diluted with 50 mL of $H_2O$, and adjusted to pH=5 with NaOH (1 M). The solution was extracted with diethyl ether and the combined organic layer was dried over anhydrous sodium sulfate, filtered and concentrated. The residue was purified by a prep-HPLC (0.1% aqueous formic acid/acetonitrile=61% to 80%) to afford 39 (6.4 mg). LCMS (ESI, m/z): [M+H]$^+$=454.2; HNMR (300 MHz, DMSO-$d_6$, ppm): δ 12.18 (s, 1H), 8.14 (s, 1H), 7.81 (s, 2H), 7.44 (s, 1H), 3.14-2.95 (m, 1H), 1.20 (d, J=6.9 Hz, 6H).

Example 10. Synthesis of Compound 37

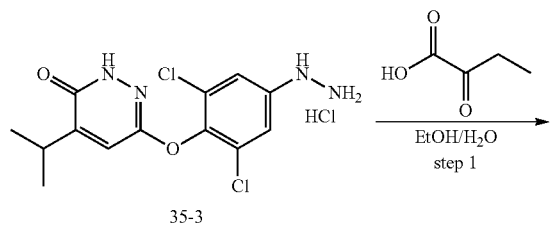

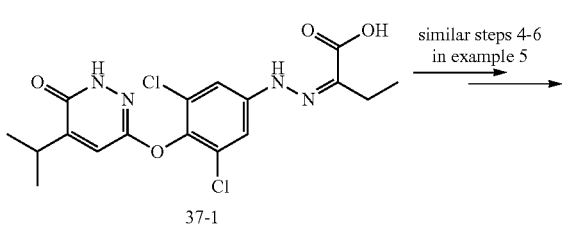

Step 1. To a 50 mL flask was added 35-3 (600 mg, 1.21 mmol), 2-oxobutanoic acid (247 mg, 2.42 mmol), EtOH (5 mL) and $H_2O$ (15 mL) at room temperature. The resulting mixture was stirred at room temperature for 1 hour and filtered. The filter cake was washed with water, collected, and diluted with dichloromethane. The slurry was stirred, filtered and the filter cake was dried to afford 37-1.

Followed the similar steps in example 5 to synthesize 37. LCMS (ESI, m/z): [M+H]$^+$=438.2; HNMR (300 MHz, DMSO-$d_6$, ppm): δ 12.22 (s, 1H), 7.82 (s, 2H), 7.45 (s, 1H), 3.10-3.00 (m, 1H), 2.62-2.55 (m, 2H), 1.24 (s, 1H), 1.20 (d, J=6.9 Hz, 6H), 1.19-1.13 (m, 3H).

Example 11. Synthesis of Compound 40

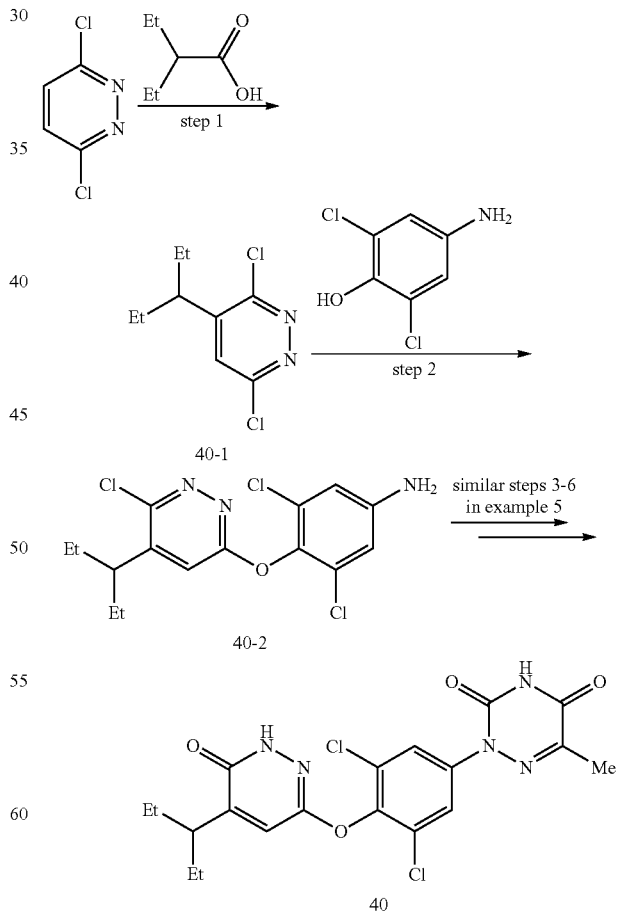

Step 1. To a suspension of 3,6-dichloropyridazine (10.0 g, 67.56 mmol) in water (200 mL) was added concentrated sulfuric acid (5.5 ml, 101.36 mmol), silver nitrate (1.15 g, 6.76 mmol) and 2-ethylbutanoic acid (10.2 g, 87.84 mmol) at room temperature. The mixture was heated to 65° C., and a solution of ammonium persulfate (23.2 g, 101.36 mmol) in water (70 mL) was added dropwise over 20 mins (T<72° C.). The mixture was stirred at 70° C. for 0.5 hour, cooled to room temperature, and poured into ice-water. The solution was adjusted to pH=9 with ammonium hydroxide and extracted with dichloromethane. The combined organic layer was washed with an aqueous sodium hydroxide (1 M) solution, water and brine. The separated organic layer was dried over anhydrous sodium sulfate, filtered and concentrated to afford 40-1 which was used for next step without further purification.

Step 2. To a solution of 40-1 (5.0 g, 22.94 mmol) in dimethylacetamide (50 mL) was added cesium carbonate (7.8 g, 23.98 mmol) and 4-amino-2,6-dichlorophenol (3.7 g, 20.85 mmol) at room temperature. The mixture was stirred at 90° C. for 6 hours under nitrogen. After cooled to room temperature, the reaction mixture was diluted with ethyl acetate, and washed with water and brine. The organic layer was dried over anhydrous sodium sulfate, filtered and concentrated. The residue was purified by column chromatography on silica gel (petroleum ether to petroleum ether/ethyl acetate=2:1) to give a crude product which was slurried with diethyl ether at 0° C. The slurry was filtered, and the filter cake was collected and dried to afford 40-2.

Followed the similar steps in example 5 to synthesize 40. LCMS (ESI, m/z): [M+H]⁺=452.3; HNMR (400 MHz, DMSO-d₆, ppm): δ 12.37 (s, 1H), 12.18 (s, 1H), 7.76 (s, 2H), 7.40 (s, 1H), 2.78-2.71 (m, 1H), 2.12 (s, 3H), 1.63-1.56 (m, 4H), 0.75 (t, J=7.2 Hz, 6H).

Example 12. Synthesis of Compound 33

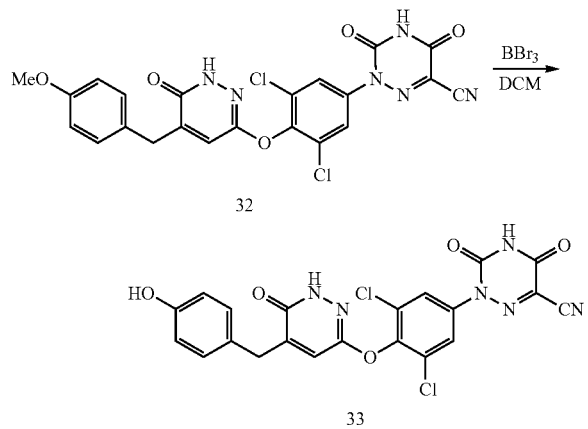

To a solution of 32 (75 mg, 0.15 mmol) in dichloromethane (5 mL) was added boron tribromide (0.5 mL) at 0° C. The mixture was stirred at 0° C. for 2 hours, and then poured into ice water. A saturated aqueous sodium bicarbonate solution was added, and the mixture was extracted with dichloromethane. The combined organic layer was washed with brine, dried over anhydrous sodium sulfate, filtered and concentrated. The residue was purified by a prep-HPLC (acetonitrile with 0.05% aqueous trifluoroacetic acid: 20% to 95%) to afford 33. LCMS (ESI, m/z): [M+H]⁺=499.3; HNMR (400 MHz, DMSO-d₆, ppm): δ 13.14 (br s, 1H), 12.25 (s, 1H), 9.28 (s, 1H), 7.74 (s, 2H), 7.21 (s, 1H), 7.11 (d, J=8.4 Hz, 2H), 6.70 (d, J=8.4 Hz, 2H), 3.70 (s, 2H).

Example 13. Synthesis of Compound 27

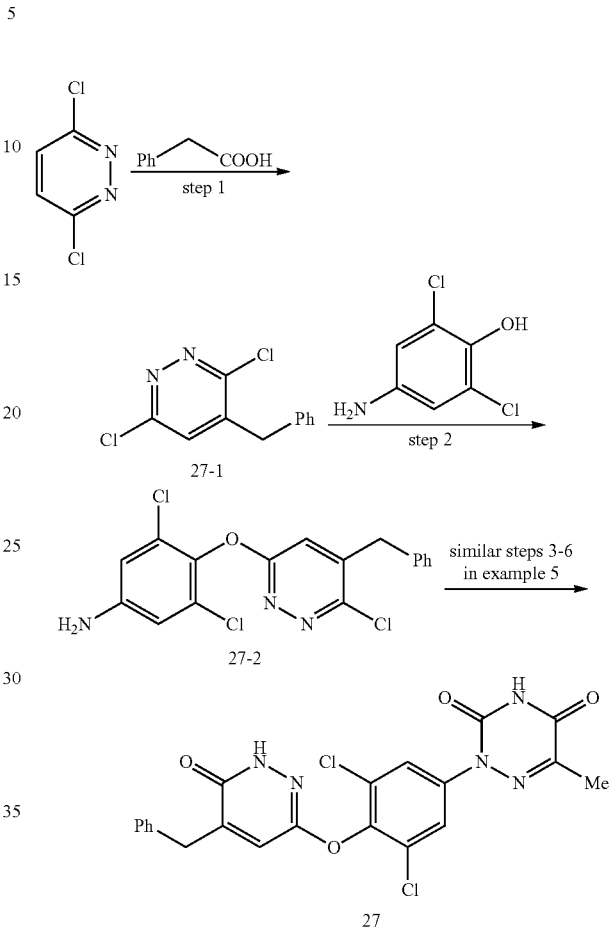

Step 1. To a suspension of 3,6-dichloropyridazine (12.5 g, 84 mmol) in water (160 mL) was added concentrated sulfuric acid (12.6 g, 126 mmol), silver nitrate (1.4 g, 8.4 mmol) and 2-phenylacetic acid (15 g, 110 mmol) at room temperature. The mixture was heated to 65° C., and a solution of ammonium persulfate (28 g, 126 mmol) in water (100 mL) was added dropwise over 20 mins (T<72° C.). After stirring at 70° C. for 0.5 hour, the reaction mixture was cooled to 0° C. and separated. The organic layer was diluted with dichloromethane, washed with an aqueous sodium hydroxide (1 M) solution, water and brine. The organic layer was dried over anhydrous sodium sulfate, filtered and concentrated. The residue was purified by column chromatography on silica gel (ethyl acetate to ethyl acetate/petroleum ether=0 to 12%) to afford 27-1.

Step 2. A mixture of 4-amino-2,6-dichlorophenol (2.3 g, 13 mmol), 27-1 (2.8 g, 11.7 mmol), and cesium carbonate (4.3 g, 13 mmol) in dimethylacetamide (50 mL) was stirred at 90° C. for 3 hours. After cooled to room temperature, the reaction mixture was diluted with ethyl acetate, washed with water and brine, dried over sodium sulfate, filtered and concentrated. The residue was purified by column chromatography on silica gel (petroleum ether to petroleum ether/ethyl acetate=1:2) to afford 27-2.

Followed the similar steps in example 5 to synthesize 27. LCMS (ESI, m/z): [M+H]⁺=472.3; HNMR (400 MHz, DMSO-$d_6$, ppm): δ 12.38 (s, 1H), 12.28 (s, 1H), 7.76 (s, 2H), 7.33-7.32 (m, 4H), 7.26 (s, 1H), 7.25-7.24 (m, 1H), 3.83 (s, 2H), 2.13 (s, 3H).

Example 14. Synthesis of Compound 28

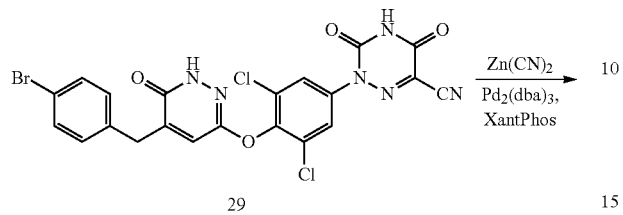

To a solution of 29 (30 mg, 0.05 mmol) in DMF (4 mL) was added zinc cyanide (8.7 mg, 0.075 mmol), $Pd_2(dba)_3$ (9.1 mg, 0.01 mmol) and 9,9-dimethyl-4,5-bis(diphenylphosphino) xanthene (11.6 mg, 0.02 mmol), and the mixture was stirred at 110° C. for 6 hours under nitrogen. The reaction mixture was cooled to room temperature and purified by a prep-HPLC (acetonitrile with 0.05% of aqueous TFA: 15% to 65%) to afford 28. LCMS (ESI, m/z): $[M+H]^+$=508.3; HNMR (400 MHz, DMSO-$d_6$, ppm): δ 13.24 (br s, 1H), 12.35 (s, 1H), 7.78 (d, J=8.4 Hz, 2H) 7.74 (s, 2H), 7.53 (d, J=8.0 Hz, 2H), 7.46 (s, 1H), 3.93 (s, 2H).

Example 15. Synthesis of Compound 16

Step 1. To a solution of 3,6-dichloropyridazine (10 g, 67 mmol) in acetonitrile (150 mL) and water (150 mL) was added 3-oxocyclobutane-1-carboxylic acid (23 g, 201 mmol), ammonium persulfate (30.6 g, 134 mmol), silver nitrate (11.4 g, 67 mmol) and trifluoroacetic acid (1.5 g, 13.4 mmol) at room temperature. The reaction mixture was stirred at 70° C. for 2 hours under nitrogen atmosphere. The mixture was cooled and filtered. The filtrate was neutralized with ammonium hydroxide to pH=8, and then extracted with ethyl acetate. The organic layer was dried over anhydrous sodium sulfate, filtered and concentrated. The residue was purified by column chromatography on silica gel (petroleum ether to petroleum ether/ethyl acetate=3:1) to afford 16-1.

Step 2. To a solution of 16-1 (560 mg, 2.6 mmol) in methanol (10 mL) was added potassium borohydride (180 mg, 3.4 mmol) at 0° C. under nitrogen. The mixture was stirred at 0° C. for 1 hour, followed by quenching with water. The mixture was extracted with ethyl acetate, and the organic layer was washed with brine, dried over anhydrous sodium sulfate, filtered and concentrated to afford 16-2.

Step 3. To a solution of 16-2 (420 mg, 1.9 mmol) in dimethylacetamide (15 mL) was added cesium carbonate (1.8 g, 5.7 mmol) and 4-amino-2,6-dichlorophenol (342 mg, 1.9 mmol). The reaction mixture was stirred at 90° C. for 2 hours under nitrogen, cooled to room temperature, and extracted with ethyl acetate. The combined organic layer was washed with water, dried over anhydrous sodium sulfate, filtered and concentrated. The residue was purified by column chromatography on silica gel (petroleum ether to petroleum ether/ethyl acetate=1:1) to afford 16-3.

Followed the similar steps in example 1 to synthesize 16. LCMS (ESI, m/z): $[M+H]^+$=463.3; HNMR (400 MHz, DMSO-$d_6$, ppm): 13.24 (br s, 1H), 12.17 (s, 1H), 7.75 (s, 2H), 7.41 (d, J=0.8 Hz, 1H), 5.12-5.08 (m, 1H), 4.08-4.02 (m, 1H), 2.97-2.85 (m, 1H), 2.65-2.43 (m, 2H), 1.89-1.71 (m, 2H).

Example 16. Synthesis of Compound 21

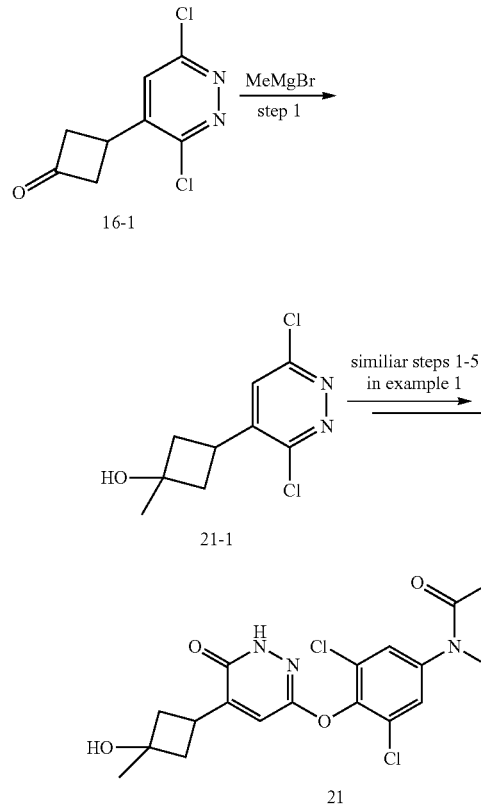

Step 1. To a solution of 16-1 (2.2 g, 10.2 mmol) in tetrahydrofuran (30 mL) was added methylmagnesium bromide (3 M in ether, 8.5 mL, 25.5 mmol) at −78° C. under nitrogen. The reaction mixture was stirred at 0° C. for 1 hour followed by quenching with a saturated aqueous ammonium chloride solution and extracted with ethyl acetate. The combined organic layer was dried over anhydrous sodium sulfate, filtered and concentrated. The residue was purified by column chromatography on silica gel (petroleum ether to petroleum ether/ethyl acetate=3:1) to afford 21-1.

Followed the similar steps in example 1 to synthesize 21. LCMS (ESI, m/z): [M+H]$^+$=477.3; HNMR (400 MHz, DMSO-d$_6$, ppm): 13.26 (br s, 1H), 12.18 (s, 1H), 7.75 (s, 2H), 7.43 (d, J=1.2 Hz, 1H), 5.00 (s, 1H), 3.05-3.00 (m, 1H), 2.30-2.25 (m, 2H), 2.09-2.03 (m, 2H), 1.30 (s, 3H).

Example 17. Synthesis of Compound 34

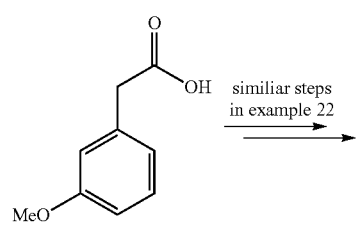

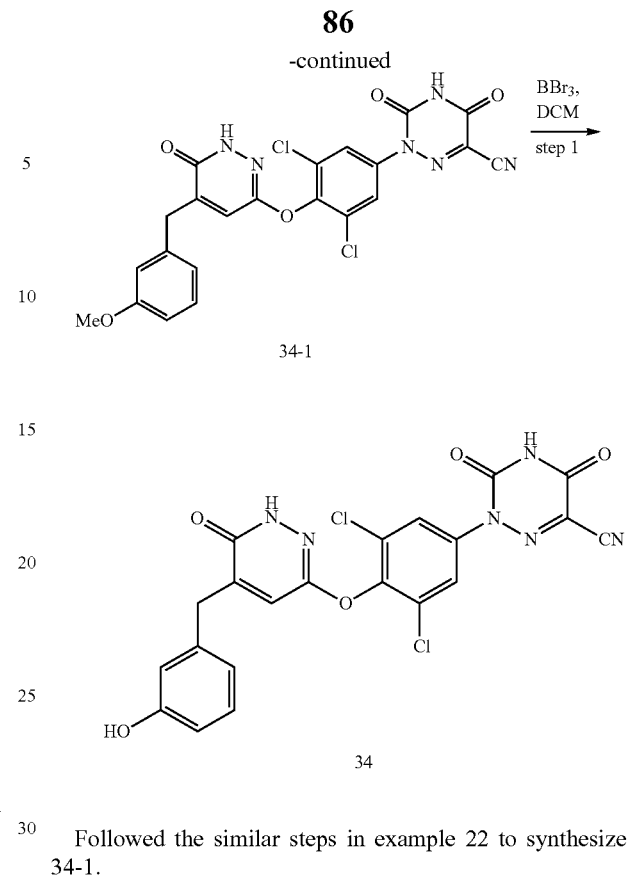

Followed the similar steps in example 22 to synthesize 34-1.

Step 1. To a solution of 34-1 (20 mg, 0.04 mmol) in dichloromethane (10 mL) was added boron tribromide (0.5 mL) at 0° C. The mixture was stirred at 0° C. for 2 hours, and then poured into ice water (10 mL). A saturated aqueous sodium bicarbonate solution was added, and the mixture was extracted with dichloromethane. The combined organic layer was washed with brine, dried over anhydrous sodium sulfate, filtered and concentrated. The residue was purified by a prep-HPLC (acetonitrile with 0.05% of aqueous trifluoroacetic acid: 20% to 95%) to afford 34. LCMS (ESI, m/z): [M+H]$^+$=499.3; HNMR (400 MHz, DMSO-d$_6$, ppm): δ 13.24 (br s, 1H), 12.29 (s, 1H), 9.36 (s, 1H), 7.74 (s, 2H), 7.29 (s, 1H), 7.10 (t, J=8.0 Hz, 1H), 6.73-6.69 (m, 2H), 6.63-6.60 (m, 1H), 3.73 (s, 2H).

Example 18. Synthesis of Compound 36

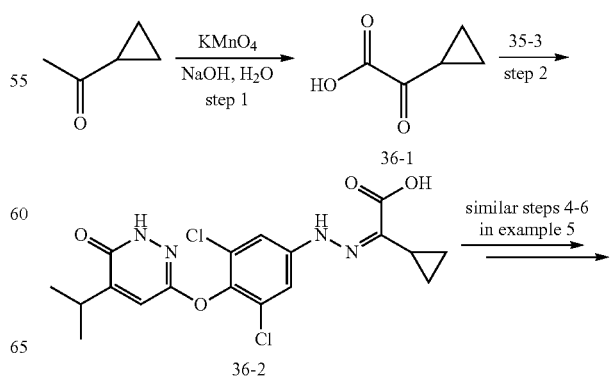

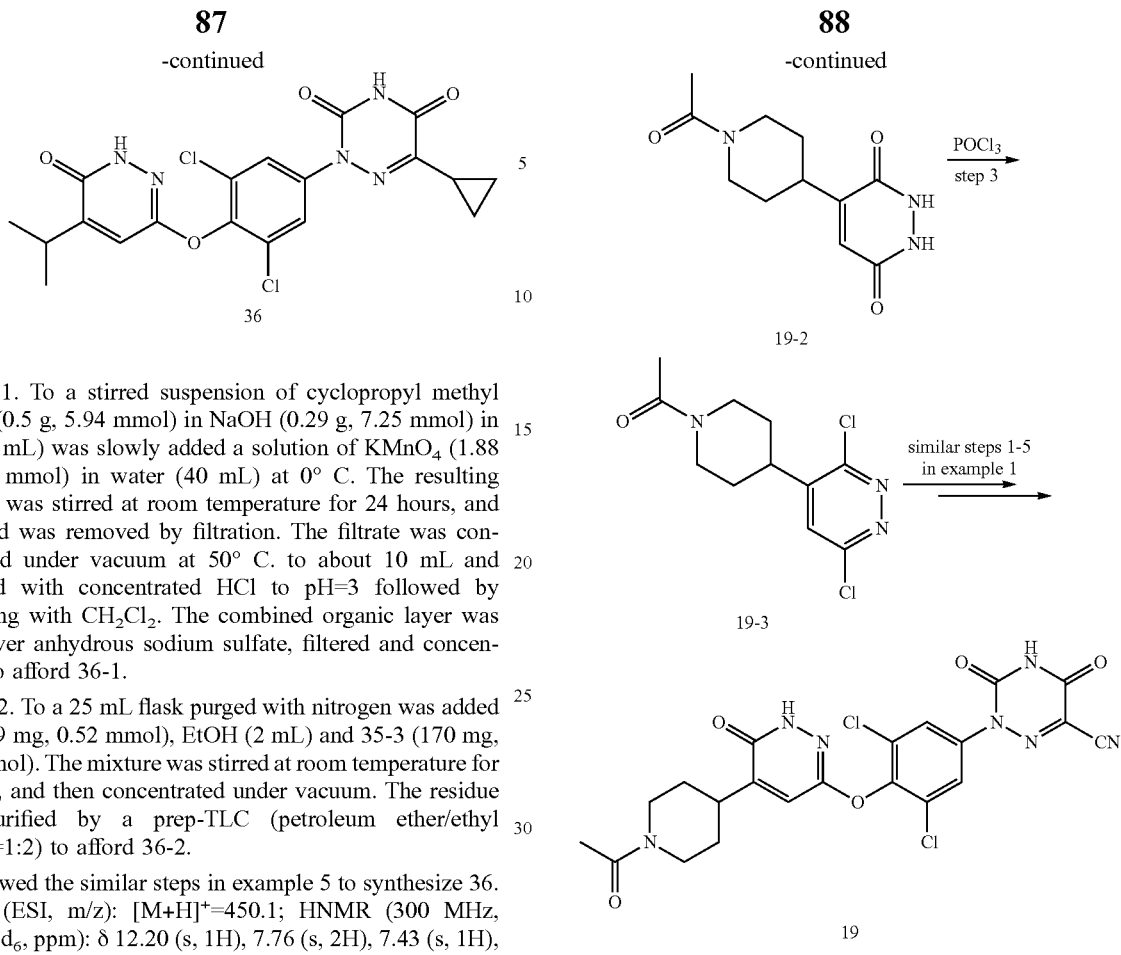

Step 1. To a stirred suspension of cyclopropyl methyl ketone (0.5 g, 5.94 mmol) in NaOH (0.29 g, 7.25 mmol) in H₂O (5 mL) was slowly added a solution of KMnO₄ (1.88 g, 11.9 mmol) in water (40 mL) at 0° C. The resulting mixture was stirred at room temperature for 24 hours, and the solid was removed by filtration. The filtrate was concentrated under vacuum at 50° C. to about 10 mL and acidified with concentrated HCl to pH=3 followed by extracting with CH₂Cl₂. The combined organic layer was dried over anhydrous sodium sulfate, filtered and concentrated to afford 36-1.

Step 2. To a 25 mL flask purged with nitrogen was added 36-1 (59 mg, 0.52 mmol), EtOH (2 mL) and 35-3 (170 mg, 0.52 mmol). The mixture was stirred at room temperature for 3 hours, and then concentrated under vacuum. The residue was purified by a prep-TLC (petroleum ether/ethyl acetate=1:2) to afford 36-2.

Followed the similar steps in example 5 to synthesize 36. LCMS (ESI, m/z): [M+H]⁺=450.1; HNMR (300 MHz, DMSO-d₆, ppm): δ 12.20 (s, 1H), 7.76 (s, 2H), 7.43 (s, 1H), 3.06-3.20 (m, 1H), 2.10-2.20 (m, 1H), 1.18-1.24 (m, 1H), 1.20 (m, 6H), 0.88-0.95 (m, 3H).

Example 19. Synthesis of Compound 19

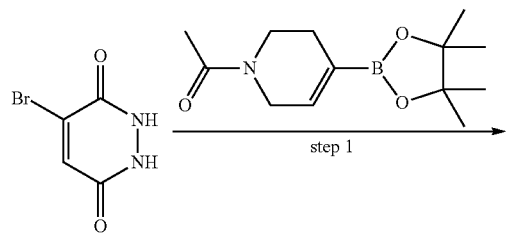

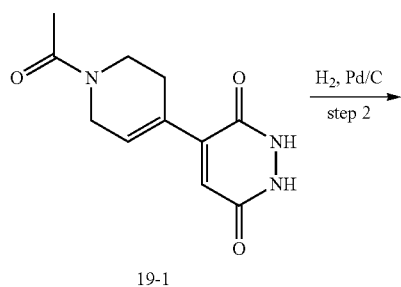

19-1

Step 1. To a 20 mL sealed tube purged with nitrogen was charged with 4-bromo-1,2,3,6-tetrahydropyridazine-3,6-dione (500 mg, 2.62 mmol), 1-[4-(4,4,5,5-tetramethyl-1,3,2-dioxaborolan-2-yl)-1,2,3,6-tetrahydropyridin-1-yl]ethan-1-one (789 mg, 3.142 mmol), K₂CO₃ (729 mg, 5.24 mmol), 1,2-dimethoxyethane (8 mL), H₂O (2 mL) and Pd(dtbpf)Cl₂ (171 mg, 0.26 mmol). The reaction mixture was irradiated under microwave at 100° C. for 1 hour. The mixture was cooled to room temperature, filtered, and concentrated. The residue was purified by a reversed phase column chromatography with 0.1% of aqueous formic acid-acetonitrile (20% to 40% gradient in 5 min.) to afford 19-1.

Step 2. To a 250 mL flask purged with nitrogen was charged with 19-1 (1.0 g, 4.25 mmol), 10% Pd/C (150 mg, 1.41 mmol) and NMP (60 mL). The resulting mixture was stirred under H₂ atmosphere at room temperature for 2 hours. The mixture was filtered and the filtrate was concentrated to afford 19-2.

Step 3. To a 40 mL flask was charged with 19-2 (1.0 g, 4.22 mmol) and POCl₃ (10 mL), and the resulting solution was stirred at 120° C. for 3 hours. The mixture was cooled to room temperature, quenched with ice-water, and extracted with ethyl acetate. The combined organic layer was dried over anhydrous sodium sulfate, filtered and concentrated under vacuum. The residue was purified by column chromatography on silica gel (ethyl acetate/petroleum ether=1:2) to afford 19-3.

Followed the similar steps in example 1 to synthesize 19. LCMS (ESI, m/z): [M+H]⁺=517.9; HNMR (300 MHz, DMSO-d₆, ppm): δ 13.26 (br s, 1H), 12.30 (s, 1H), 7.78 (s, 2H), 7.45 (s, 1H), 4.52-4.56 (m, 1H), 3.91-3.95 (m, 1H), 2.96-3.54 (m, 2H), 2.59-2.81 (m, 1H), 2.03 (s, 3H), 1.81-1.89 (m, 2H), 1.49-1.62 (m, 2H).

Example 20. Synthesis of Compound 47

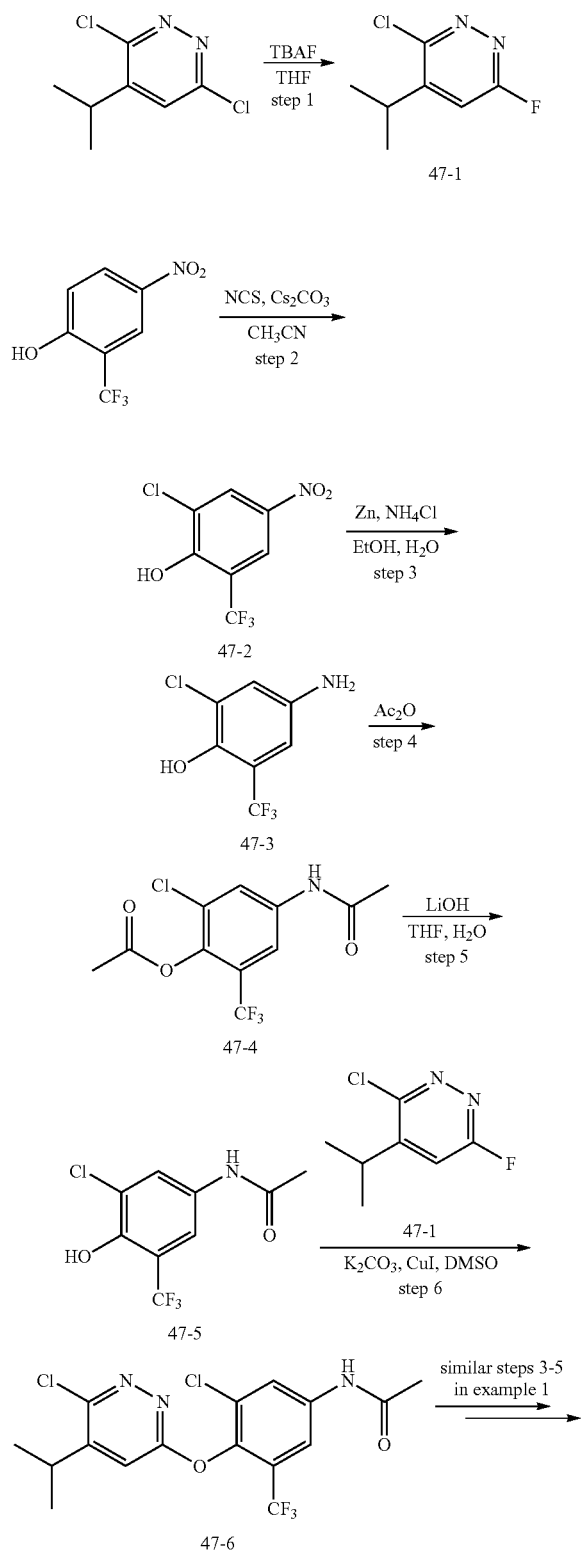

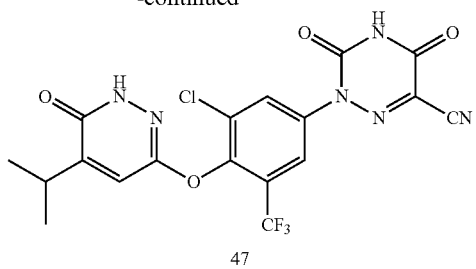

Step 1. A solution of 3,6-dichloro-4-(propan-2-yl)pyridazine (5.0 g, 26.17 mmol) in TBAF (1.0 M in THF, 78.5 mL) was heated at 50° C. overnight. Then TBAF (1.0 M in THF, 13.0 mL) was added and the mixture was heated at 60° C. for another 2 hours. The reaction mixture was then cooled to room temperature followed by quenching with water. The resulting solution was extracted with ethyl acetate and the combined organic layer was dried over anhydrous sodium sulfate, filtered and concentrated under vacuum. The residue was purified by column chromatography on silica gel (ethyl acetate/petroleum ether=1:5) to afford 47-1.

Step 2. To a suspension of 4-nitro-2-(trifluoromethyl)phenol (5.00 g, 24.14 mmol) and $Cs_2CO_3$ (15.73 g, 48.28 mmol) in $CH_3CN$ (50 mL) was added NCS (9.67 g, 72.43 mmol). The resulting mixture was stirred at 80° C. for 3 hours. The solution was concentrated under vacuum to remove the solvent, and water (100 mL) was added. The resulting solution was extracted with ethyl acetate and the combined organic layer was washed with brine, dried over anhydrous sodium sulfate, filtered and concentrated under vacuum. The residue was purified by column chromatography on silica gel (ethyl acetate/petroleum ether=3:10) to afford 47-2.

Step 3. To a solution of 47-2 (3.00 g, 12.42 mmol) and $NH_4Cl$ (6.64 g, 124.20 mmol) in $H_2O$ (15 mL) and EtOH (30 mL) was added Zn powder (4.06 g, 62.10 mmol). The resulting mixture was stirred at room temperature overnight followed by filtration. The filtrate was extracted with ethyl acetate and the combined organic layer was dried over anhydrous sodium sulfate, filtered and concentrated under vacuum to afford 47-3 which was used in next step without further purification.

Step 4. A solution of 47-3 (1.40 g, 6.62 mmol) in $Ac_2O$ (10 mL) was heated at 100° C. for 2 hours. Then the reaction mixture was cooled to room temperature followed by quenching with water (50 mL). The resulting solution was extracted with ethyl acetate, and the combined organic layer was washed with saturated aqueous $NaHCO_3$ solution, dried over anhydrous sodium sulfate, filtered and concentrated under vacuum to afford 47-4 which was used in next step without further purification.

Step 5. To a solution of 47-4 (1.40 g, 4.74 mmol) in THF (14 mL) and $H_2O$ (7 mL) was added $LiOH \cdot H_2O$ (0.40 g, 9.471 mmol). The resulting solution was stirred at room temperature for 2 hours, followed by diluting with water. The mixture was extracted with ethyl acetate, and the combined organic layer was dried over anhydrous sodium sulfate, filtered and concentrated under vacuum to afford 47-5 which was used in next step without further purification.

Step 6. To s solution of 47-5 (1.14 g, 4.50 mmol) in DMSO (10 mL) was added 47-1 (1.96 g, 11.24 mmol), $K_2CO_3$ (1.24 mg, 8.99 mmol) and CuI (514 mg, 2.70 mmol).

The resulting solution was heated at 90° C. for overnight. The reaction mixture was cooled to room temperature followed by quenching with water. The resulting solution was extracted with ethyl acetate, and the combined organic layer was dried over anhydrous sodium sulfate, filtered and concentrated under vacuum. The residue was purified by column chromatography on silica gel (ethyl acetate/petroleum ether=1:2) to afford 47-6.

Followed the similar steps in example 1 to synthesize 47. LCMS (ESI, m/z): [M+H]$^+$=469.1; HNMR (300 MHz, DMSO-d$_6$, ppm): δ 13.37 (br s, 1H), 12.28 (s, 1H), 8.13 (s, 1H), 7.97 (s, 1H), 7.45 (s, 1H), 3.10-3.00 (m, 1H), 1.20 (d, J=6.6 Hz, 6H).

Example 21. Synthesis of Compound 56

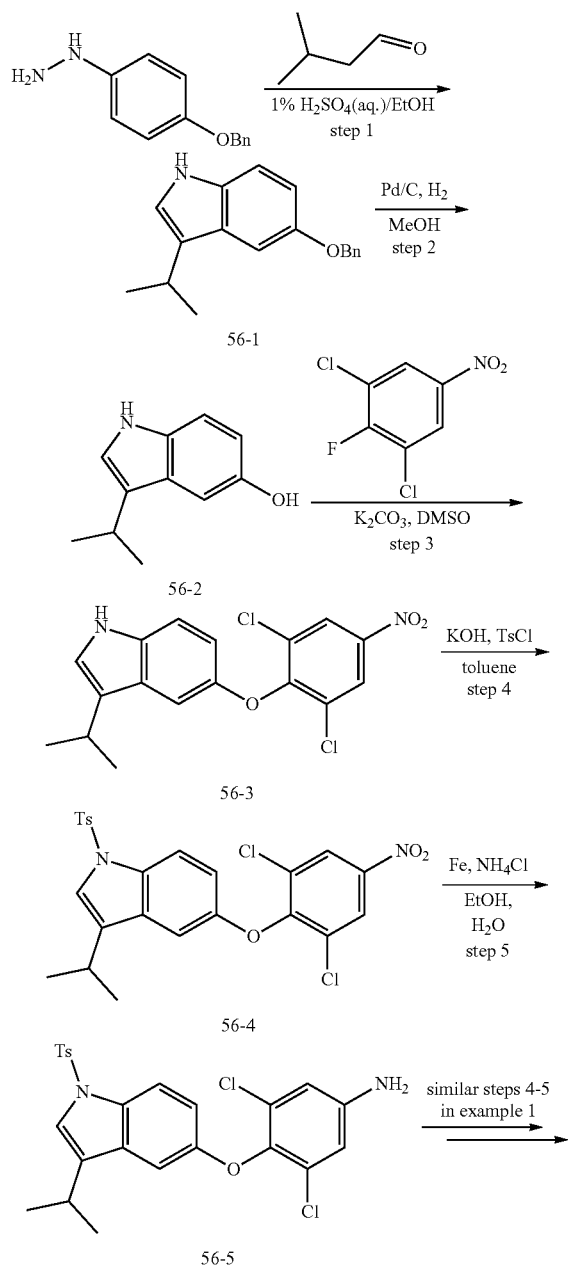

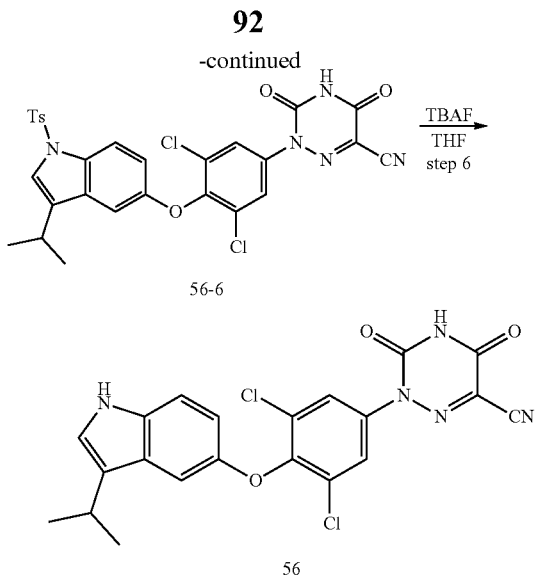

Step 1. To a solution of 4-(benzyloxy)phenylhydrazine (10.0 g, 46.67 mmol) and 3-methylbutanal (4.02 g, 46.67 mmol) in EtOH (100 mL) was added 1% H$_2$SO$_4$ (66 mL) dropwise at 0° C. under nitrogen atmosphere. The mixture was stirred at 80° C. for 3 hours and then cooled to room temperature. The mixture was partially concentrated under reduced pressure, and then extracted with ethyl acetate. The combined organic layer was washed with brine, dried over anhydrous sodium sulfate, filtered and concentrated under vacuum. The residue was purified by silica gel column chromatography with ethyl acetate/petroleum ether (1/8) to afford 56-1.

Step 2. To a solution of 56-1 (4.0 g, 15.07 mmol) in MeOH (120 mL) was added 10% Pd/C (0.4 g) under nitrogen atmosphere. The resulting mixture was stirred under H$_2$ atmosphere at room temperature for 16 hour, filtered, and the filtrate was concentrated under reduced pressure. The residue was purified by silica gel column chromatography with ethyl acetate/petroleum ether (1:3) to afford 56-2.

Step 3. To a solution of 56-2 (322 mg, 1.84 mmol) in DMSO (3.2 mL) was added 1,3-dichloro-2-fluoro-5-nitrobenzene (425 mg, 2.02 mmol) and K$_2$CO$_3$ (508 mg, 3.68 mmol) at room temperature. The mixture was heated at 125° C. under nitrogen atmosphere for 2 hours. The resulting mixture was then cooled to room temperature and filtered. The filtrated was diluted with ethyl acetate, washed with brine, dried over anhydrous sodium sulfate, filtered and concentrated under vacuum. The residue was purified by silica gel column chromatography with ethyl acetate/petroleum ether (1:50) to afford 56-3.

Step 4. To a solution of 56-3 (600 mg, 1.64 mmol) in toluene (6 mL) was added p-TsCl (376 mg, 1.97 mmol) in toluene (3 mL), 50% aqueous KOH (6 mL), and Bu$_4$NHSO$_4$ (56 mg, 0.16 mmol) at 0° C. The mixture was allowed to warm to room temperature and stirred for 16 hours, and water (25 mL) was added. The mixture was extracted with ethyl acetate, and the combined organic layer was washed with brine, dried over anhydrous sodium sulfate, filtered and concentrated under vacuum. The residue was purified by silica gel column chromatography ethyl acetate/petroleum ether (1:60) to afford 56-4.

Step 5. To a suspension of 56-4 (1.07 g, 2.06 mmol) in EtOH (22 mL) and H$_2$O (11 mL) was added NH$_4$Cl (882 mg, 16.48 mmol) and iron powder (575 mg, 10.30 mmol) portion wise. The resulting mixture was stirred at 50° C. under nitrogen atmosphere for 2 hours, cooled to room temperature and filtered. The filtrated was extracted with ethyl acetate, washed with brine, dried over anhydrous sodium sulfate, filtered and concentrated under vacuum. The residue was purified by silica gel column chromatography with ethyl acetate/petroleum ether (1:6) to afford 56-5.

Followed the similar steps in example 1 to synthesize 56-6.

Step 6. To a stirred solution of 56-6 (190 mg, 0.31 mmol) in THF (4 mL) was added TBAF (1 M in THF, 4.0 mL) in portions at room temperature under nitrogen atmosphere. The resulting mixture was heated at 65° C. under nitrogen atmosphere for 48 hours, followed by cooling and quenching with water (20 mL). The resulting mixture was extracted with ethyl acetate, and the combined organic layer was washed with brine, dried over anhydrous sodium sulfate, filtered and concentrated under vacuum. The residue was purified by a prep-HPLC with 0.05% aqueous $NH_3 \cdot H_2O$/ acetonitrile to afford 56. LCMS (ESI, m/z): $[M+H]^+=455.8$; HNMR (300 MHz, DMSO-$d_6$, ppm): δ 10.79 (s, 1H), 7.80 (s, 2H), 7.30 (d, J=8.7 Hz, 1H), 7.11-7.12 (m, 1H), 6.90 (s, 1H), 6.67 (dd, J=8.7, 2.5 Hz, 1H), 2.98-3.03 (m, 1H), 1.22-1.24 (d, J=6.9 Hz, 6H).

Example 22. Synthesis of Compound 58

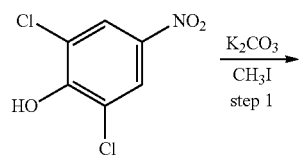

step 1

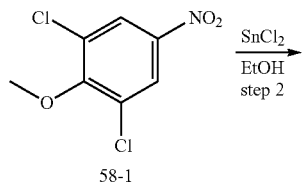

58-1

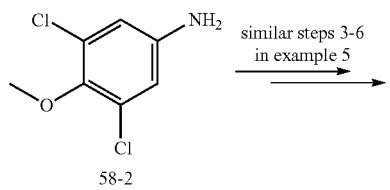

58-2

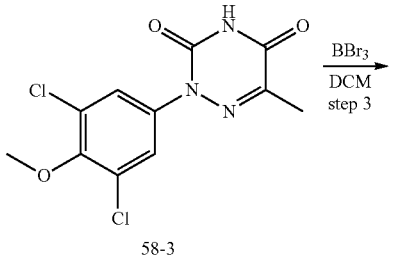

58-3

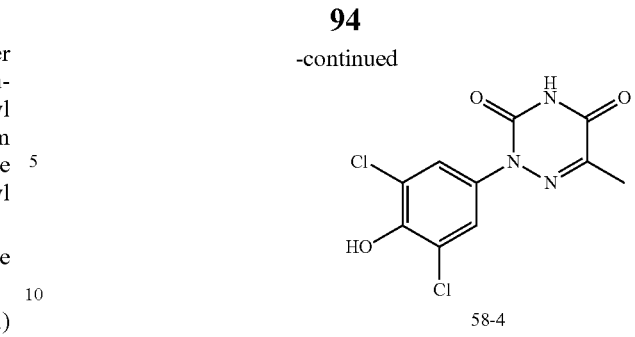

58-4

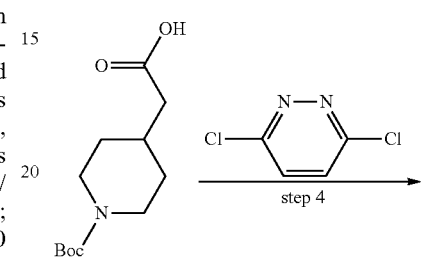

step 4

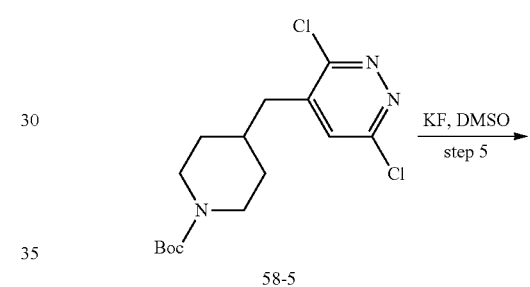

58-5

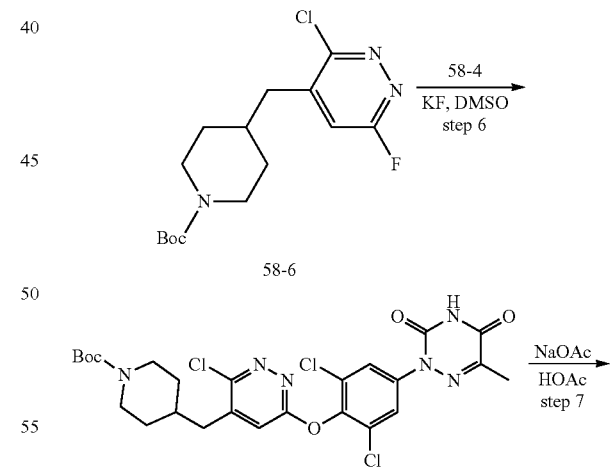

58-6

58-7

58-8

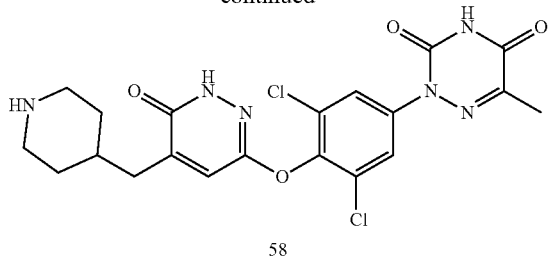

58

Step 1. To a suspension of 2,6-dichloro-4-nitrophenol (41.6 g, 200 mmol) and potassium carbonate (110.4 g, 800 mmol) in dimethylformamide (200 mL) was added iodomethane (56.8 g, 400 mmol) at 0° C. The mixture was stirred at 60° C. for 1.5 hours, followed by cooling to room temperature and quenching with water (1 L). The resulting slurry was stirred for 10 minutes and filtered. The filter cake was washed with water and dried to afford 58-1.

Step 2. To a solution of 58-1 (18 g, 81 mmol) in ethanol (250 mL) was added stannous chloride (76.8 g, 405 mmol) portion wise at room temperature. The resulting mixture was heated at 80° C. for 2 hours, cooled to room temperature, and poured into ice-water (500 mL). The solution was adjusted to about pH=9 with a 2 N of aqueous sodium hydroxide solution and filtered through Celite. The filtrate was extracted with ethyl acetate, and the combined organic layer was washed with brine, dried over sodium sulfate, filtered and concentrated to afford 58-2.

Followed the similar steps in example 5 to synthesize 58-3.

Step 3. To a solution of 58-3 (178 mg, 0.59 mmol) in dichloromethane (5 mL) was added boron tribromide (0.2 mL) at 0° C. The mixture was stirred at 0° C. for 1 hour, followed by quenching with a saturated aqueous sodium bicarbonate solution at 0° C. and adjusted to pH=5 with HCl (1 M). The mixture was filtered and the solid was dried to afford 58-4.

Step 4. To a suspension of 3,6-dichloropyridazine (455 mg, 3.0 mmol), 2-(1-(tert-butoxycarbonyl) piperidin-4-yl) acetic acid (970 mg, 4.0 mmol), silver nitrate (510 mg, 3.0 mmol) and trifluoroacetic acid (68 mg, 0.6 mmol) in acetonitrile (20 mL) and water (20 mL) was added a solution of ammonium persulfate (1.37 g, 6 mmol) at 65° C. Then the reaction mixture was heated at 75° C. for 2 hours, followed by cooling to room temperature and neutralization with $NH_3 \cdot H_2O$. The mixture was extracted with ethyl acetate, and the combined organic layer was washed with water and brine, dried over sodium sulfate, filtered and concentrated. The residue was purified by column chromatography on silica gel with ethyl acetate to ethyl acetate/petroleum ether=0 to 30% to afford 58-5.

Step 5. A mixture of 58-5 (500 mg, 1.45 mmol) and potassium fluoride (336 mg, 5.8 mmol) in dimethyl sulfoxide (40 mL) was heated at 120° C. for overnight. After cooled to room temperature, the reaction mixture was diluted with ethyl acetate, washed with water and brine, dried over sodium sulfate, filtered and concentrated. The residue was purified by column chromatography on silica gel (ethyl acetate to ethyl acetate/petroleum ether=0 to 30%) to afford 58-6.

Step 6. To a solution of 58-6 (234 mg, 0.71 mmol) and 58-4 (68 mg, 0.24 mmol) in dimethyl sulfoxide (40 mL) was added potassium fluoride (84 mg, 1.44 mmol) at room temperature. The reaction mixture was heated at 100° C. for 2 days. After cooled to room temperature, the reaction mixture was diluted with ethyl acetate, washed with water and brine, dried over sodium sulfate, filtered and concentrated. The residue was purified by column chromatography on silica gel (ethyl acetate to ethyl acetate/petroleum ether=0 to 70%) to afford 58-7.

Step 7. To a solution of 58-7 (50 mg, 0.084 mmol) in acetic acid (5 mL) was added sodium acetate (27 mg, 0.34 mmol) at room temperature, and the mixture was then heated at 100° C. for overnight. After cooled to room temperature, the reaction mixture was poured into water and extracted with dichloromethane. The combined organic layer was washed with brine, dried over sodium sulfate, filtered and concentrated to afford 58-8, which was used to the next step without further purification.

Step 8. To a solution of 58-8 (30 mg, 0.052 mmol) in dichloromethane (4 mL) was added trifluoroacetic acid (59 mg, 0.52 mmol) at room temperature. The reaction mixture was stirred at room temperature for 2 hours, and then concentrated. The residue was purified by a prep-HPLC (acetonitrile with 0.05%TFA in water: 25% to 50%) to afford 58. LCMS (ESI, m/z): $[M+H]^+$=479.4. HNMR (400 MHz, $CD_3OD$): δ 7.76 (s, 2H), 7.45 (s, 1H), 3.40-3.37 (m, 2H), 3.00-2.94 (m, 2H), 2.62 (d, J=6.8 Hz, 2H), 2.24 (s, 3H), 2.12-2.07 (m, 1H), 1.95-1.92 (m, 2H), 1.54-1.43 (m, 2H).

Example 23. Synthesis of Compound 70

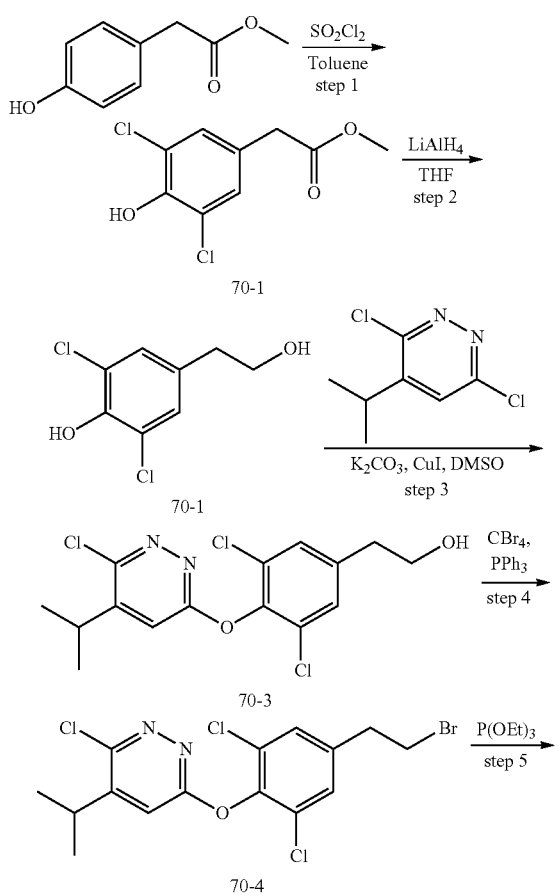

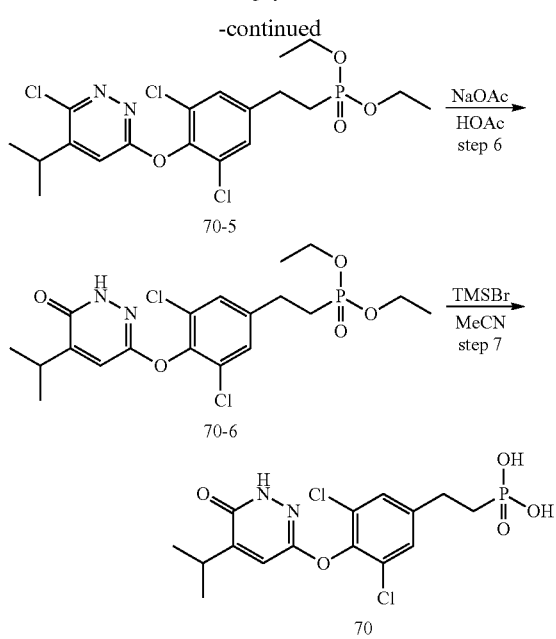

Step 1. To a solution of methyl 2-(4-hydroxyphenyl) acetate (5 g, 30 mmol) and diisobutylamine (388 mg, 3.0 mmol) in toluene (50 mL) was added a solution of sulfuryl dichloride (8.1 g, 60 mmol) in toluene (15 mL) dropwise at 70° C. under N₂ atmosphere. The mixture was then stirred at 70° C. for 1 hour, and poured into water and extracted with ethyl acetate. The combined organic layer was washed with brine, dried over sodium sulfate, filtered and concentrated to afford 70-1.

Step 2. To a solution of 70-1 (4.9 g, 20.94 mmol) in tetrahydrofuran (100 mL) was added LiAlH₄ (8.4 mL, 2.5 M in tetrahydrofuran, 20.94 mmol) dropwise at −10° C. under N₂ atmosphere. The mixture was then stirred at −10° C. for 15 minutes, followed by quenching with water and a 15% aqueous sodium hydroxide solution at 0° C. The mixture was diluted with ethyl acetate and filtered. The filtered cake was rinsed with ethyl acetate and the filtrate was washed with aqueous hydrochloric acid (1N), water (50 mL) and brine (50 mL), dried over sodium sulfate, filtered and concentrated to afford 70-2.

Step 3. A mixture of 70-2 (2.75 g, 13.35 mmol), 3,6-dichloro-4-(propan-2-yl)pyridazine (3.06 g, 16.02 mmol), potassium carbonate (3.68 g, 26.70 mmol), and cuprous iodide (1.27 g, 6.68 mmol) in dimethyl sulfoxide (14 mL) was stirred at 90° C. for 4 hours under N₂ atmosphere. Then the reaction mixture was poured into water and extracted with ethyl acetate. The combined organic layer was washed with brine, dried over sodium sulfate, filtered and concentrated. The residue was purified by column chromatography on silica gel (petroleum ether to petroleum ether/ethyl acetate=1:1) to give a crude product, which was slurried with ether at 0° C. The slurry was filtered and the filtered cake was washed with ether and dried to give 70-3.

Step 4. To a solution of 70-3 (600 mg, 1.66 mmol) and triphenylphosphine (653 mg, 2.49 mmol) in dichloromethane (10 mL) was added CBr₄ (815 mg, 2.49 mmol) at room temperature. The mixture was stirred for 1 hour, and then concentrated to give a residue which was purified by column chromatography on silica gel (petroleum ether to petroleum ether/ethyl acetate=1:1) to afford 70-4.

Step 5. A mixture of 70-4 (300 mg, 0.71 mmol) in triethyl phosphite (1 mL) was heated at 130° C. for 5 hours, and then concentrated to give a residue which was purified by column chromatography on silica gel (petroleum ether to petroleum ether/ethyl acetate=1:1) to afford 70-5.

Step 6. To a solution of 70-5 (250 mg, 0.52 mmol) in acetic acid (2 mL) was added sodium acetate (255 mg, 3.11 mmol) at room temperature. The mixture was heated at 120° C. for 16 hours, and then poured into water and filtered. The filtered cake was dried to afford 70-6.

Step 7. To a solution of 70-6 (190 mg, 0.41 mmol) in acetonitrile (3 mL) was added bromo(trimethyl)silane (0.5 mL) at room temperature. The mixture was heated at 70° C. for 3 hours, and then poured into water and filtered. The filtered cake was purified by a prep-HPLC (acetonitrile with 0.05%TFA in water: 15% to 95%) to afford 70. LCMS (ESI, m/z): 407.3 [M+H]⁺. HNMR (400 MHz, DMSO-d₆, ppm): δ 12.15 (s, 1H), 7.45 (s, 2H), 7.33 (d, J=0.8 Hz, 1H), 3.05-2.94 (m, 1H), 2.80-2.73 (m, 2H), 1.88-1.79 (m, 2H), 1.14 (d, J=6.8 Hz, 6H).

Example 24. Synthesis of Compound 71 and 72

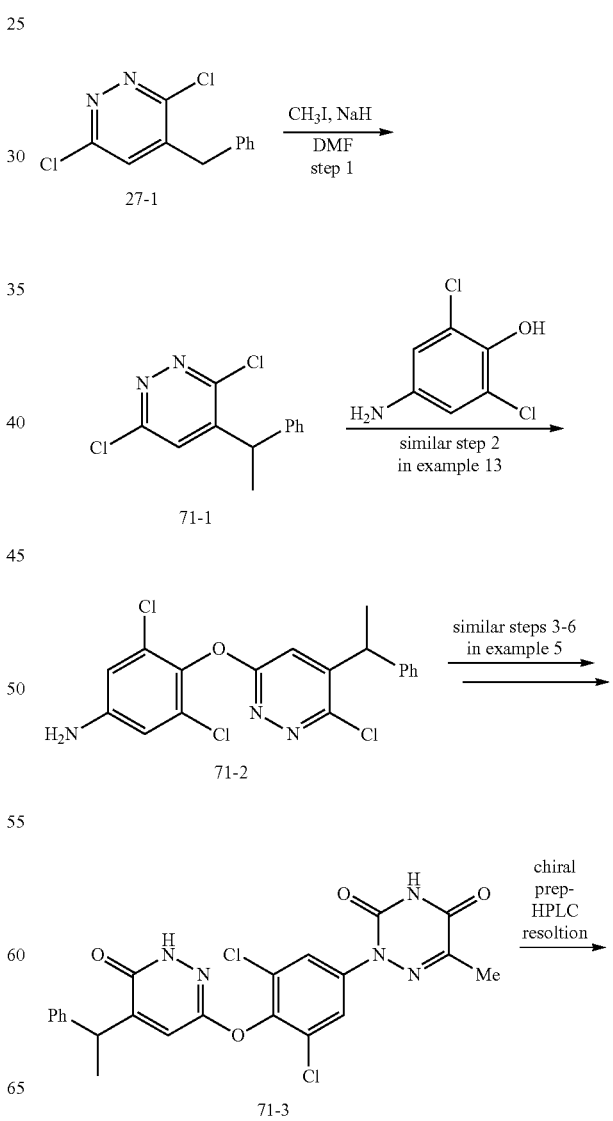

-continued

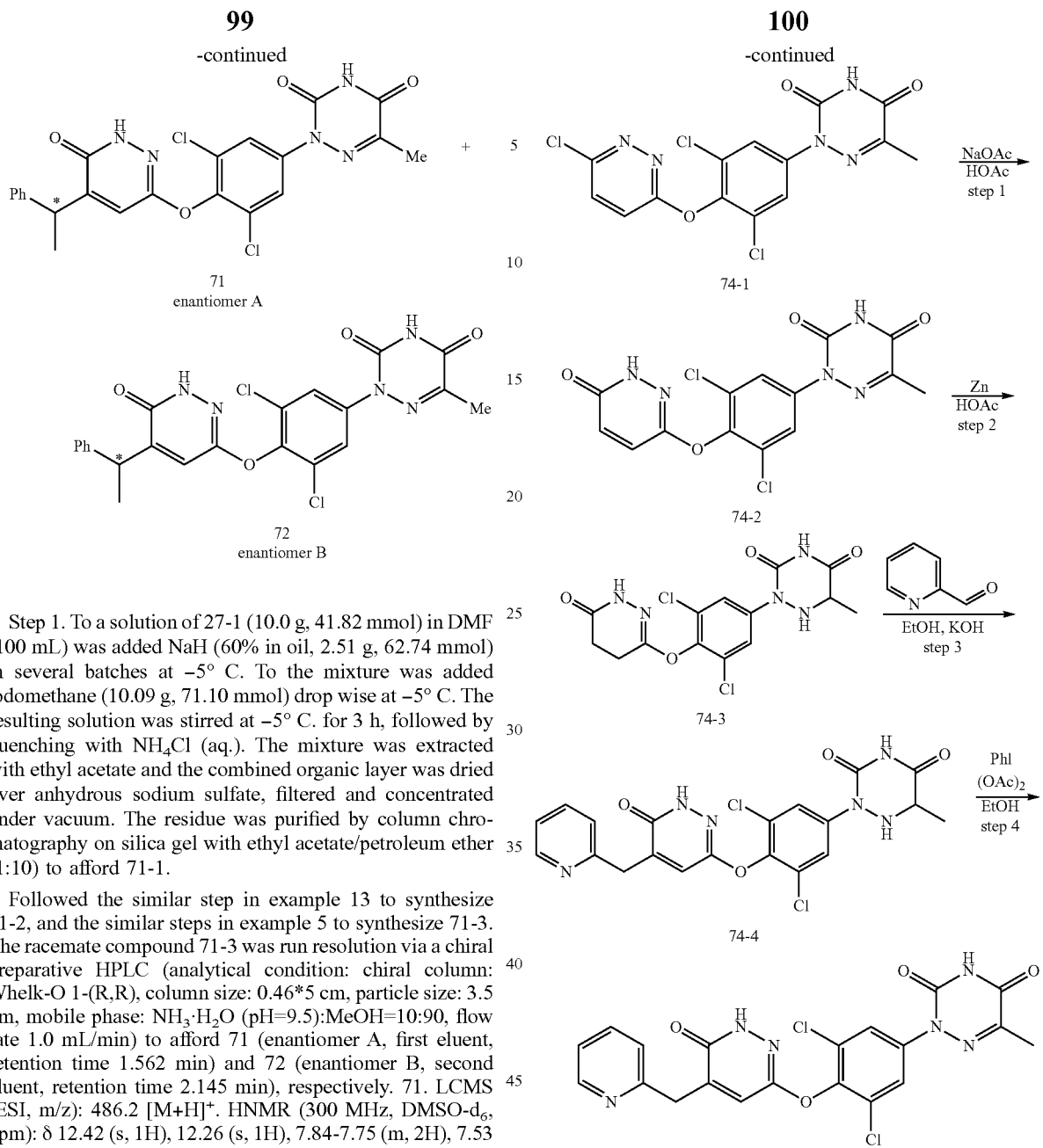

Step 1. To a solution of 27-1 (10.0 g, 41.82 mmol) in DMF (100 mL) was added NaH (60% in oil, 2.51 g, 62.74 mmol) in several batches at −5° C. To the mixture was added iodomethane (10.09 g, 71.10 mmol) drop wise at −5° C. The resulting solution was stirred at −5° C. for 3 h, followed by quenching with NH$_4$Cl (aq.). The mixture was extracted with ethyl acetate and the combined organic layer was dried over anhydrous sodium sulfate, filtered and concentrated under vacuum. The residue was purified by column chromatography on silica gel with ethyl acetate/petroleum ether (1:10) to afford 71-1.

Followed the similar step in example 13 to synthesize 71-2, and the similar steps in example 5 to synthesize 71-3. The racemate compound 71-3 was run resolution via a chiral preparative HPLC (analytical condition: chiral column: Whelk-O 1-(R,R), column size: 0.46*5 cm, particle size: 3.5 um, mobile phase: NH$_3$·H$_2$O (pH=9.5):MeOH=10:90, flow rate 1.0 mL/min) to afford 71 (enantiomer A, first eluent, retention time 1.562 min) and 72 (enantiomer B, second eluent, retention time 2.145 min), respectively. 71. LCMS (ESI, m/z): 486.2 [M+H]$^+$. HNMR (300 MHz, DMSO-d$_6$, ppm): δ 12.42 (s, 1H), 12.26 (s, 1H), 7.84-7.75 (m, 2H), 7.53 (s, 1H), 7.34-7.43 (m 4H), 7.25 (s, 1H), 4.35-4.22 (m, 1H), 2.16 (s, 3H), 1.61-1.44 (m, 3H). 72. LCMS (ESI, m/z): 486.2 [M+H]$^+$. HNMR (300 MHz, DMSO-d$_6$, ppm): δ 12.42 (s, 1H), 12.26 (s, 1H), 7.86-7.74 (m, 2H), 7.53 (s, 1H), 7.34-7.43 (m 4H), 7.25 (s, 1H), 4.38-4.24 (m, 1H), 2.16 (s, 3H), 1.61-1.44 (m, 3H).

Example 25. Synthesis of Compound 74

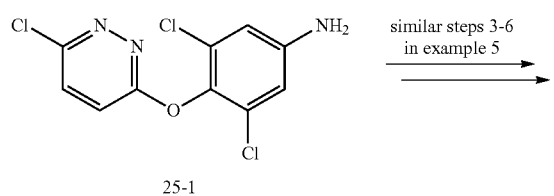

Followed the similar steps in example 5 to synthesize 74-1.

Step 1. To a solution of 74-1 (1.6 g, 4 mmol) in acetic acid (20 mL) was added sodium acetate (1.64 g, 20 mmol) at room temperature. The mixture was heated at 120° C. for 8 hours, and then poured into water and filtered. The filtered cake was washed with water and dried to afford 74-2.

Step 2. To a suspension of 74-2 (305 mg, 0.8 mmol) in acetic acid (20 mL) was added zinc powder (780 mg, 12 mmol). Then the mixture was heated at 85° C. for 48 hours under N$_2$ atmosphere. After cooled to room temperature, the reaction mixture was diluted with water, and extracted with dichloromethane. The combined organic layer was dried over sodium sulfate, filtered and concentrated to afford 74-3.

Step 3. A mixture of 74-3 (200 mg, 0.5 mmol), 2-pyridinecarboxaldehyde (80 mg, 0.75 mmol), and potassium hydroxide (140 mg, 2.5 mmol) in ethanol (10 mL) was heated at 80° C. for 1 hour under $N_2$ atmosphere. After cooled to room temperature, the mixture was neutralized to pH~4 with acetic acid, diluted with water, and extracted with dichloromethane. The combined organic layer was dried over sodium sulfate, filtered and concentrated. The residue was purified by a prep-TLC (dichloromethane/methanol=10:1) to afford 74-4.

Step 4. To a solution of 74-4 (25 mg, 0.05 mmol) in ethanol (30 mL) was added (diacetoxyiodo)benzene (32 mg, 0.1 mmol) at room temperature. The mixture was stirred for 24 hours, and then concentrated to a residue which was purified by a prep-HPLC (acetonitrile with 0.05%TFA in water: 12% to 95%) to afford 74. LCMS (ESI, m/z): 473.3 [M+H]$^+$. HNMR (400 MHz, DMSO-d$_6$, ppm): δ 12.38 (s, 1H), 12.32 (s, 1H), 8.56 (d, J=4.8 Hz, 1H), 7.92-7.88 (m, 1H), 7.76 (s, 2H), 7.49 (d, J=8.0 Hz, 1H), 7.44 (s, 1H), 7.41-7.37 (m, 1H), 4.06 (s, 2H), 2.12 (s, 3H).

Example 26. Synthesis of Compound 73

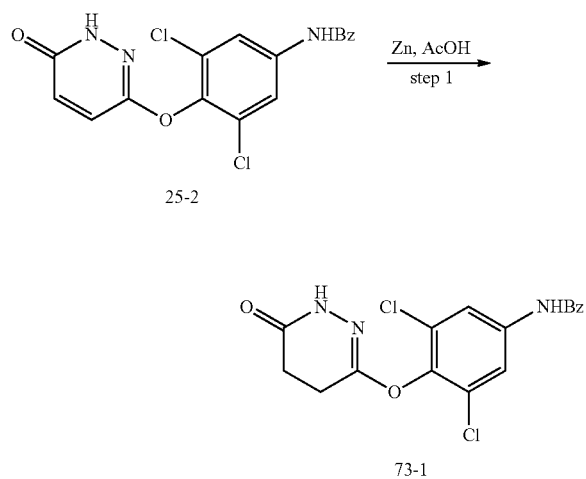

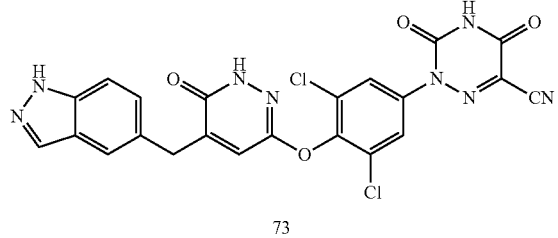

Step 1. To a suspension of 25-2 (4.5 g, 12 mmol) in acetic acid (150 mL) was added zinc powder (4.6 g, 70 mmol). The mixture was then heated to 80° C. for 3 hours. After cooled to room temperature, the reaction mixture was diluted with ethyl acetate, and the organic layer was washed with water, an aqueous NaHCO$_3$ solution and brine, and then dried over sodium sulfate, filtered and concentrated to afford 73-1.

Step 2. To a suspension of 1H-indazole-5-carbaldehyde (1.46 g, 10 mmol) in dichloromethane (100 mL) was added an aqueous potassium hydroxide solution (50%, 20 mL) at 0° C., followed by tetrabutylammonium bromide (32 mg, 0.1 mmol) and 2-(trimethylsilyl)ethoxymethyl chloride (2.13 mL, 12 mmol). The mixture was stirred at 0° C. for 4 hours under $N_2$ atmosphere. Then the mixture was washed with water and brine, dried over anhydrous sodium sulfate, filtered and concentrated. The residue was purified by flash column chromatography on silica gel (petroleum ether to dichloromethane/petroleum ether=1:1) to afford 73-2.

Step 3. To a solution of 73-2 (440 mg, 1.6 mmol) in ethanol (10 mL) was added 73-1 (500 mg, 1.3 mmol) and potassium hydroxide (260 mg, 3.9 mmol) at room temperature. The mixture was heated at 80° C. overnight under $N_2$ atmosphere. Then aqueous potassium hydroxide (50%, 10 mL) was added, and the mixture was heated at 90° C. for 5 hours and then concentrated. The residue was diluted with dichloromethane, neutralized with acetic acid to pH~3 and separated. The organic layer was washed with water and brine, dried over sodium sulfate, filtered and concentrated. The residue was purified by column chromatography on silica gel (dichloromethane to ethyl acetate/dichloromethane=1:1) to give 73-3.

Followed the similar steps in example 1 to synthesize 73. LCMS (ESI, m/z): 523.3 [M+H]$^+$. HNMR (400 MHz, DMSO-d$_6$, ppm): δ 13.26 (br s, 1H), 13.01 (s, 1H), 12.30 (s, 1H), 8.01 (s, 1H), 7.73 (s, 2H), 7.69 (s, 1H), 7.49 (d, J=8.4 Hz, 1H), 7.32 (dd, J=8.8 Hz, 1.6 Hz, 1H), 7.28 (s, 1H), 3.92 (s, 2H)

Example 27. Synthesis of Compound 80

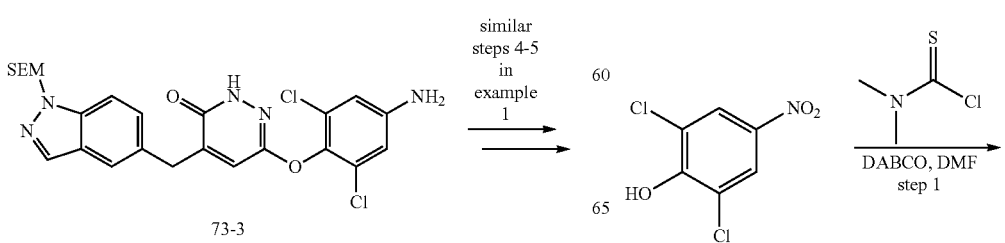

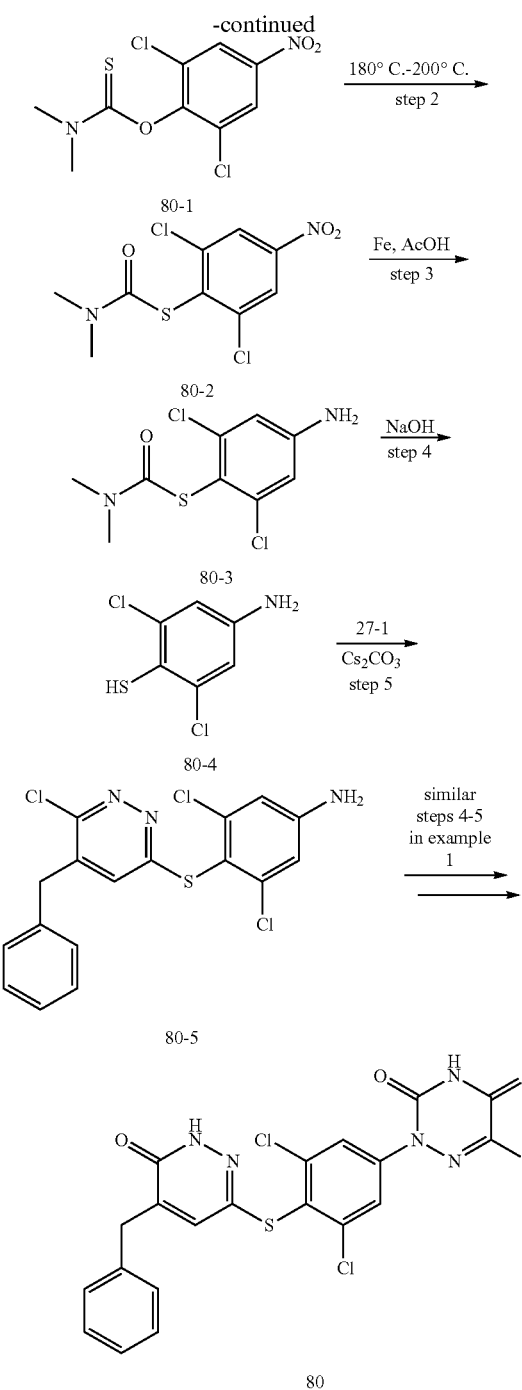

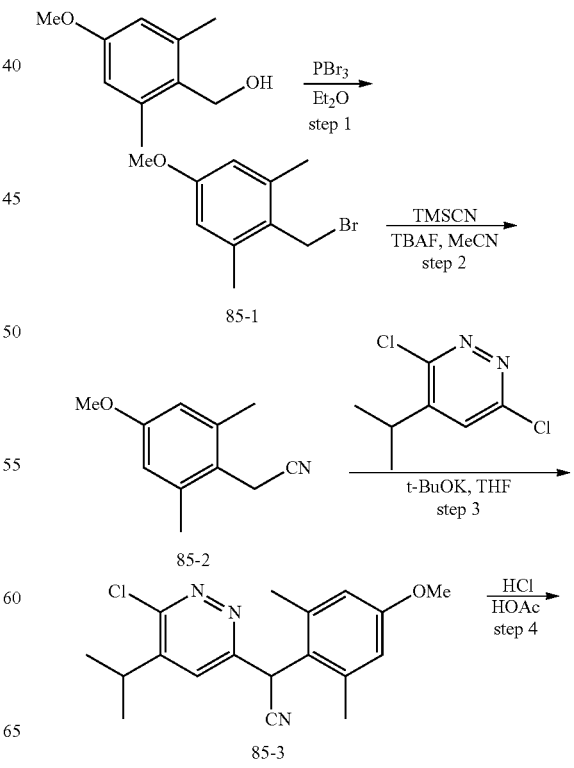

Step 3. A mixture of 80-2 (5.0 g, 17 mmol) in acetic acid (30 mL), 2-propanol (60 mL), and water (30 mL) was heated to 50° C., and then iron powder (2.63 g, 47.3 mmol) was added. The resulting mixture was heated to 95° C. for 2 hours. Then the reaction mixture was filtered through a pad of celite and the filtered cake was washed with hot water and ethyl acetate. The filtrates were concentrated, diluted with water and neutralized to pH=8 with ammonium hydroxide. The mixture was extracted with ethyl acetate, and the combined organic layer was dried over magnesium sulfate, filtered and concentrated. The residue was slurried with diethyl ether, filtered and concentrated to afford 80-3.

Step 4. A solution of 80-3 (2.0 g, 7.5 mmol) in ethanol was treated with an aqueous potassium hydroxide solution (3 N, 5 mL). The mixture was heated to 95° C. for 2 days, and then cooled to 25° C. and neutralized to pH=2 with hydrochloric acid (3 N). This mixture was diluted with water and extracted with ethyl acetate. The combined organic layer was dried over magnesium sulfate, filtered, and concentrated to give a residue which was purified by flash chromatography to afford 80-4.

Step 5. A mixture of 80-4 (500 mg, 2.6 mmol), 27-1 (2.3 g, 10 mmol), cesium carbonate (5.2 g, 16.0 mmol) in dimethylacetamide (2 mL) was heated at 90° C. overnight. After cooled to room temperature, the reaction mixture was diluted with ethyl acetate, washed with water and brine, dried over sodium sulfate, filtered and concentrated. The residue was purified by column chromatography on silica gel (petroleum ether to petroleum ether/ethyl acetate=100 to 50%) to give 80-5.

Followed the similar steps in example 1 to synthesize 80. LCMS (ESI, m/z): 499.3 [M+H]$^+$. HNMR (400 MHz, DMSO-$d_6$, ppm): δ 13.27 (bs, 1H), 12.93 (s, 1H), 7.76 (s, 2H), 7.27-7.19 (m, 5H), 7.09 (s, 1H), 3.74 (s, 2H).

Example 28. Synthesis of Compound 85

Step 1. A solution of 2,6-dichloro-4-nitro-phenol (10.0 g, 48 mmol) in N,N-dimethylformamide (200 mL) at 25° C. was treated with 1,4-diazabicyclo [2.2.2]octane (10.0 g, 96 mmol) and dimethylthiocarbamoyl chloride (9.5 g, 76 mmol). The reaction was stirred at 25° C. for 18 hours. Then the mixture was diluted with ethyl acetate, washed with aqueous hydrochloric acid, water and brine, dried over magnesium sulfate, filtered and concentrated. The residue was purified with chromatography on silica gel to afford 80-1.

Step 2. Neat 80-1 (6.6 g, 23 mmol) was heated to 180-200° C. for 20 min. and then cooled to afford 80-2.

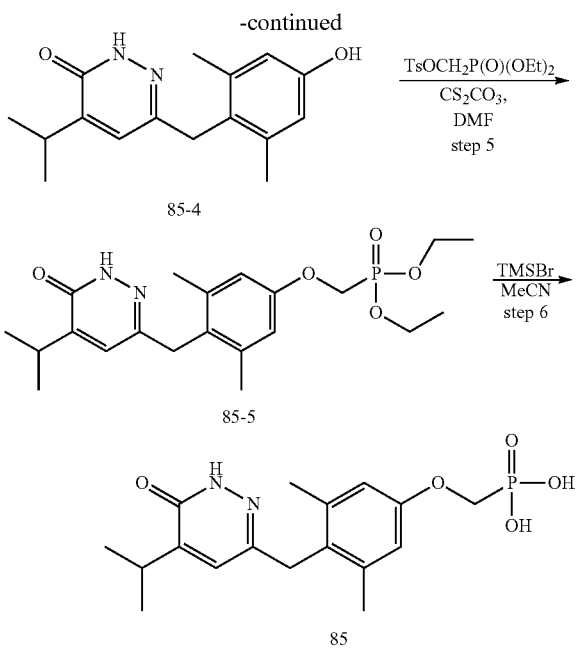

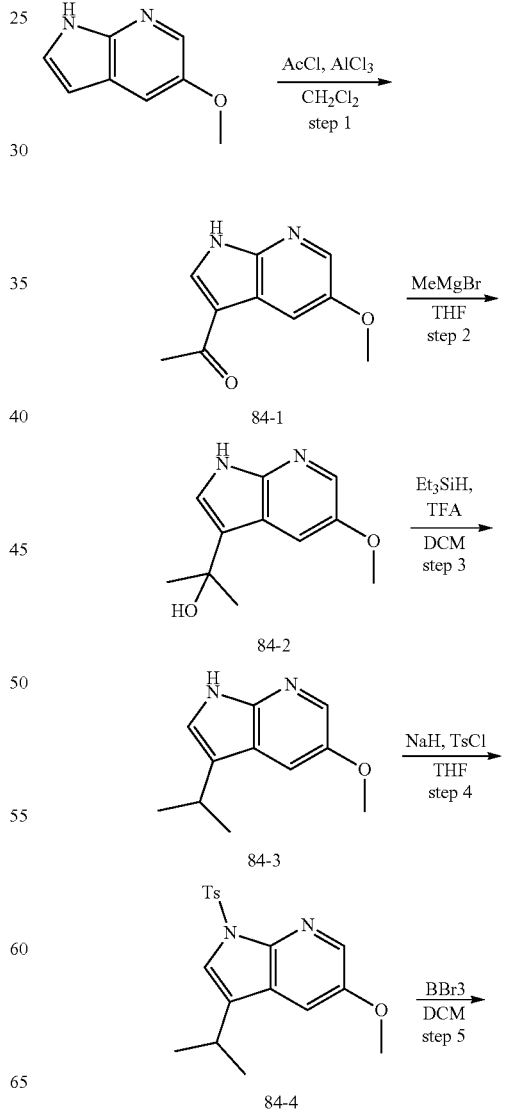

added cesium carbonate (362 mg, 1.11 mmol), and the reaction mixture was stirred at room temperature overnight. Water and ethyl acetate were added, and the organic layer was separated, washed with brine, dried over sodium sulfate, filtered and concentrated. The residue was purified by column chromatography on silica gel (petroleum ether to petroleum ether/ethyl acetate=3:1) to afford 85-5.

Step 6. To a solution of 85-5 (20 mg, 0.05 mmol) in acetonitrile (5 mL) was added dropwise bromotrimethylsilane (0.5 mL), and the reaction mixture was stirred at room temperature for 3 hours. The reaction solution was concentrated and the residue was purified by a prep-HPLC (acetonitrile with 0.05%TFA in water: 25% to 50%) to afford 85. LCMS (ESI, m/z): 367.3 [M+H]$^+$. HNMR (400 MHz, DMSO-d$_6$, ppm): δ 12.53 (s, 1H), 6.97 (s, 1H), 6.61 (s, 2H), 3.94 (d, J=10.0 Hz, 2H), 3.80 (s, 2H), 2.91 (t, J=6.8 Hz, 1H), 2.14 (s, 6H), 1.05 (d, J=6.8 Hz, 6H).

Example 29. Synthesis of Compound 84

Step 1. To a solution of (4-methoxy-2,6-dimethylphenyl) methanol (1.0 g, 6.0 mmol) in ether (15 mL) was added dropwise a solution of phosphorus tribromide (1.9 g, 7.2 mmol) in ether (2 mL) at 0° C. The mixture was stirred at 0° C. to room temperature for 40 min, followed by quenching with a saturated aqueous sodium bicarbonate solution. The mixture was extracted with ethyl acetate, and the organic layer was washed with brine, dried over sodium sulfate, filtered and concentrated to afford 85-1.

Step 2. To a solution of 85-1 (600 mg, 2.6 mmol) in acetonitrile (15 mL) was added trimethylsilyl cyanide (437 mg, 4.9 mmol) and tetrabutylammonium fluoride (1 M in THF, 4.4 mL, 4.4 mmol) at 0° C. The mixture was stirred at room temperature for 2 hours, followed by quenching with a saturated aqueous sodium bicarbonate solution. The mixture was extracted with ethyl acetate and the organic layer was washed with brine, dried over sodium sulfate, filtered and concentrated. The residue was purified by column chromatography on silica gel (petroleum ether to petroleum ether/ethyl acetate=10:1) to afford 85-2.

Step 3. To a solution of 85-2 (350 mg, 2.0 mmol) and 3,6-dichloro-4-(propan-2-yl)pyridazine (380 mg, 2.0 mmol) in tetrahydrofuran (15 mL) was added potassium tert-butoxide (290 mg, 2.6 mmol) at room temperature. The mixture was stirred at 60° C. for 3 hours, followed by quenching with water. The mixture was extracted with ethyl acetate and the organic layer was washed with brine, dried over sodium sulfate, filtered and concentrated. The residue was purified by column chromatography on silica gel (petroleum ether to petroleum ether/ethyl acetate=8:1) to afford 85-3.

Step 4. To a solution of 85-3 (300 mg, 0.91 mmol) in acetic acid (3 mL) was added concentrated HCl (15 mL). The mixture was then heated to 120° C. for overnight. After cooled to room temperature, the mixture was diluted with ethyl acetate and washed with brine, dried over sodium sulfate, filtered and concentrated. The residue was purified by column chromatography on silica gel (petroleum ether to petroleum ether/ethyl acetate=8:1) to afford 85-4.

Step 5. To a solution of 85-4 (100 mg, 0.37 mmol) and (diethoxyphosphoryl)methyl 4-methylbenzenesulfonate (95 mg, 0.29 mmol) in N,N-dimethylformamide (10 mL) was

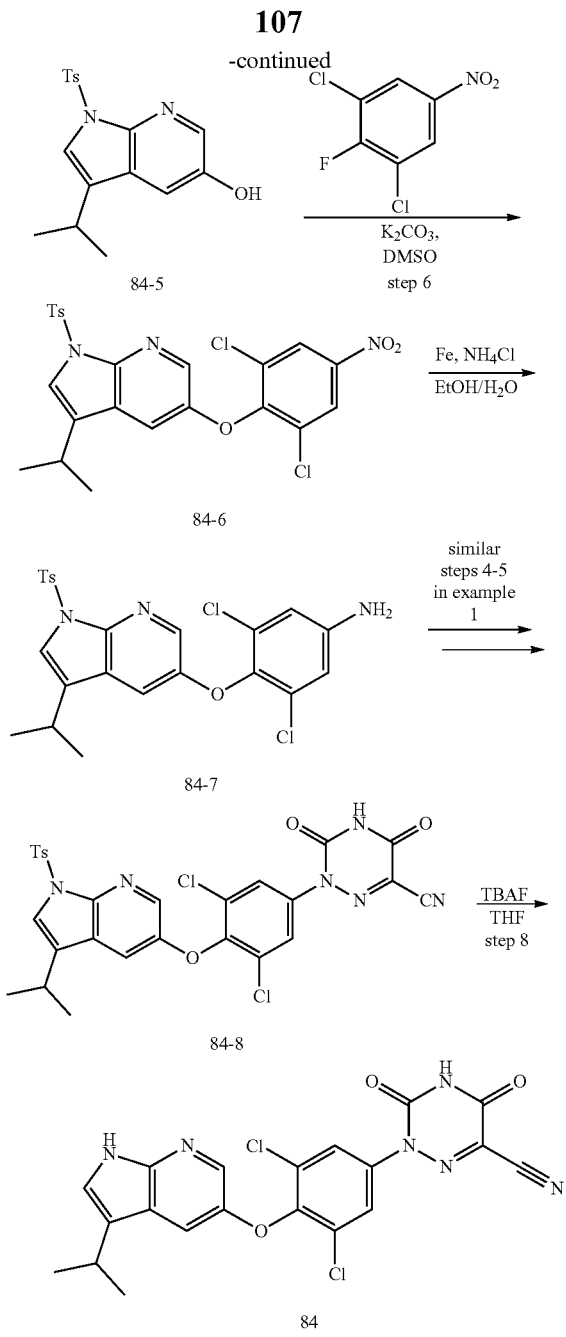

with a saturated aqueous NH$_4$Cl solution. The mixture was extracted with EtOAc, and the combined organic layer was washed with brine, dried over anhydrous Na$_2$SO$_4$, filtered and concentrated. The residue was purified by column chromatography on silica gel (petroleum ether/ethyl acetate=1:1) to afford 84-2.

Step 3. To a solution of 84-2 (1.0 g, 4.85 mmol) in dry dichloromethane (20 mL) was added dropwise triethylsilane (1.69 g, 14.53 mmol) and trifluoroacetic acid (2.76 g, 24.21 mmol) at 0° C. The mixture was stirred at room temperature overnight, followed by pouring into ice water. The mixture was neutralized to pH 4 to 5 with saturated sodium bicarbonate solution and extracted with dichloromethane. The combined organic layer was washed with brine, dried over sodium sulfate, filtered and concentrated. The residue was purified by column chromatography on silica gel (3% to 10% ethyl acetate in petroleum ether) to afford 84-3.

Step 4. To a solution of 84-3 (1.25 g, 6.57 mmol) in THF (25 mL) was added NaH (60%, 315 mg, 7.89 mmol) at 0° C., and the mixture was stirred for 0.5 hour, followed by addition of TsCl (1.5 g, 7.89 mmol). The resulting mixture was stirred at room temperature for 3 hours. Ice-water was added and the mixture was extracted with EtOAc. The combined organic layer was washed with brine, dried over anhydrous Na$_2$SO$_4$, filtered and concentrated. The residue was purified by column chromatography on silica gel (petroleum ether/ethyl acetate=10:1) to afford 84-4.

Step 5. To a solution of 84-4 (980 mg, 2.85 mmol) in DCM (20 mL) was added BBr$_3$ (1.0M in DCM, 5.38 mL) drop wise at 0° C. The mixture was stirred at 0° C. for 1.5 hour, followed by quenching with a saturated aqueous NaHCO$_3$ solution. The mixture was extracted with EtOAc and the combined organic layer was washed with brine, dried over Na$_2$SO$_4$, filtered and concentrated to afford 84-5.

Step 6. To a solution of 84-5 (1.12 g, 3.39 mmol) and 1,3-dichloro-2-fluoro-5-nitrobenzene (0.71 g, 3.38 mmol) in DMSO (10 mL) was added K$_2$CO$_3$ (1.41 g, 10.20 mmol) in portions. The mixture was stirred for 2 hours and then diluted with water. The mixture was extracted with EtOAc and the combined organic layer was dried over Na$_2$SO$_4$, filtered and concentrated. The residue was purified by column chromatography on silica gel (petroleum ether/ethyl acetate=5:1) to afford 84-6.

Step 7. A mixture of 84-6 (1.20 g, 2.31 mmol), iron powder (644 mg, 11.53 mmol) and NH$_4$Cl (987 mg, 18.45 mmol) in EtOH/H$_2$O (2:1, 30 mL) was heated at 70° C. for 3 hours. Then the mixture was filtered, and the filter cake was washed with EtOAc. The filtrate was extracted with EtOAc, and the combined organic layer was washed with brine, dried over anhydrous Na$_2$SO$_4$, filtered and concentrated. The residue was purified by a prep-TLC (petroleum ether/ethyl acetate=1:1) to afford 84-7.

Followed the similar steps in example 1 to synthesize 84-8.

Step 8. A mixture of 84-8 (100 mg, 0.16 mmol) and TBAF (1M in THF, 0.8 mL, 0.80 mmol) in THF (6 mL) was heated at 65° C. overnight under nitrogen atmosphere. The mixture was diluted with water and extracted with EtOAc. The combined organic layer was dried over anhydrous Na$_2$SO$_4$, filtered and concentrated. The residue was purified by a prep-TLC (ethyl acetate) to afford crude product which was purified with a prep-HPLC to afford 84. LCMS (ESI, m/z): 457.2 [M+H]$^+$. HNMR (300 MHz, DMSO-d$_6$, ppm): δ 13.28 (bs, 1H), 11.40 (s, 1H), 7.95 (s, 1H), 7.86 (s, 2H), 7.40 (d, J=2.7 Hz, 1H), 7.27 (d, J=2.1 Hz, 1H), 3.11-3.02 (m, 1H), 1.23 (d, J=6.9 Hz, 6H).

Step 1. To a suspension of AlCl$_3$ (45.0 g, 337.5 mmol) in DCM (150 mL) under N$_2$ was added 5-methoxy-1H-pyrrolo[2,3-b]pyridine (10.0 g, 67.5 mmol). The reaction mixture was stirred at ambient temperature for 1 hour where upon acetyl chloride (26.5 g, 337.5 mmol) was added dropwise and the resulting mixture was stirred for 5 hours. The reaction was cooled to 0° C., quenched with MeOH and concentrated. Water was added, and the mixture was extracted with EtOAc. The combined organic layer was dried over Na$_2$SO$_4$, filtered and concentrated. The residue was purified by column chromatography on silica gel (petroleum ether/ethyl acetate=1:1) to afford 84-1.

Step 2. To a solution of 84-1 (2.0 g, 10.52 mmol) in THF (5 mL) was added MeMgBr (21 mL, 42.0 mmol) at −10° C. The resulting mixture was stirred at room temperature for 3 hours under nitrogen atmosphere, followed by quenching

Example 30. Synthesis of Compound 86

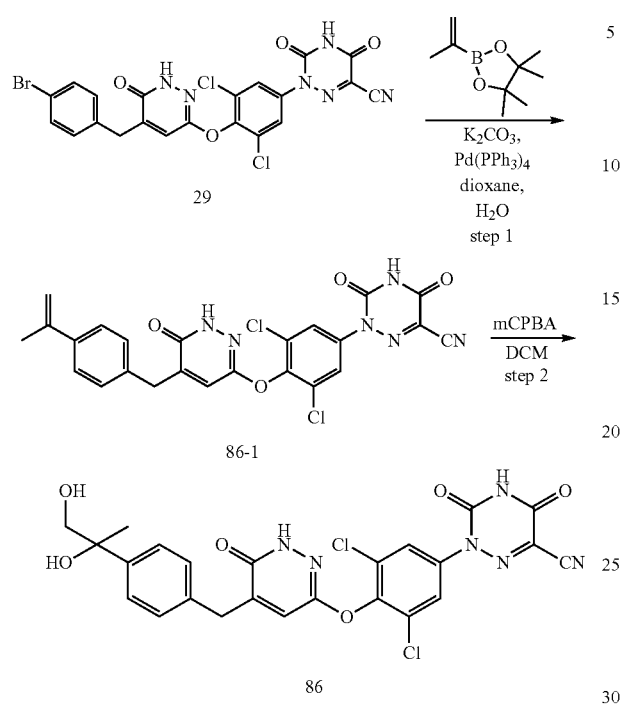

Step 1. A mixture of 29 (108 mg, 0.19 mmol), isopropenylboronic acid pinacol ester (39 mg, 0.23 mmol), potassium carbonate (53 g, 0.38 mmol) and tetrakis(triphenylphosphine) palladium (6 mg, 0.005 mmol) in 1,4-dioxane (1.5 mL) and water (0.5 mL) was heated at 90° C. for 4 hours under $N_2$ atmosphere. The reaction mixture was poured into water (10 mL) and extracted with ethyl acetate. The combined organic layer was washed with brine, dried over sodium sulfate, filtered and concentrated. The residue was purified by a prep-TLC (dichloromethane/methanol=8/1) to afford 86-1.

Step 2. A solution of 86-1 (70 mg, 0.13 mmol) and 3-chloroperbenzoic acid (28 mg, 0.16 mmol) in dichloromethane (2 mL) was stirred for 2 hours at room temperature. Then the mixture was quenched with an aqueous sodium thiosulfate solution, diluted with water and extracted with dichloromethane/tetrahydrofuran (2:1). The combined organic layer was washed with brine, dried over sodium sulfate, filtered and concentrated. The residue was slurried with dichloromethane (1 mL) to give a crude product which was purified with a prep-HPLC (acetonitrile with 0.05% TFA in water: 10% to 75%) to afford 86. LCMS (ESI, m/z): 557.4 [M+H]$^+$. HNMR (400 MHz, DMSO-$d_6$, ppm): δ 12.28 (s, 1H), 7.73 (s, 2H), 7.38 (d, J=8.4 Hz, 2H), 7.29 (s, 1H), 7.22 (d, J=8.4 Hz, 2H), 4.81 (s, 1H), 4.65-4.59 (m, 1H), 3.78 (s, 2H), 1.34 (s, 3H).

Example 31. Synthesis of Compound 90 and 91

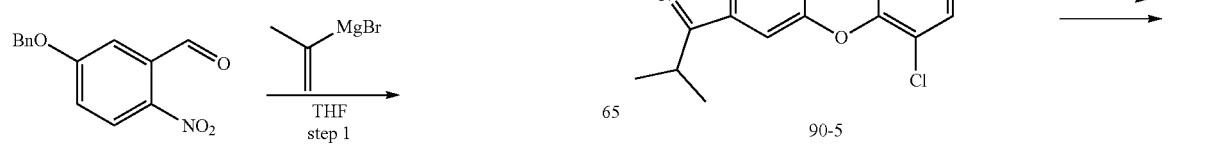

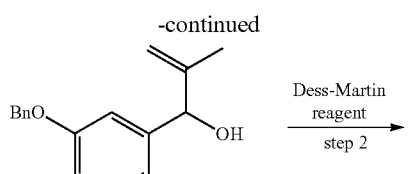

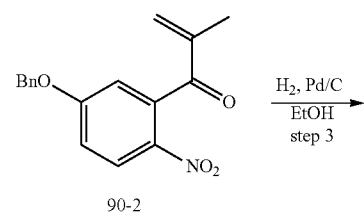

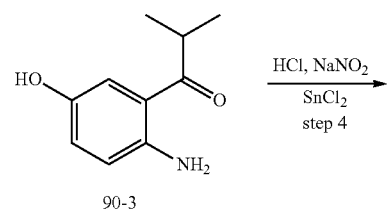

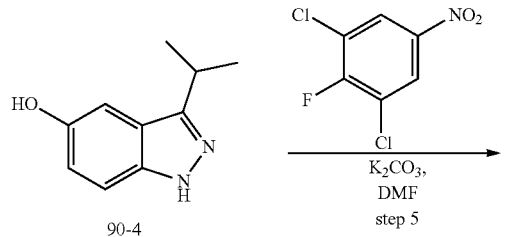

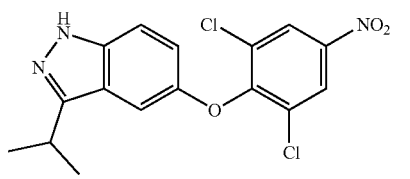

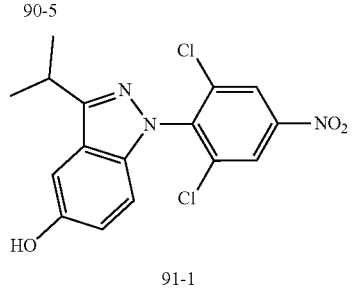

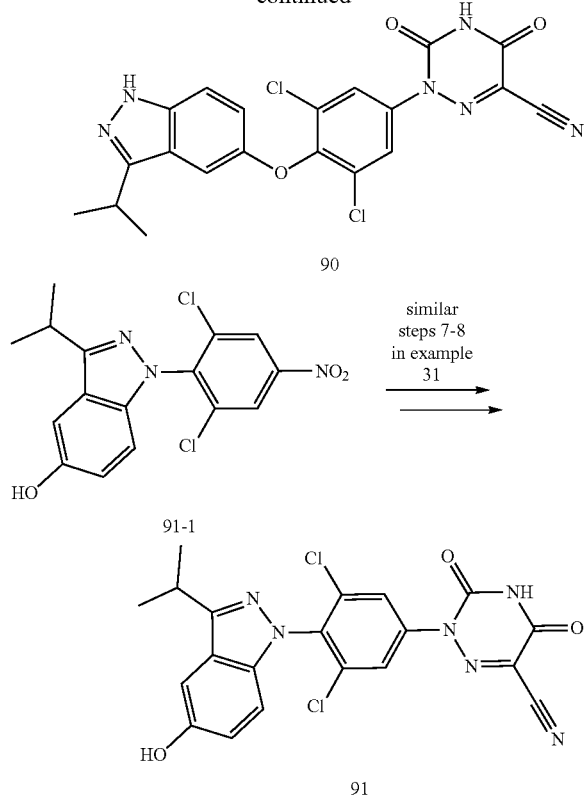

Step 1. To a solution of 5-(benzyloxy)-2-nitrobenzaldehyde (9.50 g, 36.93 mmol) in THF (20 mL) was added bromo(prop-1-en-2-yl)magnesium (7.51 g, 51.69 mmol) at −78° C. The mixture was stirred at −78° C. for 3 hours under nitrogen atmosphere, followed by quenching with an aqueous HCl solution to pH 5. The mixture was extracted with EtOAc, and the combined organic layer was dried over anhydrous Na$_2$SO$_4$, filtered and concentrated. The residue was purified by column chromatography on silica gel (petroleum ether/ethyl acetate=20:1) to afford 90-1.

Step 2. A mixture of 90-1 (7.40 g, 24.72 mmol) and Dess-Martin reagent (12.58 g, 29.66 mmol) in DCM (100 mL) and pyridine (5 mL) was stirred at room temperature for 2 hours. An aqueous Na$_2$CO$_3$ solution was added, and the mixture was filtered. The filtrate was extracted with dichloromethane, and the combined organic layer was dried over anhydrous sodium sulfate, filtered and concentrated. The residue was purified by column chromatography on silica gel (petroleum ether/ethyl acetate=100:1) to afford 90-2.

Step 3. To a solution of 90-2 (3.50 g, 11.77 mmol) in EtOH (20 ml) was added 10% Pd/C (2.51 g, 2.36 mmol), and the mixture was stirred under H$_2$ atmosphere for 4 hours. The mixture was filtered, and the filtrate was concentrated. The residue was purified by column chromatography on silica gel (petroleum ether/ethyl acetate=4:1) to afford 90-3.

Step 4. To a solution of 90-3 (1.70 g, 9.49 mmol) in HCl (conc., 10 mL) was added a solution of NaNO$_2$ (720 mg, 10.43 mmol) in H$_2$O (5 mL) at 0° C. After stirring for 1 hour, a solution of SnCl$_2$·2 H$_2$O (5.14 g, 22.77 mmol) in HCl (conc. 5 mL) was added, and the mixture was stirred at 0° C. for 2 hours. Then the mixture was diluted with water and neutralized to pH 7 with a saturated aqueous NaHCO$_3$ solution. The resulting mixture was extracted with EtOAc, and the combined organic layer was washed with brine, dried over anhydrous Na$_2$SO$_4$, filtered and concentrated. The residue was purified by column chromatography on silica gel (petroleum ether/ethyl acetate=5:1) to afford 90-4.

Step 5. A mixture of 90-4 (2.0 g, 11.35 mmol), 1,3-dichloro-2-fluoro-5-nitrobenzene (2.38 g, 11.33 mmol) and K$_2$CO$_3$ (1.88 g, 13.60 mmol) in DMF (10 mL) was stirred at room temperature for 3 hours. Then the mixture was diluted with water and extracted with EtOAc. The combined organic layer was washed with brine, dried over anhydrous Na$_2$SO$_4$, filtered and concentrated. The residue was purified by column chromatography on silica gel (petroleum ether/ethyl acetate=5:1) to afford 90-5 and 91-1, respectively.

Followed the similar steps in example 33 to synthesize 90. LCMS (ESI, m/z): 457.1 [M+H]$^+$. HNMR (300 MHz, DMSO-d$_6$, ppm): δ 12.62 (s, 1H), 7.84 (s, 2H), 7.47 (d, J=9.3 Hz, 1H), 7.05-6.99 (m, 2H), 3.33-3.23 (m, 1H), 1.29 (d, J=6.9 Hz, 6H).

Followed the similar steps in example 33 to synthesize 91. LCMS (ESI, m/z): 457.1 [M+H]$^+$. HNMR (300 MHz, DMSO-d$_6$, ppm): δ 9.33 (s, 1H), 7.90 (s, 2H), 7.12 (d, J=1.5 Hz, 1H), 7.06-6.94 (m, 2H), 3.41-3.43 (m, 1H), 1.39 (d, J=7.2 Hz, 6H).

Further exemplary thyroid hormone receptor β agonist compounds as described herein can be prepared following similar methods and techniques herein. Characterization of the compounds are provided in Table 1 below:

TABLE 1

Characterization of Selected Compounds

| Compound No. | Structure | [M+H]$^+$ | $^1$HNMR and $^{19}$FNMR |
|---|---|---|---|
| 2 | 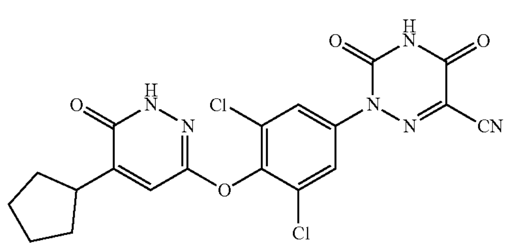 [SMILES: N#Cc1nn(-c2cc(Cl)c(Oc3cc(C4CCCC4)c(=O)[nH]n3)c(Cl)c2)c(=O)[nH]c1=O] | 461.3 | HNMR (400 MHz, DMSO-d$_6$, ppm): δ 12.17 (s, 1H), 7.74 (s, 2H), 7.43 (s, 1H), 3.10-3.02 (m, 1H), 1.94-1.90 (m, 2H), 1.72-1.66 (m, 2H), 1.64-1.52 (m, 4H). |

TABLE 1-continued

Characterization of Selected Compounds

| Compound No. | Structure | [M + H]⁺ | ¹HNMR and ¹⁹FNMR |
|---|---|---|---|
| 3 | 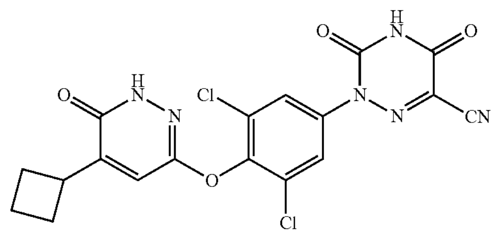 [SMILES: N#Cc1nn(-c2cc(Cl)c(Oc3cc(C4CCC4)c(=O)[nH]n3)c(Cl)c2)c(=O)[nH]c1=O] | 447.3 | HNMR (400 MHz, DMSO-d$_6$, ppm): δ 13.24 (br s, 1H), 12.16 (s, 1H), 7.75 (s, 2H), 7.45 (d, J = 1.2 Hz, 1H), 3.56-3.47 (m, 1H), 2.27-2.19 (m, 2H), 2.15-2.05 (m, 2H), 2.03-1.92 (m, 1H), 1.82-1.74 (m, 1H). |
| 4 | 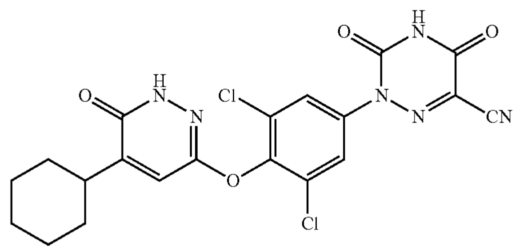 [SMILES: N#Cc1nn(-c2cc(Cl)c(Oc3cc(C4CCCCC4)c(=O)[nH]n3)c(Cl)c2)c(=O)[nH]c1=O] | 475.3 | HNMR (400 MHz, DMSO-d$_6$, ppm): δ 13.25 (br s, 1H), 12.20 (s, 1H), 7.75 (s, 2H), 7.36 (s, 1H), 2.77-2.67 (m, 1H), 1.80-1.67 (m, 5H), 1.37-1.20 (m, 5H). |
| 5 | 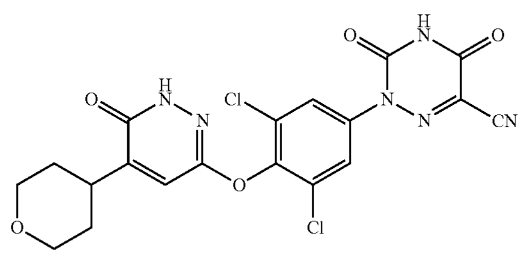 [SMILES: N#Cc1nn(-c2cc(Cl)c(Oc3cc(C4CCOCC4)c(=O)[nH]n3)c(Cl)c2)c(=O)[nH]c1=O] | 477.1 | HNMR (300 MHz, DMSO-d$_6$, ppm): δ 13.25 (br s, 1H), 12.29 (s, 1H), 7.79 (s, 2H), 7.47 (s, 1H), 4.12-3.88 (m, 2H), 3.57-3.38 (m, 2H), 3.12-2.86 (m, 1H), 1.89-1.52 (m, 4H). |
| 6 | 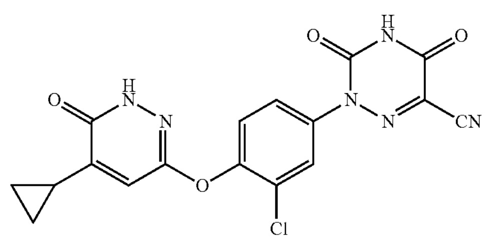 [SMILES: N#Cc1nn(-c2ccc(Oc3cc(C4CC4)c(=O)[nH]n3)c(Cl)c2)c(=O)[nH]c1=O] | 399.1 | HNMR (300 MHz, DMSO-d$_6$, ppm): δ 13.16 (br s, 1H), 12.21 (s, 1H), 7.73 (s, 1H), 7.52 (s, 2H), 7.08 (s, 1H), 2.18-2.08 (m, 1H), 1.08-1.02 (m, 4H). |
| 7 | 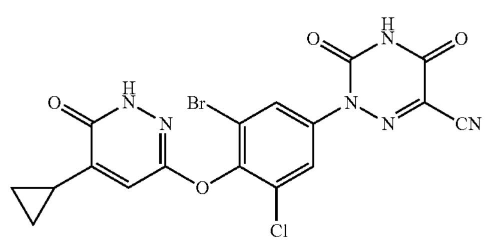 [SMILES: N#Cc1nn(-c2cc(Cl)c(Oc3cc(C4CC4)c(=O)[nH]n3)c(Br)c2)c(=O)[nH]c1=O] | 477.0 | HNMR (300 MHz, DMSO-d$_6$, ppm): δ 13.27 (br s, 1H), 12.19 (s, 1H), 7.88 (d, J = 5.4 Hz, 1H), 7.80 (d, J = 5.4 Hz, 1H), 7.18 (s, 1H), 2.18-2.11 (m, 1H), 1.12-1.07 (m, 4H). |
| 8 | 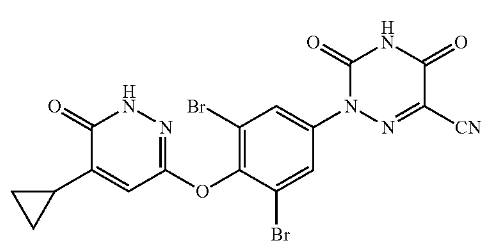 [SMILES: N#Cc1nn(-c2cc(Br)c(Oc3cc(C4CC4)c(=O)[nH]n3)c(Br)c2)c(=O)[nH]c1=O] | 520.9 | HNMR (300 MHz, DMSO-d$_6$, ppm): δ 13.27 (br s, 1H), 12.20 (s, 1H), 7.90 (s, 2H), 7.19 (s, 1H), 2.14-2.18 (m, 1H), 1.05-1.10 (m, 4H). |

TABLE 1-continued

Characterization of Selected Compounds

| Compound No. | Structure | [M + H]+ | 1HNMR and 19FNMR |
|---|---|---|---|
| 9 | 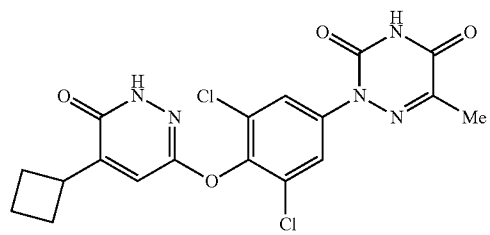 [SMILES: Cc1nn(-c2cc(Cl)c(Oc3cc(C4CCC4)c(=O)[nH]n3)c(Cl)c2)c(=O)[nH]c1=O] | 436.3 | HNMR (400 MHz, DMSO-d6, ppm): δ 12.38 (br s, 1H), 12.14 (s, 1H), 7.75 (s, 2H), 7.43 (s, 1H), 3.55-3.47 (m, 1H), 2.28-2.19 (m, 2H), 2.12 (s, 3H), 2.11-1.91 (m, 3H), 1.82-1.73 (m, 1H). |
| 10 | 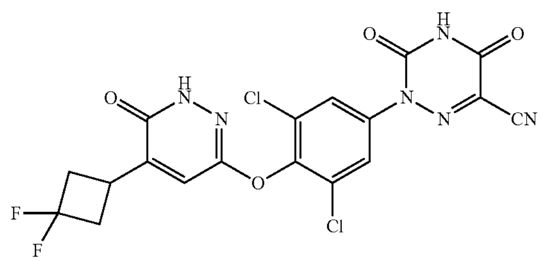 [SMILES: N#Cc1nn(-c2cc(Cl)c(Oc3cc(C4CC(F)(F)C4)c(=O)[nH]n3)c(Cl)c2)c(=O)[nH]c1=O] | 483.3 | HNMR (400 MHz, DMSO-d6, ppm): δ 12.29 (s, 1H), 7.74 (s, 2H), 7.63 (d, J = 1.2 Hz, 1H), 3.39-3.30 (m, 1H), 2.90-2.82 (m, 4H). |
| 11 | 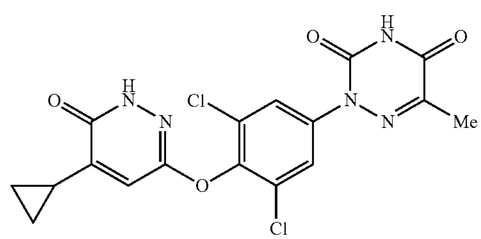 [SMILES: Cc1nn(-c2cc(Cl)c(Oc3cc(C4CC4)c(=O)[nH]n3)c(Cl)c2)c(=O)[nH]c1=O] | 422.1 | HNMR (300 MHz, DMSO-d6, ppm): δ 12.19 (s, 1H), 7.78 (s, 2H), 7.17 (s, 1H), 2.20-2.10 (m, 1H), 2.15 (s, 3H), 1.10-1.00 (m, 4H). |
| 12 | 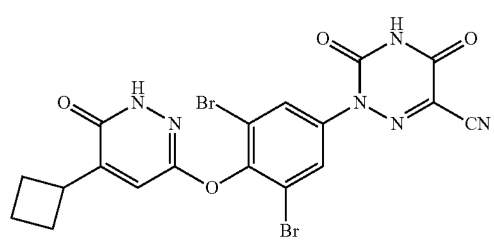 [SMILES: N#Cc1nn(-c2cc(Br)c(Oc3cc(C4CCC4)c(=O)[nH]n3)c(Br)c2)c(=O)[nH]c1=O] | 535.2 | HNMR (400 MHz, DMSO-d6, ppm): δ 13.23 (br s, 1H), 12.14 (s, 1H), 7.87 (s, 2H), 7.44 (d, J = 1.2 Hz, 1H), 3.56-3.47 (m, 1H), 2.26-2.19 (m, 2H), 2.15-2.05 (m, 2H), 2.03-1.93 (m, 1H), 1.81-1.77 (m, 1H). |
| 13 | 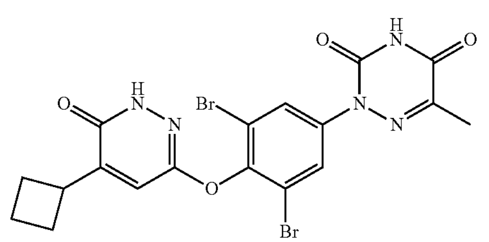 [SMILES: Cc1nn(-c2cc(Br)c(Oc3cc(C4CCC4)c(=O)[nH]n3)c(Br)c2)c(=O)[nH]c1=O] | 524.2 | HNMR (400 MHz, DMSO-d6, ppm): δ 12.10 (s, 1H), 7.89 (s, 2H), 7.41 (d, J = 0.8 Hz, 1H), 3.55-3.47 (m, 1H), 2.29-2.19 (m, 2H), 2.14-2.02 (m, 5H), 2.01-1.91 (m, 1H), 1.81-1.74 (m, 1H). |
| 14 | 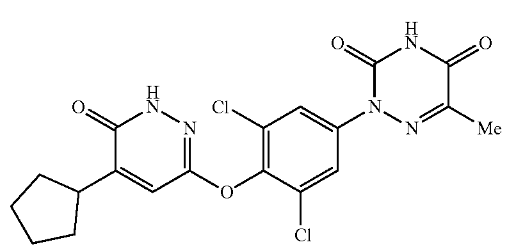 [SMILES: Cc1nn(-c2cc(Cl)c(Oc3cc(C4CCCC4)c(=O)[nH]n3)c(Cl)c2)c(=O)[nH]c1=O] | 450.3 | HNMR (400 MHz, DMSO-d6, ppm): δ 12.37 (s, 1H), 12.16 (s, 1H), 7.75 (s, 2H), 7.41 (s, 1H), 3.11-3.02 (m, 1H), 2.12 (s, 3H), 1.94-1.90 (m, 2H), 1.72-1.70 (m, 2H), 1.64-1.52 (m, 4H). |

TABLE 1-continued

Characterization of Selected Compounds

| Compound No. | Structure | [M + H]⁺ | ¹HNMR and ¹⁹FNMR |
|---|---|---|---|
| 15 | 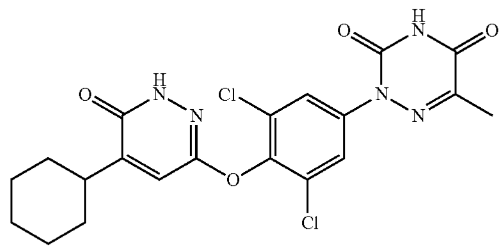 [SMILES: Cc1nn(-c2cc(Cl)c(Oc3cc(C4CCCCC4)c(=O)[nH]n3)c(Cl)c2)c(=O)[nH]c1=O] | 464.3 | HNMR (400 MHz, DMSO-d$_6$, ppm): δ 12.38 (s, 1H), 12.18 (s, 1H), 7.76 (s, 2H), 7.35 (s, 1H), 2.75-2.66 (m, 1H), 2.13 (s, 3H), 1.80-1.66 (m, 5H), 1.34-1.19 (m, 5H). |
| 17 | 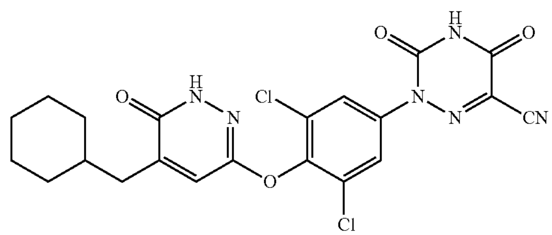 [SMILES: N#Cc1nn(-c2cc(Cl)c(Oc3cc(CC4CCCCC4)c(=O)[nH]n3)c(Cl)c2)c(=O)[nH]c1=O] | 489.3 | HNMR (400 MHz, DMSO-d$_6$, ppm): δ 13.24 (br s, 1H), 12.19 (s, 1H), 7.74 (s, 2H), 7.45 (s, 1H), 2.38 (d, J = 6.8 Hz, 2H), 1.65-1.58 (m, 6H), 1.20-1.13 (m, 3H), 0.95-0.92 (m, 2H). |
| 18 | 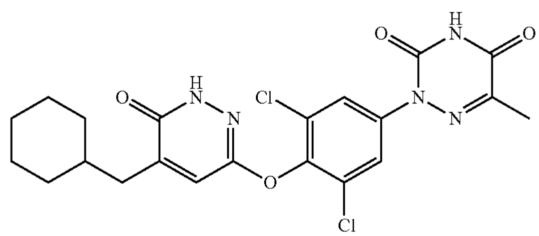 [SMILES: Cc1nn(-c2cc(Cl)c(Oc3cc(CC4CCCCC4)c(=O)[nH]n3)c(Cl)c2)c(=O)[nH]c1=O] | 478.3 | HNMR (400 MHz, DMSO-d$_6$, ppm): δ 12.37 (br s, 1H), 12.17 (s, 1H), 7.75 (s, 2H), 7.42 (s, 1H), 2.37 (d, J = 6.8 Hz, 2H), 2.12 (s, 3H), 1.65-1.57 (m, 6H), 1.18-1.11 (m, 3H), 0.97-0.91 (m, 2H). |
| 20 | 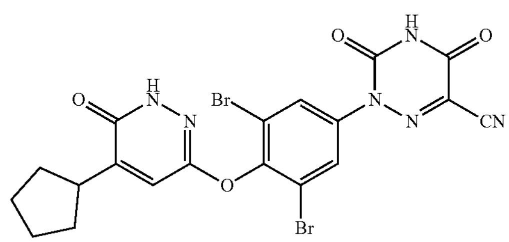 | 549.2 | HNMR (400 MHz, DMSO-d$_6$, ppm): δ 13.23 (br s, 1H), 12.16 (s, 1H), 7.87 (s, 2H), 7.42 (d, J = 0.8 Hz, 1H), 3.11-3.03 (m, 1H), 1.94-1.90 (m, 2H), 1.72-1.67 (m, 2H), 1.64-1.51 (m, 4H). |
| 22 | 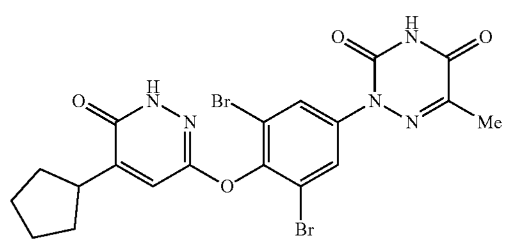 [SMILES: Cc1nn(-c2cc(Br)c(Oc3cc(C4CCCC4)c(=O)[nH]n3)c(Br)c2)c(=O)[nH]c1=O] | 538.3 | HNMR (400 MHz, DMSO-d$_6$, ppm): δ 12.36 (br s, 1H), 12.14 (s, 1H), 7.88 (s, 2H), 7.40 (s, 1H), 3.11-3.02 (m, 1H), 2.12 (s, 3H), 1.94-1.90 (m, 2H), 1.72-1.69 (m, 2H), 1.64-1.52 (m, 4H). |
| 23 | 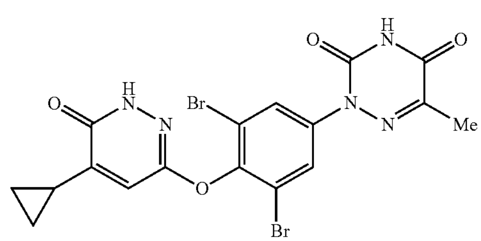 [SMILES: Cc1nn(-c2cc(Br)c(Oc3cc(C4CC4)c(=O)[nH]n3)c(Br)c2)c(=O)[nH]c1=O] | 510.2 | HNMR (400 MHz, DMSO-d$_6$, ppm): δ 12.35 (br s, 1H), 12.14 (s, 1H), 7.87 (s, 2H), 7.13 (s, 1H), 2.14-2.07 (m, 4H), 1.05-1.02 (m, 2H), 0.98-0.96 (m, 2H). |

TABLE 1-continued

Characterization of Selected Compounds

| Compound No. | Structure | [M + H]⁺ | ¹HNMR and ¹⁹FNMR |
|---|---|---|---|
| 24 | 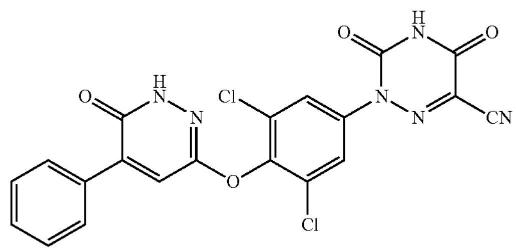 [SMILES: N#Cc1nn(-c2cc(Cl)c(Oc3cc(-c4ccccc4)c(=O)[nH]n3)c(Cl)c2)c(=O)[nH]c1=O] | 469.2 | HNMR (300 MHz, DMSO-d₆, ppm): δ 12.48 (s, 1H), 7.96-7.98 (m, 2H), 7.88 (s, 1H), 7.80 (s, 2H), 7.49-7.51 (m, 3H). |
| 26 | 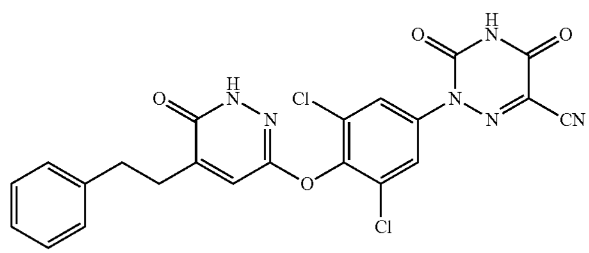 [SMILES: N#Cc1nn(-c2cc(Cl)c(Oc3cc(CCc4ccccc4)c(=O)[nH]n3)c(Cl)c2)c(=O)[nH]c1=O] | 497.3 | HNMR (400 MHz, DMSO-d₆, ppm): δ 12.21 (s, 1H), 7.73 (s, 2H), 7.36 (s, 1H), 7.28-7.24 (m, 2H), 7.21-7.14 (m, 3H), 2.90-2.87 (m, 2H), 2.80-2.75 (m, 2H). |
| 29 | 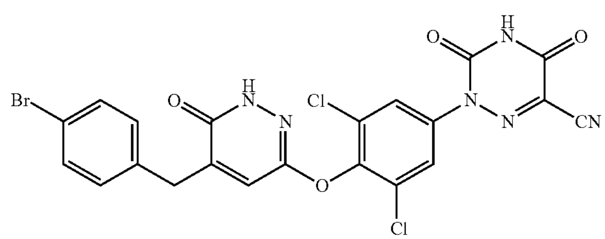 [SMILES: N#Cc1nn(-c2cc(Cl)c(Oc3cc(Cc4ccc(Br)cc4)c(=O)[nH]n3)c(Cl)c2)c(=O)[nH]c1=O] | 561.3 | HNMR (400 MHz, DMSO-d₆, ppm): δ 13.25 (br s, 1H), 12.32 (s, 1H), 7.74 (s, 2H), 7.51 (d, J = 8.0 Hz, 2H), 7.39 (s, 1H), 7.29 (d, J = 8.0 Hz, 2H), 3.81 (s, 2H). |
| 30 | 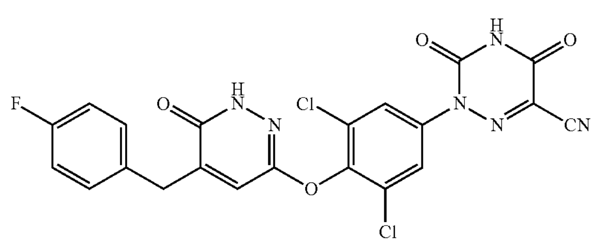 [SMILES: N#Cc1nn(-c2cc(Cl)c(Oc3cc(Cc4ccc(F)cc4)c(=O)[nH]n3)c(Cl)c2)c(=O)[nH]c1=O] | 501.3 | HNMR (400 MHz, DMSO-d₆, ppm): δ 12.21 (s, 1H), 7.72 (s, 2H), 7.39-7.36 (m, 3H), 7.16-7.12 (m, 2H), 3.98 (s, 2H). |
| 31 | 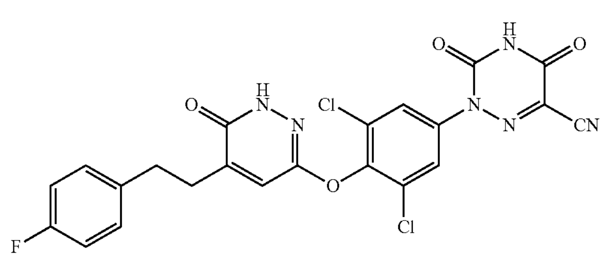 [SMILES: N#Cc1nn(-c2cc(Cl)c(Oc3cc(CCc4ccc(F)cc4)c(=O)[nH]n3)c(Cl)c2)c(=O)[nH]c1=O] | 515.3 | HNMR (400 MHz, DMSO-d₆, ppm): δ 12.21 (s, 1H), 7.73 (s, 2H), 7.37 (s, 1H), 7.25-7.21 (m, 2H), 7.10-7.06 (m, 2H), 2.90-2.86 (m, 2H), 2.78-2.74 (m, 2H). |
| 32 | 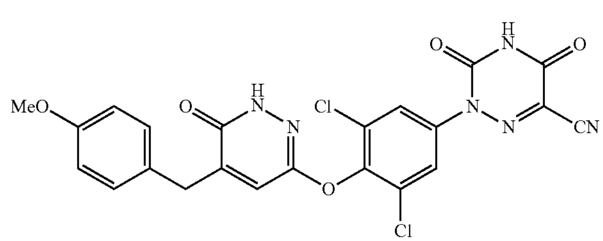 [SMILES: COc1ccc(Cc2cc(Oc3c(Cl)cc(-n4nc(C#N)c(=O)[nH]c4=O)cc3Cl)n[nH]c2=O)cc1] | 513.3 | HNMR (400 MHz, DMSO-d₆, ppm): δ 12.27 (s, 1H), 7.90-7.70 (m, 2H), 7.38-7.13 (m, 3H), 6.97-6.81 (m, 2H), 3.75 (s, 2H), 3.70 (s, 3H). |

TABLE 1-continued

Characterization of Selected Compounds

| Compound No. | Structure | [M + H]+ | ¹HNMR and ¹⁹FNMR |
|---|---|---|---|
| 38 | 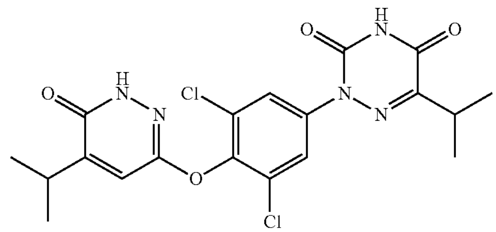 [SMILES: CC(C)c1cc(Oc2c(Cl)cc(-n3nc(C(C)C)c(=O)[nH]c3=O)cc2Cl)n[nH]c1=O] | 452.3 | HNMR (400 MHz, DMSO-d₆, ppm): δ 12.38 (s, 1H), 12.18 (s, 1H), 7.78 (s, 2H), 7.41 (s, 1H), 3.10-2.98 (m, 2H), 1.17 (d, J = 6.8 Hz, 6H), 1.13 (d, J = 6.8 Hz, 6H). |
| 46 | 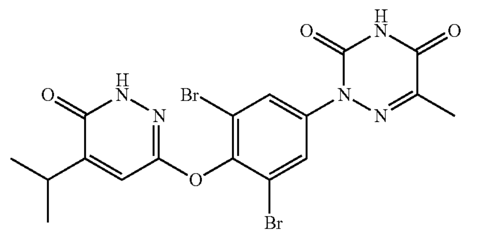 [SMILES: Cc1nn(-c2cc(Br)c(Oc3cc(C(C)C)c(=O)[nH]n3)c(Br)c2)c(=O)[nH]c1=O] | 512.3 | HNMR (400 MHz, DMSO-d₆, ppm): δ 12.36 (s, 1H), 12.18 (s, 1H), 7.89 (s, 2H), 7.38 (s, 1H), 3.07-2.96 (m, 1H), 2.12 (s, 3H), 1.16 (d, J = 6.8 Hz, 6H). |
| 48 | 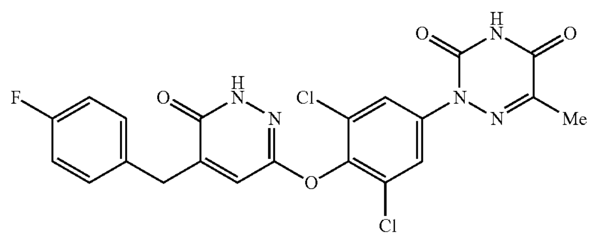 [SMILES: Cc1nn(-c2cc(Cl)c(Oc3cc(Cc4ccc(F)cc4)c(=O)[nH]n3)c(Cl)c2)c(=O)[nH]c1=O] | 490.3 | HNMR (400 MHz, DMSO-d₆, ppm): δ 12.37 (br s, 1H), 12.29 (s, 1H), 7.75 (s, 2H), 7.38-7.35 (m, 2H), 7.32 (s, 1H), 7.14 (t, J = 8.8 Hz, 2H), 3.82 (s, 2H), 2.12 (s, 3H). |
| 49 | 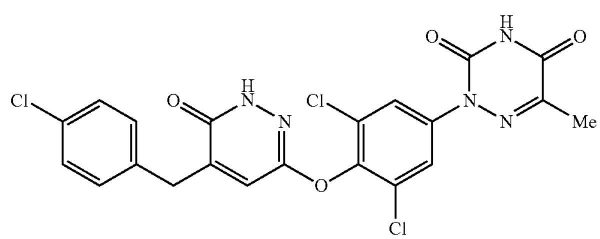 [SMILES: Cc1nn(-c2cc(Cl)c(Oc3cc(Cc4ccc(Cl)cc4)c(=O)[nH]n3)c(Cl)c2)c(=O)[nH]c1=O] | 506.3 | HNMR (400 MHz, DMSO-d₆, ppm): δ 12.37 (br s, 1H), 12.30 (s, 1H), 7.74 (s, 2H), 7.38-7.33 (m, 5H), 3.81 (s, 2H), 2.11 (s, 3H). |
| 50 | 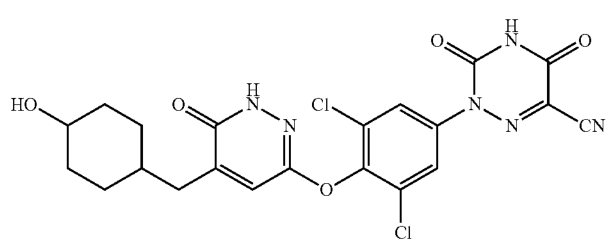 [SMILES: N#Cc1nn(-c2cc(Cl)c(Oc3cc(CC4CCC(O)CC4)c(=O)[nH]n3)c(Cl)c2)c(=O)[nH]c1=O] | 505.4 | HNMR (400 MHz, DMSO-d₆, ppm): δ 12.19 (s, 1H), 7.75 (s, 2H), 7.45 (s, 1H), 4.58-4.23 (m, 1H), 2.41-2.35 (m, 2H), 1.82-1.73 (m, 2H), 1.63-1.52 (m, 3H), 1.41-1.29 (m, 1H), 1.12-0.91 (m, 3H). |
| 51 | 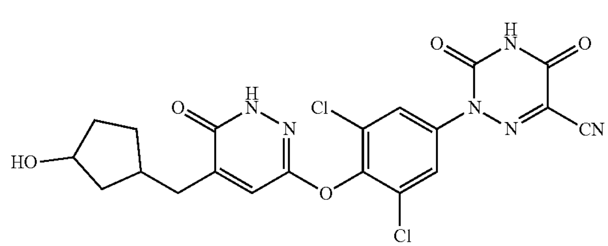 [SMILES: N#Cc1nn(-c2cc(Cl)c(Oc3cc(CC4CCC(O)C4)c(=O)[nH]n3)c(Cl)c2)c(=O)[nH]c1=O] | 491.3 | HNMR (400 MHz, DMSO-d₆, ppm): δ 13.24 (br s, 1H), 12.20 (s, 0.4H), 12.19 (s, 0.6H), 7.75 (s, 2H), 7.47 (s, 0.4H), 7.46 (s, 0.6H), 4.58-4.27 (m, 1H), 4.16-4.09 (m, 0.4H), 4.08-4.01 (m, 0.6H), 2.56-2.53 (m, 1H), 2.46-2.38 (m, 1.4H), 2.21-2.13 (m, 0.6H), 1.94-1.73 (m, 1.4H), 1.67-1.57 (m, 1.6H), 1.51-1.25 (m, 2H), 1.19-1.09 (m, 1H). |

TABLE 1-continued

Characterization of Selected Compounds

| Compound No. | Structure | [M + H]+ | 1HNMR and 19FNMR |
|---|---|---|---|
| 52 | 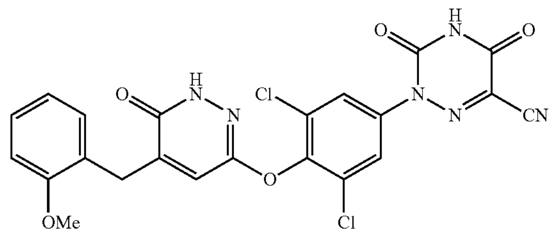 [SMILES: COc1ccccc1Cc1cc(Oc2c(Cl)cc(-n3nc(C#N)c(=O)[nH]c3=O)cc2Cl)n[nH]c1=O] | 513.3 | HNMR (400 MHz, DMSO-d6, ppm): δ 13.26 (br s, 1H), 12.31 (s, 1H), 7.73 (s, 2H), 7.28 (t, J = 7.2 Hz, 1H), 7.19 (d, J = 6.0 Hz, 1H), 7.03 (d, J = 8.0 Hz, 1H), 6.92 (t, J = 7.2 Hz, 1H), 6.86 (s, 1H), 3.76 (s, 5H). |
| 53 | 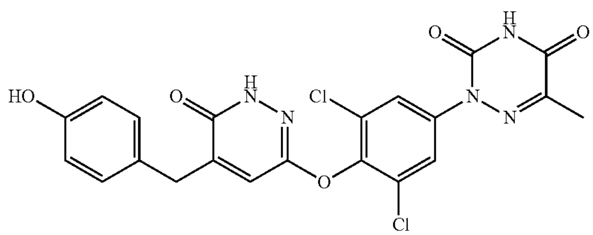 [SMILES: Cc1nn(-c2cc(Cl)c(Oc3cc(Cc4ccc(O)cc4)c(=O)[nH]n3)c(Cl)c2)c(=O)[nH]c1=O] | 488.3 | HNMR (400 MHz, DMSO-d6, ppm): δ 12.37 (br s, 1H), 12.24 (s, 1H), 9.30 (s, 1H), 7.74 (s, 2H), 7.19 (s, 1H), 7.10 (d, J = 8.8 Hz, 2H), 6.69 (d, J = 8.8 Hz, 2H), 3.69 (s, 2H), 2.12 (s, 3H). |
| 54 | 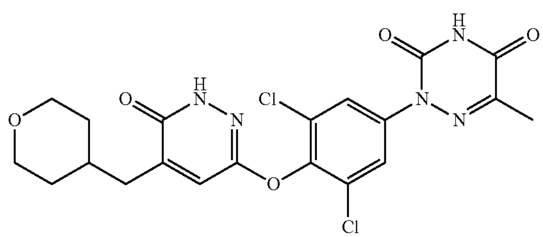 [SMILES: Cc1nn(-c2cc(Cl)c(Oc3cc(CC4CCOCC4)c(=O)[nH]n3)c(Cl)c2)c(=O)[nH]c1=O] | 480.4 | HNMR (400 MHz, DMSO-d6, ppm): δ 12.37 (br s, 1H), 12.20 (s, 1H), 7.76 (s, 2H), 7.49 (s, 1H), 3.82-3.78 (m, 2H), 3.24-3.18 (m, 2H), 2.44-2.42 (m, 2H), 2.12 (s, 3H), 1.93-1.88 (m, 1H), 1.49-1.46 (m, 2H), 1.26-1.20 (m, 2H). |
| 55 | 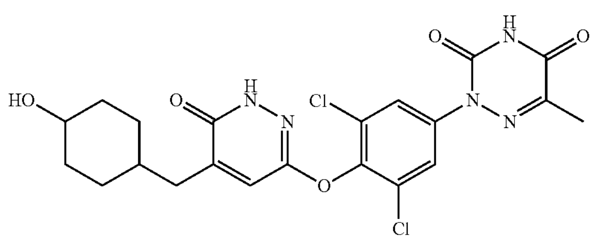 [SMILES: Cc1nn(-c2cc(Cl)c(Oc3cc(CC4CCC(O)CC4)c(=O)[nH]n3)c(Cl)c2)c(=O)[nH]c1=O] | 494.4 | HNMR (400 MHz, DMSO-d6, ppm): δ 12.37 (s, 1H), 12.16 (s, 1H), 7.75 (s, 2H), 7.45 (s, 0.2H), 7.43 (s, 0.8H), 4.45 (d, J = 4.4 Hz, 0.8H), 4.26 (d, J = 2.8 Hz, 0.2H), 3.75-3.63 (m, 0.2H), 3.28-3.21 (m, 0.8H), 2.41 (d, J = 6.8 Hz, 0.4H), 2.36 (d, J = 6.4 Hz, 1.6H), 2.12 (s, 3H), 1.78-1.75 (m, 2H), 1.58-1.56 (m, 3H), 1.38-1.29 (m, 1H), 1.11-0.91 (m, 3H). |
| 57 | 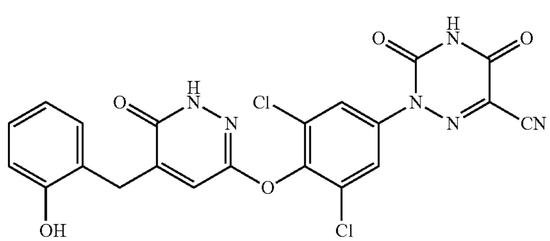 [SMILES: N#Cc1nn(-c2cc(Cl)c(Oc3cc(Cc4ccccc4O)c(=O)[nH]n3)c(Cl)c2)c(=O)[nH]c1=O] | 499.4 | HNMR (400 MHz, DMSO-d6, ppm): δ 12.35 (s, 1H), 9.58 (s, 1H), 7.72 (s, 2H), 7.15-7.08 (m, 2H), 6.92 (s, 1H), 6.83(d, J = 7.6 Hz, 1H), 6.77(t, J = 7.6 Hz, 1H), 3.72 (s, 2H). |
| 59 | 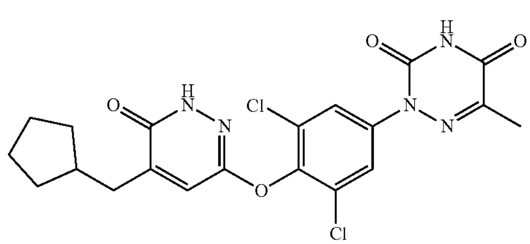 [SMILES: Cc1nn(-c2cc(Cl)c(Oc3cc(CC4CCCC4)c(=O)[nH]n3)c(Cl)c2)c(=O)[nH]c1=O] | 464.4 | HNMR (400 MHz, DMSO-d6, ppm): δ 12.37 (br s, 1H), 12.17 (s, 1H), 7.75 (s, 2H), 7.47(s, 1H), 2.48-2.47 (m, 2H), 2.20-2.17 (m, 1H), 2.12 (s, 3H), 1.68-1.62 (m, 2H), 1.60-1.57 (m, 2H), 1.49-1.46 (m, 2H), 1.19-1.15 (m, 2H). |

TABLE 1-continued

Characterization of Selected Compounds

| Compound No. | Structure | [M + H]+ | ¹HNMR and ¹⁹FNMR |
|---|---|---|---|
| 60 | 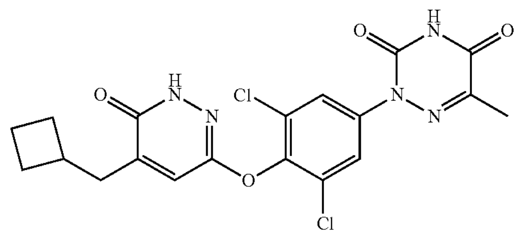 [SMILES: Cc1nn(-c2cc(Cl)c(Oc3cc(CC4CCC4)c(=O)[nH]n3)c(Cl)c2)c(=O)[nH]c1=O] | 450.3 | HNMR (400 MHz, DMSO-d$_6$, ppm): δ 12.37 (s, 1H), 12.17 (s, 1H), 7.75 (s, 2H), 7.37 (s, 1H), 2.61-2.58 (m, 3H), 2.12 (s, 3H), 2.03-2.00 (m, 2H), 1.82-1.77 (m, 2H), 1.71-1.69 (m, 2H). |
| 61 | 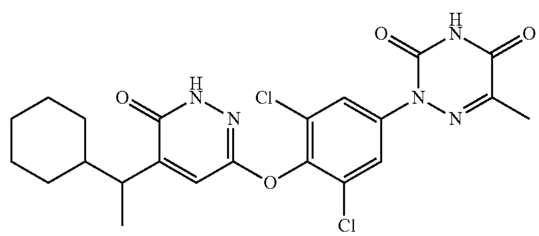 [SMILES: Cc1nn(-c2cc(Cl)c(Oc3cc(C(C)C4CCCCC4)c(=O)[nH]n3)c(Cl)c2)c(=O)[nH]c1=O] | 492.0 | HNMR (400 MHz, DMSO-d$_6$, ppm): δ 12.18 (s, 1H), 7.79 (s, 2H), 7.42 (s, 1H), 2.85 (t, J = 7.2 Hz, 1H), 2.14 (s, 3H), 1.81-1.54 (m, 5H), 1.52-1.42 (m, 1H), 1.22-1.10 (m, 3H), 1.15 (d, J = 7.2 Hz, 3H), 1.05-0.87 (m, 2H). |
| 62 | 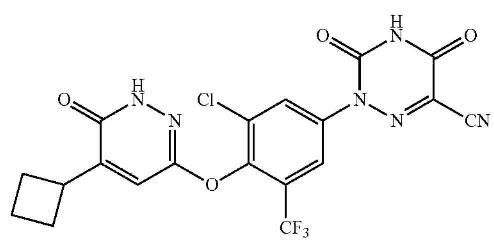 [SMILES: N#Cc1nn(-c2cc(Cl)c(Oc3cc(C4CCC4)c(=O)[nH]n3)c(C(F)(F)F)c2)c(=O)[nH]c1=O] | 481.2 | HNMR (400 MHz, DMSO-d$_6$, ppm): δ 12.20 (s, 1H), 8.13 (d, J = 2.4 Hz, 1H), 7.97 (d, J = 2.4 Hz, 1H), 7.48 (d, J = 1.2 Hz, 1H), 3.60-3.52 (m, 1H), 2.22-2.33 (m, 2H), 2.17-2.09 (m, 2H), 2.04-1.98 (m, 1H), 1.86-1.78 (m, 1H). |
| 63 | 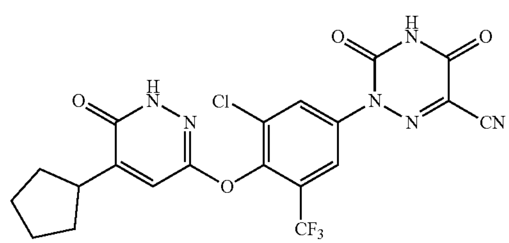 | 495.1 | HNMR (300 MHz, DMSO-d$_6$, ppm): δ 8.13 (d, J = 2.4 Hz, 1H), 7.97 (d, J = 2.4 Hz, 1H), 7.46 (s, 1H), 3.07-3.17 (m, 1H), 2.06-1.89 (m, 2H), 1.79-1.52 (m, 6H).<br>FNMR (282 MHz, DMSO-d$_6$, ppm): δ −60.81. |
| 64 | 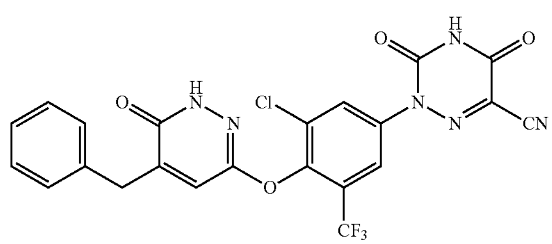 [SMILES: N#Cc1nn(-c2cc(Cl)c(Oc3cc(Cc4ccccc4)c(=O)[nH]n3)c(C(F)(F)F)c2)c(=O)[nH]c1=O] | 517.2 | HNMR (300 MHz, DMSO-d$_6$, ppm) δ 13.33 (bs, 1H), 12.37 (s, 1H), 8.12 (d, J = 2.5 Hz, 1H), 7.96 (d, J = 2.4 Hz, 1H), 7.39-7.32 (m, 5H), 7.24-7.30 (m, 1H), 3.87 (s, 2H).<br>FNMR (282 MHz, DMSO-d$_6$, ppm): δ −60.85. |
| 65 | 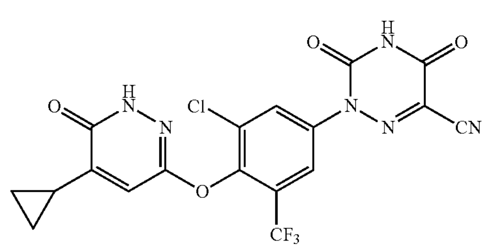 [SMILES: N#Cc1nn(-c2cc(Cl)c(Oc3cc(C4CC4)c(=O)[nH]n3)c(C(F)(F)F)c2)c(=O)[nH]c1=O] | 467.2 | HNMR (400 MHz, DMSO-d$_6$, ppm): δ 13.40 (bs, 1H), 12.25 (m, 1H), 8.12 (d, J = 2.4 Hz, 1H), 7.96 (d, J = 2.4 Hz, 1H), 7.20 (m, 1H), 2.18-2.12 (m, 1H), 1.09-1.01 (m, 4H).<br>FNMR (376 MHz, DMSO-d$_6$, ppm): δ −60.83. |

TABLE 1-continued

Characterization of Selected Compounds

| Compound No. | Structure | [M + H]+ | 1HNMR and 19FNMR |
|---|---|---|---|
| 66 | 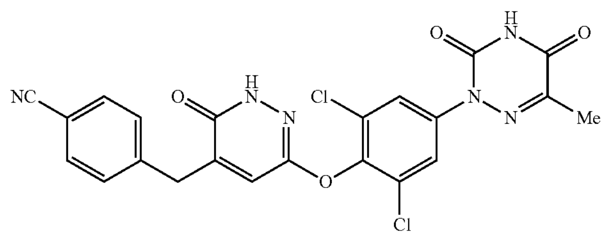 [SMILES: Cc1nn(-c2cc(Cl)c(Oc3cc(Cc4ccc(C#N)cc4)c(=O)[nH]n3)c(Cl)c2)c(=O)[nH]c1=O] | 497.3 | HNMR (400 MHz, DMSO-d6, ppm): δ 12.37 (bs, 1H), 12.33 (s, 1H), 7.78 (d, J = 8.4 Hz, 2H), 7.75 (s, 2H), 7.52 (d, J = 8.4 Hz, 2H), 7.44 (s, 1H), 3.92 (s, 2H), 2.12 (s, 3H). |
| 67 | 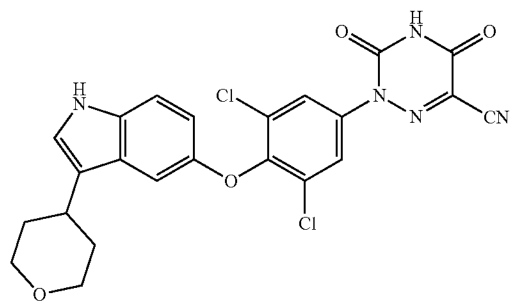 [SMILES: N#Cc1nn(-c2cc(Cl)c(Oc3ccc4[nH]cc(C5CCOCC5)c4c3)c(Cl)c2)c(=O)[nH]c1=O] | 498.2 | HNMR (300 MHz, DMSO-d6, ppm): δ 10.86 (s, 1H), 7.81 (s, 2H), 7.30 (d, J = 9.0 Hz, 1H), 7.17 (d, J = 2.1 Hz, 1H), 7.02 (d, J = 2.4 Hz, 1H), 6.62 (dd, J = 8.7, 2.4 Hz, 1H), 3.90-3.94 (m, 2H), 3.48 (t, J = 11.7 Hz, 2H), 2.98-2.90 (m, 1H), 1.78-1.84 (m, 2H), 1.70-1.62 (m, 2H). |
| 68 | 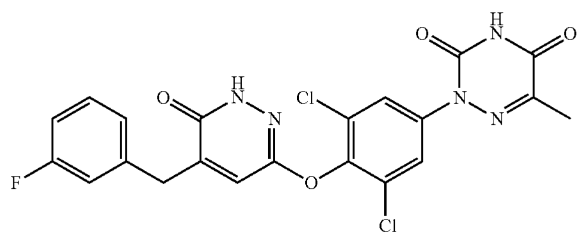 [SMILES: Cc1nn(-c2cc(Cl)c(Oc3cc(Cc4cccc(F)c4)c(=O)[nH]n3)c(Cl)c2)c(=O)[nH]c1=O] | 490.3 | HNMR (400 MHz, DMSO-d6, ppm): δ 12.36 (bs, 1H), 12.31 (s, 1H), 7.74 (s, 2H), 7.38-7.33 (m, 2H), 7.19-7.14 (m, 2H), 7.04-7.06 (m, 1H), 3.84 (s, 2H), 2.12 (s, 3H). |
| 69 | 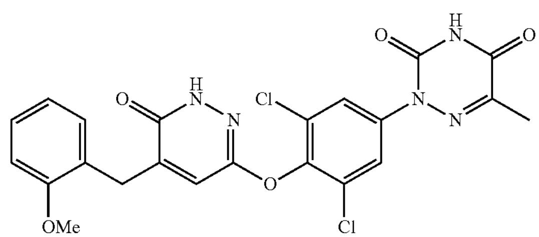 [SMILES: COc1ccccc1Cc1cc(Oc2c(Cl)cc(-n3nc(C)c(=O)[nH]c3=O)cc2Cl)n[nH]c1=O] | 502.4 | HNMR (400 MHz, DMSO-d6, ppm): δ 12.37 (s, 1H), 12.29 (s, 1H), 7.74 (s, 2H), 7.27 (t, J = 8.8 Hz, 1H), 7.18 (d, J = 7.6 Hz, 1H), 7.02 (d, J = 8.0 Hz, 1H), 6.91 (t, J = 7.2 Hz, 1H), 6.84 (s, 1H), 3.76 (s, 5H), 2.11 (s, 3H). |
| 75 Enantiomer A | 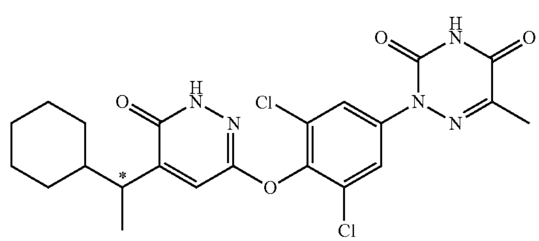 [SMILES: Cc1nn(-c2cc(Cl)c(Oc3cc(C(C)C4CCCCC4)c(=O)[nH]n3)c(Cl)c2)c(=O)[nH]c1=O] | 491.9 | HNMR (300 MHz, DMSO-d6, ppm): δ 12.41 (s, 1H), 12.19 (s, 1H), 7.79 (s, 2H), 7.42 (s, 1H), 2.85 (t, J = 6.9 Hz, 1H), 2.14 (s, 3H), 1.81-1.54 (m, 5H), 1.48 (d, J = 10.8 Hz, 1H), 1.14 (m, 6H), 1.05-0.87 (m, 2H). Chiral column: Chiralpak IC, column size: 0.46*5 cm, particle size: 3.0 um, mobile phase: (Hexane:DCM = 5:1):EtOH = 80:20, flow rate: 1.0 mL/min, ambient temperature. First eluent. Retention time, 3.877 min. |
| 76 Enantiomer B | 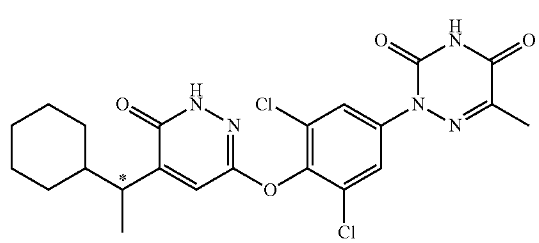 [SMILES: Cc1nn(-c2cc(Cl)c(Oc3cc(C(C)C4CCCCC4)c(=O)[nH]n3)c(Cl)c2)c(=O)[nH]c1=O] | 491.9 | HNMR (300 MHz, DMSO-d6, ppm): δ 12.41 (s, 1H), 12.19 (s, 1H), 7.79 (s, 2H), 7.42 (s, 1H), 2.85 (t, J = 6.9 Hz, 1H), 2.14 (s, 3H), 1.81-1.54 (m, 5H), 1.48 (d, J = 10.8 Hz, 1H), 1.14 (m, 6H), 1.05-0.87 (m, 2H). Chiral column: Chiralpak IC, column size: 0.46*5 cm, particle size: 3.0 um, mobile phase: (Hexane:DCM = 5:1):EtOH = 80:20, flow rate: 1.0 mL/min, ambient temperature. Second eluent. Retention time, 4.720 min. |

TABLE 1-continued

Characterization of Selected Compounds

| Compound No. | Structure | [M + H]+ | ¹HNMR and ¹⁹FNMR |
|---|---|---|---|
| 77 | 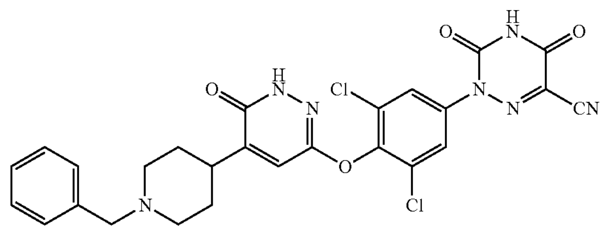 [SMILES: N#Cc1nn(-c2cc(Cl)c(Oc3cc(C4CCN(Cc5ccccc5)CC4)c(=O)[nH]n3)c(Cl)c2)c(=O)[nH]c1=O] | 566.1 | HNMR (400 MHz, CD₃OD, ppm): δ 7.76 (s, 2H), 7.41-7.38 (m, 6H), 3.70-3.80 (m, 2H), 2.98-2.88 (m, 2H), 2.40-2.33 (m, 2H), 2.04-1.95 (m, 3H), 1.80-1.74 (m, 2H). |
| 78 | 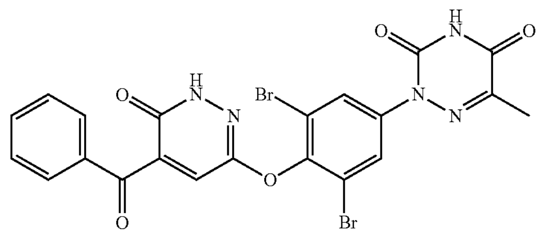 [SMILES: Cc1nn(-c2cc(Br)c(Oc3cc(C(=O)c4ccccc4)c(=O)[nH]n3)c(Br)c2)c(=O)[nH]c1=O] | 574.1 | HNMR (300 MHz, DMSO-d₆, ppm): δ 8.00 (s, 2H), 7.98-7.92 (m, 2H), 7.77-7.68 (m, 2H), 7.65-7.56 (m, 2H), 2.29 (s, 3H). |
| 79 | 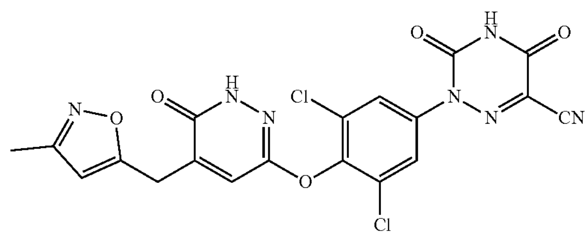 [SMILES: Cc1cc(Cc2cc(Oc3c(Cl)cc(-n4nc(C#N)c(=O)[nH]c4=O)cc3Cl)n[nH]c2=O)on1] | 488.3 | HNMR (400 MHz, DMSO-d₆, ppm): δ 13.25 (bs, 1H), 12.43 (s, 1H), 7.76 (s, 2H), 7.53 (s, 1H), 6.20 (s, 1H), 4.01 (s, 2H), 2.18 (s, 3H). |
| 81 | 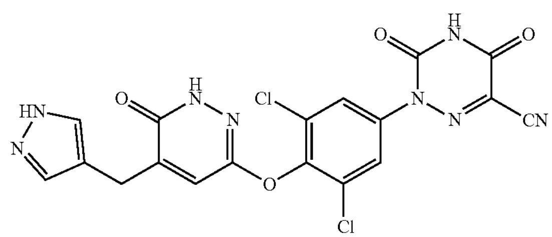 [SMILES: N#Cc1nn(-c2cc(Cl)c(Oc3cc(Cc4cn[nH]c4)c(=O)[nH]n3)c(Cl)c2)c(=O)[nH]c1=O] | 473.3 | HNMR (400 MHz, DMSO-d₆, ppm): δ 13.20 (bs, 1H), 12.74 (bs, 1H), 12.28 (s, 1H), 7.74 (s, 2H), 7.53 (s, 2H), 7.19 (s, 1H), 3.66 (s, 2H). |
| 82 | 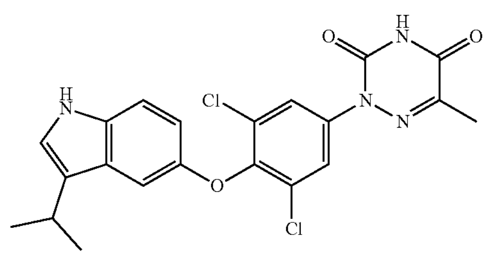 [SMILES: Cc1nn(-c2cc(Cl)c(Oc3ccc4[nH]cc(C(C)C)c4c3)c(Cl)c2)c(=O)[nH]c1=O] | 445.1 | HNMR (400 MHz, DMSO-d₆, ppm): δ 12.42 (s, 1H), 10.77 (s, 1H), 7.84 (s, 2H), 7.31 (d, J = 8.8 Hz, 1H), 7.12 (d, J = 2.0 Hz, 1H), 6.89 (d, J = 2.4 Hz, 1H), 6.67 (dd, J = 8.8, 2.4 Hz, 1H), 3.06-2.96 (m, 1H), 2.19 (s, 3H), 1.24 (d, J = 6.8 Hz, 6H). |
| 83 | 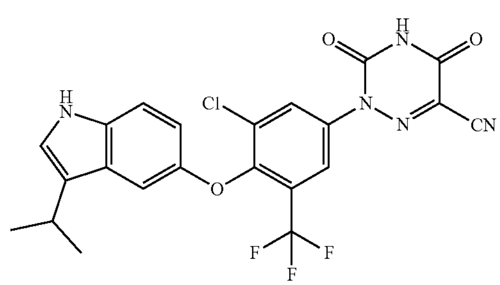 [SMILES: CC(C)c1c[nH]c2ccc(Oc3c(Cl)cc(-n4nc(C#N)c(=O)[nH]c4=O)cc3C(F)(F)F)cc12] | 490.1 | HNMR (300 MHz, DMSO-d₆, ppm): δ 13.23 (bs, 1H), 10.80 (s, 1H), 8.10 (d, J = 2.4 Hz, 1H), 8.00 (d, J = 2.4 Hz, 1H), 7.30 (d, J = 8.8 Hz, 1H), 7.12 (d, J = 2.1 Hz, 1H), 6.90 (d, J = 2.4 Hz, 1H), 6.68 (dd, J = 8.7, 2.4 Hz, 1H), 3.01 (m, 1H), 1.22 (d, J = 6.8 Hz, 6H). FNMR (282 MHz, DMSO-d₆, ppm): δ −60.52. |

TABLE 1-continued

Characterization of Selected Compounds

| Compound No. | Structure | [M + H]⁺ | ¹HNMR and ¹⁹FNMR |
|---|---|---|---|
| 87 | 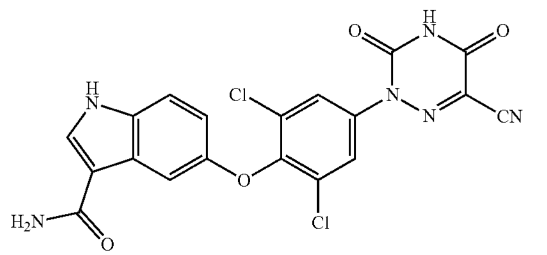 [SMILES: N#Cc1nn(-c2cc(Cl)c(Oc3ccc4[nH]cc(C(N)=O)c4c3)c(Cl)c2)c(=O)[nH]c1=O] | 457.1 | HNMR (300 MHz, DMSO-$d_6$, ppm): δ 13.29 (bs, 1H), 11.58 (s, 1H), 8.05 (d, J = 3.0 Hz, 1H), 7.83 (s, 2H), 7.44-7.14 (m, 3H), 6.89 (dd, J = 8.7, 2.4 Hz, 1H), 6.71 (bs, 1H). |
| 88 Enantiomer A | 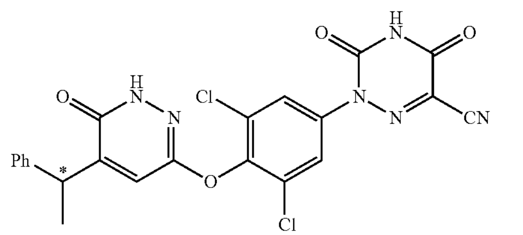 [SMILES: CC(c1ccccc1)c1cc(Oc2c(Cl)cc(-n3nc(C#N)c(=O)[nH]c3=O)cc2Cl)n[nH]c1=O] | 497.3 | HNMR (300 MHz, DMSO-$d_6$, ppm): δ 13.26 (bs, 1H), 12.26 (s, 1H), 7.78 (s, 2H), 7.54 (s, 1H), 7.39-7.32 (m, 4H), 7.29-7.21 (m, 1H), 4.31 (q, J = 7.2 Hz, 1H), 1.56 (d, J = 7.2 Hz, 3H). Chiral column: Whelk-O 1-(R, R), column size: 0.46*5 cm, particle size: 3.5 um, mobile phase: NH₃•H₂O (pH = 9.5):MeOH = 10:90, flow rate: 1.0 mL/min, ambient temperature. First eluent. Retention time, 0.779 min. |
| 89 Enantiomer B | 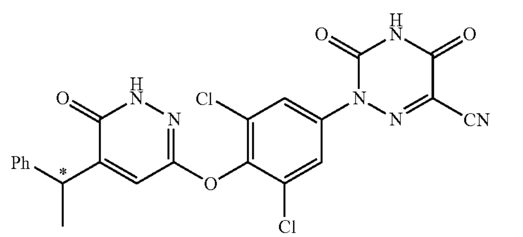 [SMILES: CC(c1ccccc1)c1cc(Oc2c(Cl)cc(-n3nc(C#N)c(=O)[nH]c3=O)cc2Cl)n[nH]c1=O] | 497.3 | HNMR (300 MHz, DMSO-$d_6$, ppm): δ 13.25 (bs, 1H), 12.26 (s, 1H), 7.78 (s, 2H), 7.54 (s, 1H), 7.40-7.29 (m, 4H), 7.29-7.21 (m, 1H), 4.31 (q, J = 7.2 Hz, 1H), 1.56 (d, J = 7.2 Hz, 3H). Chiral column: Whelk-O 1-(R, R), column size: 0.46*5 cm, particle size: 3.5 um, mobile phase: NH₃•H₂O (pH = 9.5):MeOH = 10:90, flow rate: 1.0 mL/min, ambient temperature. Second eluent. Retention time: 1.115 min. |
| 92 Enantiomer A | 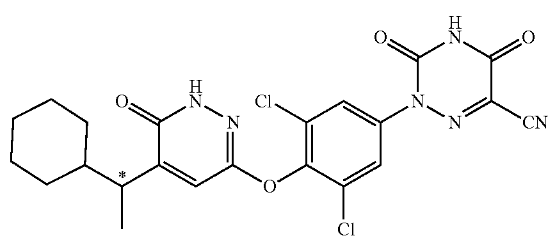 [SMILES: CC(c1cc(Oc2c(Cl)cc(-n3nc(C#N)c(=O)[nH]c3=O)cc2Cl)n[nH]c1=O)C1CCCCC1] | 503.2 | (HNMR (300 MHz, DMSO-$d_6$, ppm): δ 13.25 (bs, 1H), 12.22 (s, 1H), 7.79 (s, 2H), 7.44 (s, 1H), 2.90-2.83 (m, 1H), 1.78-1.41 (m, 6H), 1.30-1.06 (m, 3H), 1.15 (d, J = 7.2 Hz, 3H), 1.05-0.89 (m, 2H). Chiral column: Whelk-O 1-(R, R), column size: 0.46*5 cm, particle size: 3.0 um, mobile phase: (MTBE with 0.1% formic acid):EtOH = 10:90, flow rate: 1.0 mL/min, ambient temperature. First eluent. Retention time: 1.265 min. |
| 93 Enantiomer B | 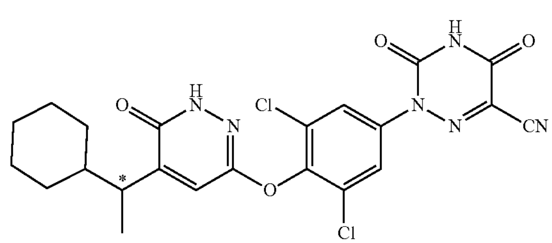 [SMILES: CC(c1cc(Oc2c(Cl)cc(-n3nc(C#N)c(=O)[nH]c3=O)cc2Cl)n[nH]c1=O)C1CCCCC1] | 503.2 | HNMR (300 MHz, DMSO-$d_6$, ppm): δ 13.25 (bs, 1H), 12.22 (s, 1H), 7.79 (s, 2H), 7.44 (s, 1H), 2.90-2.83 (m, 1H), 1.78-1.41 (m, 6H), 1.30-1.06 (m, 3H), 1.15 (d, J = 7.2 Hz, 3H), 1.05-0.89 (m, 2H). Chiral column: Whelk-O 1-(R, R), column size: 0.46*5 cm, particle size: 3.0 um, mobile phase: (MTBE with 0.1% formic acid):EtOH = 10:90, flow rate: 1.0 mL/min, ambient temperature. Second eluent. Retention time: 1.678 min. |
| 94 Racemate | 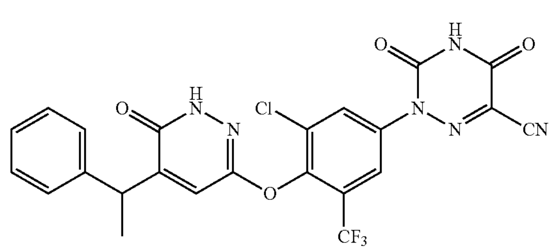 | 531.2 | HNMR (400 MHz, DMSO-$d_6$, ppm): δ 13.35 (bs, 1H), δ 12.29 (s, 1H), 8.12 (d, J = 2.4 Hz, 1H), 7.97 (d, J = 2.4 Hz, 1H), 7.53 (s, 1H), 7.36-7.33 (m, 4H), 7.27-7.20 (m, 1H), 4.30 (q, J = 7.2 Hz, 1H), 1.57 (d, J = 7.2 Hz, 3H). FNMR (376 MHz, DMSO-$d_6$, ppm): δ −60.68. |

TABLE 1-continued

Characterization of Selected Compounds

| Compound No. | Structure | [M + H]+ | 1HNMR and 19FNMR |
|---|---|---|---|
| 95 Enantiomer A | 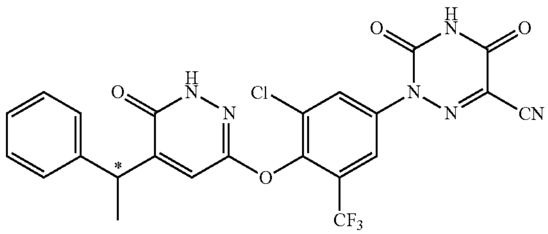 [SMILES: CC(c1ccccc1)c1cc(Oc2c(Cl)cc(-n3nc(C#N)c(=O)[nH]c3=O)cc2C(F)(F)F)n[nH]c1=O] | 531.2 | HNMR (400 MHz, DMSO-d$_6$, ppm): δ 13.35 (bs, 1H), δ 12.29 (s, 1H), 8.12 (d, J = 2.4 Hz, 1H), 7.97 (d, J = 2.4 Hz, 1H), 7.53 (s, 1H), 7.36-7.33 (m, 4H), 7.27-7.20 (m, 1H), 4.30 (q, J = 7.2 Hz, 1H), 1.57 (d, J = 7.2 Hz, 3H). FNMR (376 MHz, DMSO-d$_6$, ppm): δ −60.68. Chiral column: Whelk-O 1-(R, R), column size: 0.46*5 cm, particle size: 3.0 um, mobile phase: NH$_3$•H$_2$O (pH = 9.5):MeOH = 20:80, flow rate: 1.0 mL/min, ambient temperature. First eluent. Retention time: 0.957 min. |
| 96 Enantiomer B | 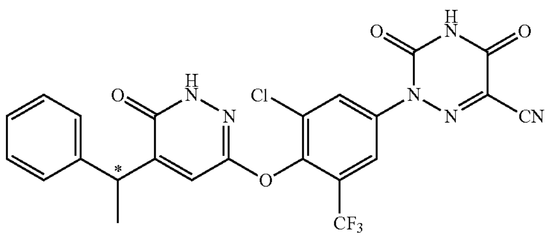 | 531.2 | HNMR (400 MHz, DMSO-d$_6$, ppm): δ 13.35 (bs, 1H), δ 12.29 (s, 1H), 8.12 (d, J = 2.0 Hz, 1H), 7.97 (d, J = 2.0 Hz, 1H), 7.53 (s, 1H), 7.34-7.33 (m, 4H), 7.26-7.21 (m, 1H), 4.30 (q, J = 7.2 Hz, 1H), 1.57 (d, J = 7.2 Hz, 3H). FNMR (376 MHz, DMSO-d$_6$, ppm): δ −60.69. Chiral column: Whelk-O 1-(R, R), column size: 0.46*5 cm, particle size: 3.0 um, mobile phase: NH$_3$•H$_2$O (pH = 9.5):MeOH = 20:80, flow rate: 1.0 mL/min, ambient temperature. Second eluent. Retention time: 1.355 min. |
| 97 Racemate | 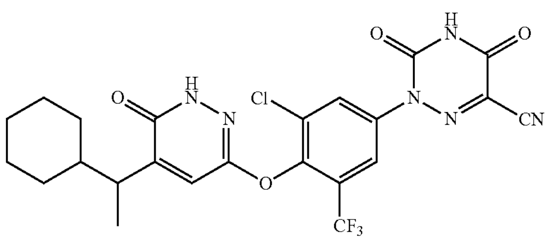 [SMILES: CC(c1cc(Oc2c(Cl)cc(-n3nc(C#N)c(=O)[nH]c3=O)cc2C(F)(F)F)n[nH]c1=O)C1CCCCC1] | 537.3 | HNMR (300 MHz, DMSO-d$_6$, ppm): δ 8.13 (d, J = 2.4 Hz, 1H), 7.97 (d, J = 2.1 Hz, 1H), 7.44 (s, 1H), 2.87 (m, 1H), 1.69-1.62 (m, 5H), 1.49-1.45 (m, 1H), 1.30-1.10 (m, 5H), 1.15 (d, J = 7.2 Hz, 3H). FNMR (282 MHz, DMSO-d$_6$, ppm): δ −60.85. |
| 98 Enantiomer A | 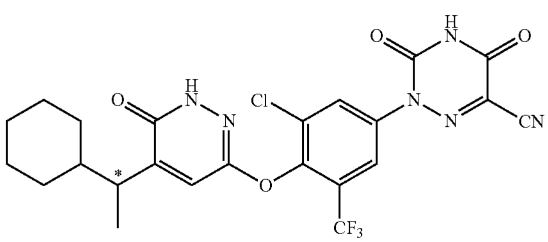 [SMILES: CC(c1cc(Oc2c(Cl)cc(-n3nc(C#N)c(=O)[nH]c3=O)cc2C(F)(F)F)n[nH]c1=O)C1CCCCC1] | 537.3 | HNMR (300 MHz, DMSO-d$_6$, ppm): δ 8.13 (d, J = 2.4 Hz, 1H), 7.97 (d, J = 2.1 Hz, 1H), 7.44 (s, 1H), 2.87 (m, 1H), 1.69-1.62 (m, 5H), 1.49-1.45 (m, 1H), 1.30-1.10 (m, 5H), 1.15 (d, J = 7.2 Hz, 3H). FNMR (282 MHz, DMSO-d$_6$, ppm): δ −60.85. Chiral column: Whelk-O 1-(R, R), column size: 0.46*5 cm, particle size: 3.0 um, mobile phase: (Hexane:MTBE = 1:1 with 0.1% formic acid):EtOH = 80:20, flow rate: 1.0 mL/min, ambient temperature. First eluent. Retention time: 0.971 min. |
| 99 Enantiomer B | 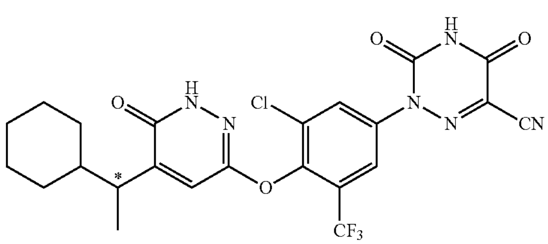 | 537.3 | HNMR (300 MHz, DMSO-d$_6$, ppm): δ 13.36 (bs, 1H), 12.26 (s, 1H), 8.13 (d, J = 2.4 Hz, 1H), 7.97 (d, J = 2.1 Hz, 1H), 7.44 (s, 1H), 2.87 (m, 1H), 1.69-1.62 (m, 5H), 1.49-1.45 (m, 1H), 1.30-1.10 (m, 5H), 1.15 (d, J = 7.2 Hz, 3H). FNMR (282 MHz, DMSO-d$_6$, ppm): δ −60.85. Chiral column: Whelk-O 1-(R, R), column size: 0.46*5 cm, particle size: 3.0 um, mobile phase: (Hexane:MTBE = 1:1 with 0.1% formic acid):EtOH = 80:20, flow rate: 1.0 mL/min, ambient temperature. Second eluent. Retention time: 1.156 min. |

Biological Example 1. Thyroid Hormone Receptor Binding Assay

TR-FRET binding assay was used to test representative compounds herein.

The ligand binding domain of thyroid hormone receptor alpha and the ligand binding domain of thyroid hormone receptor beta with GST tag were purchased from Invitrogen. Biotin-SRC2-2 coactivator peptide was purchased from Sangon Biotech, Europium anti-GST and Streptavidin-D2 was from Cisbio.

Five microliters of 4× compound serial dilution was added in the 384-well plate, white, low volume, round-bottom assay plate. Five microliters of TRβ LBD (2 nM) or TRα LBD (4 nM) in 50 mM Tris-HCl (pH7.4) with 100 mM NaCl, 1 mM EDTA, 50 mM KF, 1 mM DTT, 1 mM $MgCl_2$, 10% glycerol, 0.01% NP-40, 0.1% BSA (reaction buffer) was mixed with 10 microliters of 400 nM Biotin-SRC2-2 (2×) and anti-GST Eu (1:200) (2×) and 50 nM streptavidin-d2 (2×) in reaction buffer in the same assay plate. Centrifuge the assay plates at 1000 g for 1 min and incubate 1 hr at RT, protected from light. Then read the plate at wavelengths of 665 nm and 615 nm on Envision 2104 plate reader. Calculate $EC_{50}$ by fitting % Activity values and log of compound concentrations to nonlinear regression (dose response—variable slope) with Graphpad 5.0.

The results are shown in the table below.

TABLE 2

Binding Activity of Representative Compounds

| Compound | TRβ $EC_{50}$ (μM) | TRα $EC_{50}$ (μM) |
|---|---|---|
| MGL-3196 | 0.30 | 3.24 |
| 1 | 0.54 | 5.76 |
| 2 | 0.76 | 36.67 |
| 3 | 0.49 | 7.80 |
| 4 | 0.81 | 36.67 |
| 5 | >10 | >10 |
| 6 | >10 | >10 |
| 7 | 0.37 | 5.82 |
| 8 | 0.17 | 1.40 |
| 9 | 0.34 | 3.38 |
| 10 | >10 | >10 |
| 11 | 0.51 | 4.0 |
| 12 | 0.15 | 1.40 |
| 13 | 0.12 | 1.35 |
| 14 | 0.37 | 4.06 |
| 15 | 4.33 | 60.23 |
| 16 | 21.44 | >90 |
| 17 | 0.72 | >90 |
| 18 | 0.23 | 80.52 |
| 19 | >90 | >90 |
| 20 | 0.17 | >90 |
| 21 | >90 | >90 |
| 22 | 0.09 | 1.40 |
| 23 | 0.06 | 0.56 |
| 24 | >10 | >10 |
| 25 | 0.64 | >10 |
| 26 | >10 | >10 |
| 27 | 0.48 | 6.90 |
| 28 | 1.21 | >90 |
| 29 | 1.07 | >90 |
| 30 | 1.09 | 11.63 |
| 31 | >10 | >10 |
| 32 | >90 | >90 |
| 33 | 0.08 | 1.27 |
| 34 | >90 | >90 |
| 35 | 0.26 | 2.57 |
| 36 | 11.68 | >90 |
| 37 | 1.55 | 9.82 |
| 38 | >90 | >90 |
| 39 | >10 | >10 |
| 40 | 0.41 | 38.82 |
| 41 | 0.89 | 2.57 |
| 42 | 2.01 | >10 |
| 43 | >10 | >10 |
| 44 | 1.49 | 2.60 |
| 45 | 4.16 | >10 |
| 46 | 0.03 | 0.31 |
| 47 | 0.16 | 1.49 |
| 48 | 0.06 | 1.32 |
| 49 | 0.23 | 3.20 |
| 50 | 8.80 | >90 |
| 51 | >90 | >90 |
| 52 | >90 | >90 |
| 53 | 0.01 | 1.37 |
| 54 | 2.70 | 44.42 |
| 55 | 1.07 | 8.57 |
| 56 | 0.09 | 1.03 |
| 57 | 1.63 | 90.00 |
| 58 | 90.00 | 90.00 |
| 59 | 0.19 | 1.17 |
| 60 | 0.49 | 4.39 |
| 61 | 0.15 | 15.59 |
| 62 | 0.18 | 1.43 |
| 63 | 0.17 | 90.00 |
| 64 | 0.24 | 90.00 |
| 65 | 0.15 | 1.04 |
| 66 | 0.55 | 16.61 |
| 67 | 90.00 | 90.00 |
| 68 | 0.78 | 7.82 |
| 69 | 2.62 | 90.00 |
| 70 | 42.39 | 90.00 |
| 71 | 0.30 | 14.59 |
| 72 | 3.47 | 90.00 |
| 73 | 0.10 | 1.18 |
| 74 | 9.48 | 90.00 |
| 75 | 0.16 | 1.13 |
| 76 | 1.05 | 43.39 |
| 77 | 90.00 | 90.00 |
| 78 | 0.81 | 26.88 |
| 79 | 2.25 | 90.00 |
| 80 | 2.33 | 90.00 |
| 81 | 3.33 | 90.00 |
| 82 | 0.03 | 0.27 |
| 83 | 0.02 | 0.14 |
| 84 | 0.66 | |
| 85 | >90 | |
| 86 | >90 | |
| 87 | 1.21 | |
| 88 | 3.21 | |
| 89 | 0.36 | |
| 90 | 0.18 | |
| 91 | 0.43 | |
| 92 | 0.29 | |
| 93 | 1.56 | |
| 94 | 0.50 | |
| 95 | 0.24 | |
| 96 | 0.84 | |
| 97 | 0.26 | |

Biological Example 2. Thyroid Hormone Receptor Cell Assay

TRα-LBD or TRβ-LBD, coding sequence was inserted into pBIND expression vector (Promega, E1581) to express TRβ-GAL4 binding domain chimeric receptors. This expression vector was transfected into HEK293-LUC host cells with reporter vector (pGL4.35 which carry a stably integrated GAL4 promoter driven luciferase reporter gene). Upon agonist binding to the corresponding TRa-GAL4 or TRb-GAL4 chimeric receptor, the chimeric receptor binds to the GAL4 binding sites and stimulates the reporter gene.

Seed $2.5 \times 10^6$ HEK293-LUC cells into a 60 mm dish and incubated for 16 h at 37° C. under 5% $CO_2$ atmosphere. Mix 12 microliters of Lipo LTX reagent in 250 microliters of Opti-MEM Medium by inversion. Mix 6 ug of DNA in 250 uL of Opti-MEM medium, then add 6 uL of Lipo PLUS Reagent. Add diluted DNA to each tube of diluted Lipo LTX Reagent (1:1 ratio), and mix by Pipettor and incubate at room temperature for 10 min. The reagent mixture was added to a 60 mm dish, incubated with cells for 4-7 h at 37 degrees under 5% $CO_2$ atmosphere.

75 nL compound was added into 384 well assay plate using ECHO550 and then add HEK293-LUC cells (transfected, 17,000 cells/well) into the plate using phenol red-free DMEM containing 5% charcoal/dextran-treated FBS and incubated for 16-20 h at 3° C. under 5% $CO_2$ atmosphere. Add 25 uL of Steady-Glo Luciferase Assay Reagent into each well. Shake for 5 min and then record the luminescence value on Envision 2104 plate reader.

The results are shown in the table below.

TABLE 3

Cell Activity of Representative Compounds

| Compound | TRβ $EC_{50}$ (μM) |
|---|---|
| MGL-3196 | 4.0 |
| 1 | 7.10 |
| 2 | 9.88 |
| 3 | 8.93 |
| 4 | 12.17 |
| 7 | 7.38 |
| 8 | 2.10 |
| 9 | 0.64 |
| 11 | 0.70 |
| 14 | 0.65 |
| 15 | 4.61 |
| 17 | 12.20 |
| 18 | 0.35 |
| 20 | 4.98 |
| 22 | 0.20 |
| 23 | 0.18 |
| 25 | 12.45 |
| 27 | 0.77 |
| 33 | 11.51 |
| 35 | 0.57 |
| 37 | 1.22 |
| 40 | 0.61 |
| 46 | 0.09 |
| 47 | 4.13 |
| 56 | 1.05 |
| 60 | 1.19 |
| 62 | 5.29 |
| 63 | 8.43 |
| 65 | 4.10 |
| 66 | 1.90 |
| 71 | 0.46 |
| 73 | 11.23 |
| 75 | 0.27 |
| 83 | 0.23 |
| 90 | 2.76 |
| 91 | 4.35 |
| 92 | 13.62 |
| 98 | 5.5 |
| 99 | 18.5 |

Biological Example 3. Human Hepatocyte Clearance Study

The in vitro human hepatocyte clearance of compounds described here was studied using pooled human hepatocytes purchased from BioreclamationIVT (Westbury, NY, Cat # X008001, Lot # TQJ). The assay was conducted according to manufacturer's instruction. Briefly, 10 mM stock solutions of test compounds and positive control (Verapamil) were prepared in 100% DMSO. Thawing media (50 mL) used in the study consists of: 31 mL Williams E medium (GIBCO Cat #12551-032); 15 mL isotonic percoll (GE Healthcare Cat #17-0891-09); 500 uL 100×GlutaMax (GIBCO Cat #35050); 750 uL HEPES (GIBCO Cat #15630-080); 2.5 mL FBS (Corning Cat #35-076-CVR); 50 uL human insulin (GIBCO Cat #12585-014) and 5 uL dexamethasone (NICPBP). Incubation media is made of Williams E medium supplemented with 1×GlutaMax. Both thawing medium and incubation medium (serum-free) were placed in a 37° C. water bath for at least 15 minutes prior to use. Compound stock solutions were diluted to 100 μM by combining 198 μL of 50% acetonitrile/50% water and 2 μL of 10 mM stock solution. Verapamil was use as a positive control in the assay. Vials of cryopreserved hepatocytes were removed from storage and thawed in a 37° C. water bath with gentle shaking. Contents of the vial were poured into the 50 mL thawing medium conical tube. Vials were centrifuged at 100 g for 10 minutes at room temperature. Thawing medium was aspirated and hepatocytes were re-suspended with serum-free incubation medium to yield ~1.5×$10^6$ cells/mL. Hepatocyte viability and density were counted using a Trypan Blue exclusion, and then cells were diluted with serum-free incubation medium to a working cell density of 0.5×$10^6$ viable cells/mL. Then, a portion of the hepatocytes at 0.5×$10^6$ viable cells/mL was boiled for 5 minutes prior to adding to the plate as negative control to eliminate the enzymatic activity so that little or no substrate turnover should be observed. The boiled hepatocytes were used to prepare negative samples. Aliquots of 198 μL hepatocytes were dispensed into each well of a 96-well non-coated plate. The plate was placed in the incubator on an orbital shaker at 500 rpm for approximately 10 minutes. Aliquots of 2 μL of the 100 μM test compound or positive control were added into respective wells of the non-coated 96-well plate to start the reaction. This assay was performed in duplicate. The plate was incubated in the incubator on an orbital shaker at 500 rpm for the designated time points. Twenty-five microliter of contents were transferred and mixed with 6 volumes (150 μL) of cold acetonitrile with IS (200 nM imipramine, 200 nM labetalol and 200 nM diclofenac) to terminate the reaction at time points of 0, 15, 30, 60, 90 and 120 minutes. Samples were centrifuged at 3,220 g for 25 minutes and aliquots of 150 μL of the supernatants were used for LC-MS/MS analysis. For data analysis, all calculations were carried out using Microsoft Excel. Peak areas were determined from extracted ion chromatograms. The in vitro half-life ($t_{1/2}$) of parent compound was determined by regression analysis of the percent parent disappearance vs. time curve. The in vitro half-life (in vitro $t_{1/2}$) was determined from the slope value: in vitro $t_{1/2}$=0.693/k. Conversion of the in vitro $t_{1/2}$ (in minutes) into the scale-up unbound intrinsic clearance (scaled-up unbound $CL_{int}$, in mL/min/kg) was done using the following equation (mean of duplicate determinations): Scaled-up unbound $CL_{int}$=kV/N×scaling factor, where V=incubation volume (0.5 mL); N=number of hepatocytes per well (0.25×$10^6$ cells). Scaling factors for in vivo intrinsic clearance prediction using human hepatocytes are listed as: liver weight (g liver/kg body weight): 25.7; hepatocyte concentration ($10^6$ cells/g liver): 99; scaling factor: 2544.3.

The results are shown in the table below:

TABLE 4

Human Hepatocyte Clearance of Exemplary Compounds

| Compound | Human Hepatocyte Remaining Percentage @ 120 min (%) | Human In vitro $T_{1/2}$ (min) | Human In vitro $CL_{int}$ (μL/min/ $10^6$ cells) | Human Scale-up $CL_{int}$ (mL/min/kg) |
|---|---|---|---|---|
| MGL-3196 | 60 | 165 | 8.39 | 21.3 |
| 8 | 98 | ∞* | 0.00* | 0.00* |
| 9 | 79 | 371 | 3.73 | 9.50 |
| 25 | 76 | 337 | 4.11 | 10.5 |
| 27 | 100 | 3406 | 0.41 | 1.04 |
| 35 | 89 | 626 | 2.21 | 5.63 |
| 65 | 94 | 778 | 1.78 | 4.53 |
| 66 | 93 | 881 | 1.57 | 4.00 |

*If calculated $CL_{int}$ < 0, then $T_{1/2}$ and CLint were reported as "∞" and "0.00", respectively.

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound selected from Compound Nos. 27, 35, and 66, or a pharmaceutically acceptable salt thereof:

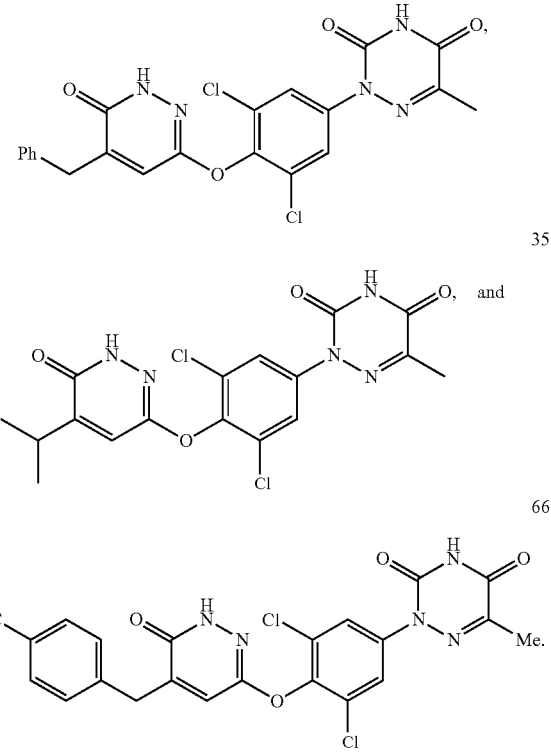

2. A pharmaceutical composition comprising the compound of claim 1 or a pharmaceutically acceptable salt thereof, and optionally a pharmaceutically acceptable carrier.

3. A method of treating a disease or disorder in a subject in need thereof, comprising administering to the subject a therapeutically effective amount of the compound of claim 1 or a pharmaceutically acceptable salt thereof, wherein the disease or disorder is hyperlipidemia, hypercholesterolemia, diabetes, non-alcoholic steatohepatitis, non-alcoholic fatty liver disease, or a combination thereof.

4. A method of treating a liver disease or disorder in a subject in need thereof, comprising administering to the subject a therapeutically effective amount of the compound of claim 1 or a pharmaceutically acceptable salt thereof, wherein the liver disease or disorder is non-alcoholic steatohepatitis or non-alcoholic fatty liver disease.

5. The method of claim 4, wherein the liver disease or disorder is non-alcoholic steatohepatitis.

6. The method of claim 4, wherein the liver disease or disorder is non-alcoholic fatty liver disease.

7. A method of treating a lipid disease or disorder in a subject in need thereof, comprising administering to the subject a therapeutically effective amount of the compound of claim 1 or a pharmaceutical salt thereof, wherein the lipid disease or disorder is hyperlipidemia and/or hypercholesterolemia.

8. The compound of claim 1, or a pharmaceutically acceptable salt thereof, wherein the compound is

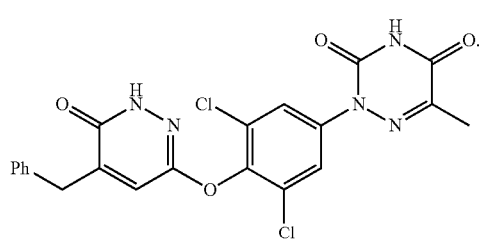

9. The compound of claim 1, or a pharmaceutically acceptable salt thereof, wherein the compound is

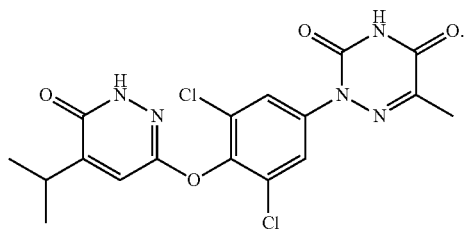

10. The compound of claim 1, or a pharmaceutically acceptable salt thereof, wherein the compound is

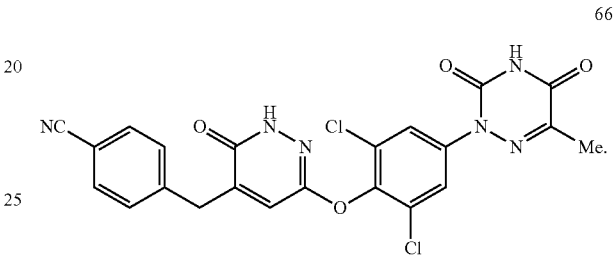

* * * * *